United States Patent
Zhang et al.

(10) Patent No.: US 12,297,241 B2
(45) Date of Patent: May 13, 2025

(54) METHOD TO ENGINEER TRANSPLANTABLE HUMAN TISSUES

(71) Applicant: The Regents of the University of California, Oakland, CA (US)

(72) Inventors: Kun Zhang, La Jolla, CA (US); Yan Wu, La Jolla, CA (US); Amir Dailamy, La Jolla, CA (US); Prashant Mali, La Jolla, CA (US); Daniella McDonald, La Jolla, CA (US); Udit Parekh, La Jolla, CA (US); Michael Hu, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 1005 days.

(21) Appl. No.: 17/257,951

(22) PCT Filed: Jul. 3, 2019

(86) PCT No.: PCT/US2019/040590
§ 371 (c)(1),
(2) Date: Jan. 5, 2021

(87) PCT Pub. No.: WO2020/010249
PCT Pub. Date: Jan. 9, 2020

(65) Prior Publication Data
US 2022/0235104 A1    Jul. 28, 2022

Related U.S. Application Data

(60) Provisional application No. 62/694,954, filed on Jul. 6, 2018.

(51) Int. Cl.
| | |
|---|---|
| *C07K 14/47* | (2006.01) |
| *A61K 31/522* | (2006.01) |
| *A61K 45/06* | (2006.01) |
| *C12N 5/071* | (2010.01) |
| *C12N 9/22* | (2006.01) |
| *C12N 15/11* | (2006.01) |
| *C12N 15/86* | (2006.01) |

(52) U.S. Cl.
CPC ........ *C07K 14/4702* (2013.01); *A61K 31/522* (2013.01); *A61K 45/06* (2013.01); *C12N 5/0697* (2013.01); *C12N 9/22* (2013.01); *C12N 15/111* (2013.01); *C12N 15/86* (2013.01); *C12N 2310/20* (2017.05)

(58) Field of Classification Search
CPC .. C07K 14/4702; A61K 31/522; A61K 45/06; A61K 35/545; C12N 5/0697; C12N 9/22; C12N 15/111; C12N 15/86; C12N 2310/20; C12N 2506/1353; C12N 2506/28; C12N 2506/45; C12N 2501/65; C12N 5/0606; C12N 2506/02; C12N 2510/00; C12N 5/0062; C12N 5/0693; C12N 15/63
See application file for complete search history.

(56) References Cited

U.S. PATENT DOCUMENTS

| | | |
|---|---|---|
| 2003/0036524 A1 | 2/2003 | Licthenberg |
| 2013/0195801 A1 | 8/2013 | Gao et al. |
| 2016/0201089 A1 | 7/2016 | Gersbach et al. |

FOREIGN PATENT DOCUMENTS

| | | | |
|---|---|---|---|
| WO | WO-01/59076 A2 | 8/2001 | |
| WO | WO-2016163958 A1 * | 10/2016 | ............. C12N 15/85 |

OTHER PUBLICATIONS

Abernathy et al., "MicroRNAs Induce a Permissive Chromatin Environment that Enables Neuronal Subtype-Specific Reprogramming of Adult Human Fibroblasts", Cell Stem Cell, vol. 21, Published Sep. 7, 2017, pp. 332-346. (Year: 2017).*
International Search Report and Written Opinion dated Nov. 20, 2019, from application No. PCT/US2019/040590.
Kennedy, et al., "Rapid blue light induction of protein interactions in living cells," Nat Methods, Oct. 31, 2020, vol. 7, pp. 973-975.
Morita, et al., "ETS transcription factor ETV2 directly converts human fibroblasts into functional endothelial cells," Proc Natl Acad Sci USA, Dec. 24, 2014, vol. 112, pp. 160-165 and Supplemental Information, pp. 1-28.
Rekas, et al., "Crystal Structure of Venus, a Yellow Fluorescent Protein with Improved Maturation and Reduced Environmental," The Journal of Biological Chemistry, Oct. 4, 2002, vol. 277, No. 52, pp. 50573-50578.
Amabile et al., "In vivo generation of transplantable human hematopoietic cells from induced pluripotent stem cells", Blood, Feb. 21, 2013, vol. 121, No. 8, pp. 1255-1264.
Nihongaki et al., "CRISPR-Cas9-based Photoactivatable Transcription System", Chemistry & Biology, 2015, vol. 22, pp. 169-174.
Pang et al., "Induction of human neuronal cells by defined transcription factors", Nature, Aug. 11, 2011, vol. 476, pp. 220-223.
Park et al., "Reprogramming of human somatic cells to pluripotency with defined factors", Nature, Jan. 10, 2008, vol. 451, pp. 141-147.
Polstein et al., "A light-inducible CRISPR-Cas9 system for control of endogenous gene activation", Nature Chemical Biology, Mar. 2015, vol. 11, pp. 198-200.
Sugimura et al., "Haematopoietic stem and progenitor cells from human pluripotent stem cells", Nature, May 25, 2017, vol. 545, pp. 432-438.

(Continued)

*Primary Examiner* — Brian Whiteman
*Assistant Examiner* — Stephanie L Sullivan
(74) *Attorney, Agent, or Firm* — Foley & Lardner LLP

(57) ABSTRACT

This disclosure relates to methods, polynucleotides, vectors, viral particles, cells, and systems or the engineering of human tissues. One aspect of the disclosure relates to using lineage-specific miRNA binding molecules to bias tissue lineage. Another aspect of the disclosure relates to using lineage-specific transcription factor overexpression to bias tissue lineage.

16 Claims, 22 Drawing Sheets
Specification includes a Sequence Listing.

(56) References Cited

OTHER PUBLICATIONS

Suzuki et al., "Generation of Engraftable Hematopoietic Stem Cells From Induced Pluripotent Stem Cells by Way of Teratoma Formation", Molecular Therapy, Jul. 2013, vol. 21, No. 7, pp. 1424-1431.
Takahashi et al., "Human Induced Pluripotent Stem Cells on Autologous Feeders", PLoS ONE, Dec. 2009, vol. 4, Issue 12, e8067, 6 pages.
Xu et al., "Direct Lineage Reprogramming: Strategies, Mechanisms, and Applications", Celle Stem Cell, Feb. 5, 2015, vol. 16, pp. 119-134.
Zhang et al., "Rapid Single-Step Induction of Functional Neurons from Human Pluripotent Stem Cells", Neuron, Jun. 5, 2013, vol. 78, pp. 785-798.

\* cited by examiner

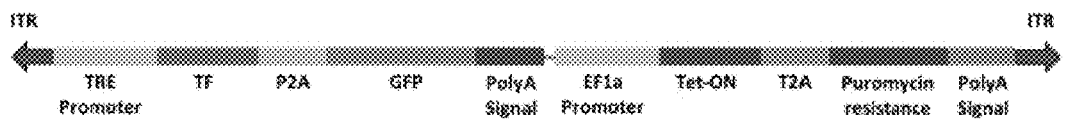
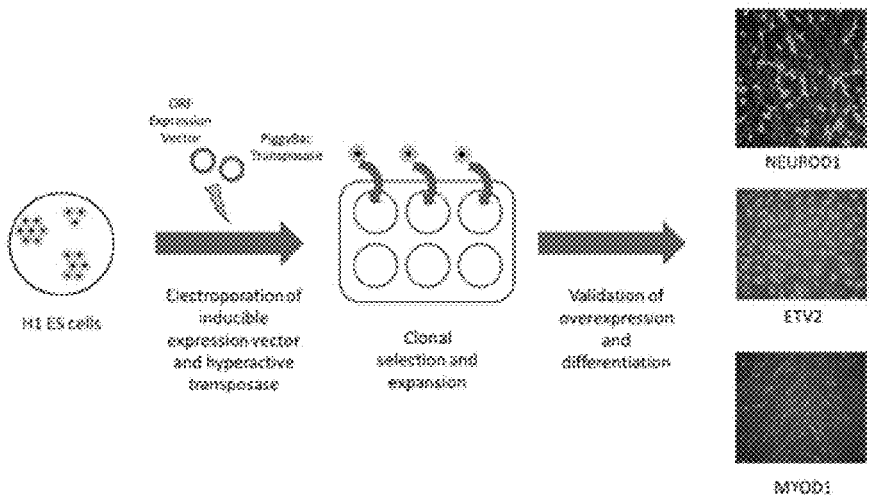
FIGS. 12A – 12B
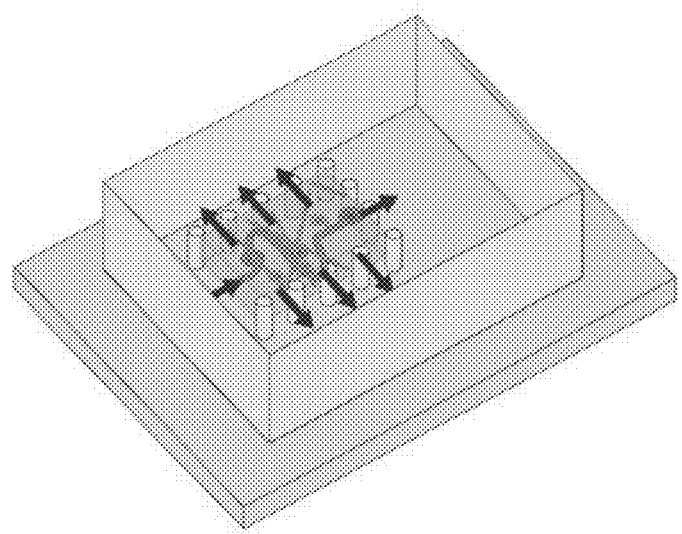
FIG. 13

Day 0　　　　　　　　　　　Day 15

Day 0            Day 10

SEQUENCE LISTING

<160> NUMBER OF SEQ ID NOS: 46

<210> SEQ ID NO 1
<211> LENGTH: 22
<212> TYPE: DNA

```
<213> ORGANISM: Unknown
<220> FEATURE:
<223> OTHER INFORMATION: Description of Unknown:
      Target sequence

<400> SEQUENCE: 1
tcaacatcag tctgataagc ta                                              22

<210> SEQ ID NO 2
<211> LENGTH: 22
<212> TYPE: DNA
<213> ORGANISM: Unknown
<220> FEATURE:
<223> OTHER INFORMATION: Description of Unknown:
      Target sequence

<400> SEQUENCE: 2
caaacaccat tgtcacactc ca                                              22

<210> SEQ ID NO 3
<211> LENGTH: 20
<212> TYPE: DNA
<213> ORGANISM: Unknown
<220> FEATURE:
<223> OTHER INFORMATION: Description of Unknown:
      Target sequence

<400> SEQUENCE: 3
ggcattcacc gcgtgcctta                                                 20

<210> SEQ ID NO 4
<211> LENGTH: 22
<212> TYPE: DNA
<213> ORGANISM: Unknown
<220> FEATURE:
<223> OTHER INFORMATION: Description of Unknown:
      Target sequence

<400> SEQUENCE: 4
cgcattatta ctcacggtac ga                                              22

<210> SEQ ID NO 5
<211> LENGTH: 23
<212> TYPE: DNA
<213> ORGANISM: Unknown
<220> FEATURE:
<223> OTHER INFORMATION: Description of Unknown:
      Target sequence

<400> SEQUENCE: 5
agcaagtaca tccacgttta agt                                             23

<210> SEQ ID NO 6
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tggctagtta agcttgatat cgaattcctg cagcccgggg gatccagatc acaccggtcg     60
cca                                                                   63

<210> SEQ ID NO 7
<211> LENGTH: 67
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gggagagggg ggggggcgg aattccgcgg gcccgtcgac gcggttaacg ccgctttact    60
tgtacag                                                             67

<210> SEQ ID NO 8
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tggctagtta agcttgatat cgaattcctg cagcccgggg gatcctcaac atcagtctga    60
taagctaaga tcacaccggt cgcca                                         85

<210> SEQ ID NO 9
<211> LENGTH: 89
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gggagagggg ggggggcgg aattccgcgg gcccgtcgac gcggtttagc ttatcagact    60
gatgttgaaa cgccgcttta cttgtacag                                     89

<210> SEQ ID NO 10
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tggctagtta agcttgatat cgaattcctg cagcccgggg gatcccaaac accattgtca    60
cactccaaga tcacaccggt cgcca                                         85

<210> SEQ ID NO 11
<211> LENGTH: 89
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gggagagggg ggggggcgg aattccgcgg gcccgtcgac gcggtttgga gtgtgacaat    60
ggtgtttgaa cgccgcttta cttgtacag                                     89

<210> SEQ ID NO 12
<211> LENGTH: 83
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 12
tggctagtta agcttgatat cgaattcctg cagcccgggg gatccggcat tcaccgcgtg    60
ccttaagatc acaccggtcg cca                                           83

<210> SEQ ID NO 13
<211> LENGTH: 87
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gggagagggg ggggggcgg aattccgcgg gcccgtcgac gcggtttaag gcacgcggtg    60
aatgccaacg ccgctttact tgtacag                                       87

<210> SEQ ID NO 14
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tggctagtta agcttgatat cgaattcctg cagcccgggg gatcccgcat tattactcac    60
ggtacgaaga tcacaccggt cgcca                                         85

<210> SEQ ID NO 15
<211> LENGTH: 89
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gggagagggg ggggggcgg aattccgcgg gcccgtcgac gcggtttcgt accgtgagta    60
ataatgcgaa cgccgcttta cttgtacag                                     89

<210> SEQ ID NO 16
<211> LENGTH: 86
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tggctagtta agcttgatat cgaattcctg cagcccgggg gatccagcaa gtacatccac    60
gtttaagtag atcacaccgg tcgcca                                        86

<210> SEQ ID NO 17
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gggagagggg ggggggcgg aattccgcgg gcccgtcgac gcggttactt aaacgtggat    60
gtacttgcta acgccgcttt acttgtacag    90

<210> SEQ ID NO 18
<211> LENGTH: 1914
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
atggcttcgt acccctgcca tcaacacgcg tctgcgttcg accaggctgc gcgttctcgc    60
ggccatagca accgacgtac ggcgttgcgc cctcgccggc agcaagaagc cacggaagtc   120
cgcctggagc agaaaatgcc cacgctactg cgggtttata tagacggtcc tcacgggatg   180
gggaaaacca ccaccacgca actgctggtg gccctgggtt cgcgcgacga tatcgtctac   240
gtacccgagc cgatgactta ctggcaggtg ctggggcctt ccgagacaat cgcgaacatc   300
tacaccacac aacaccgcct cgaccagggt gagatatcgg ccggggacgc ggcggtggta   360
atgacaagcg cccagataac aatgggcatg cctatgccg tgaccgacgc cgttctggct   420
cctcatatcg ggggggaggc tgggagctca catgccccgc cccggcccct caccctcatc   480
ttcgaccgcc atcccatcgc cgccctcctg tgctacccgg ccgcgcgata ccttatgggc   540
agcatgaccc cccaggccgt gctggcgttc gtggccctca tcccgccgac cttgcccggc   600
acaaacatcg tgttgggggc ccttccggag acagacaca tcgaccgcct ggccaaacgc   660
cagcgccccg gcgagcggct tgacctggct atgctggccg cgattcgccg cgtttacggg   720
ctgcttgcca atacggtgcg gtatctgcag ggcggcgggt cgtggcggga ggattgggga   780
cagctttcgg ggacggccgt gccgccccag ggtgccgagc cccagagcaa cgcgggccca   840
cgaccccata tcggggacac gttatttacc ctgtttcggg cccccgagtt gctggccccc   900
aacggcgacc tgtacaacgt gtttgcctgg gccttggacg tcttggccaa cgcctccgt    960 cccatgcacg tctttatcct ggattacgac caatcgcccg ccggctgccg ggacgccctg   1020
ctgcaactta cctccgggat ggtccagacc cacgtcacca cccccggctc catccgacg   1080 atctgcgacc tggcgcgcac gttgcccgg gagatggggg aggctaacgg atccggcgca   1140
acaaacttct ctctgctgaa acaagccgga gatgtcgaag agaatcctgg accgatggtg   1200
agcaagggcg aggagctgtt caccggggtg gtgcccatcc tggtcgagct ggacggcgac   1260
gtaaacggcc acaagttcag cgtgtccggc gagggcgagg gcgatgccac ctacggcaag   1320
ctgaccctga agttcatctg caccaccggc aagctgcccg tgccctggcc cacccctgtg   1380
accaccctga cctacggcgt gcagtgcttc agccgctacc ccgaccacat gaagcagcac   1440
gacttcttca gtccgccat gcccgaaggc tacgtccagg agcgcaccat cttcttcaag   1500
gacgacggca actacaagac ccgcgccgag gtgaagttcg agggcgacac cctggtgaac   1560
cgcatcgagc tgaagggcat cgacttcaag gaggacggca acatcctggg cacaagctg   1620 gagtacaact acaacagcca caacgtctat atcatggccg acaagcagaa gaacggcatc   1680
aaggtgaact tcaagatccg ccacaacatc gaggacggca cgtgcagct cgccgaccac   1740 taccagcaga acacccccat cggcgacggc cccgtgctgc tgcccgacaa ccactacctg   1800
agcacccagt ccgccctgag caaagacccc aacgagaagc gcgatcacat ggtcctgctg   1860
gagttcgtga ccgccgccgg gatcactctc ggcatggacg agctgtacaa gtaa         1914

<210> SEQ ID NO 19
<211> LENGTH: 1210
<212> TYPE: DNA
<213> ORGANISM: Homo sapiens

<400> SEQUENCE: 19

```
cgtgaggctc cggtgcccgt cagtgggcag agcgcacatc gcccacagtc cccgagaagt      60
tgggggagg ggtcggcaat tgaaccggtg cctagagaag gtggcgcggg gtaaactggg      120
aaagtgatgt cgtgtactgg ctccgccttt ttcccgaggg tgggggagaa ccgtatataa      180
gtgcagtagt cgccgtgaac gttcttttc gcaacgggtt tgccgccaga acacaggtaa      240
gtgccgtgtg tggttcccgc gggcctggcc tctttacggg ttatggccct tgcgtgcctt      300
gaattacttc cacgccctg gctgcagtac gtgattcttg atcccgagct tcgggttgga      360
agtgggtggg agagttcgag gccttgcgct taaggagccc cttcgcctcg tgcttgagtt      420
gaggcctggc ctgggcgctg gggccgccgc gtgcgaatct ggtggcacct tcgcgcctgt      480
ctcgctgctt tcgataagtc tctagccatt taaaattttt gatgacctgc tgcgacgctc      540
tttttctggc aagatagtct tgtaaatgcg ggccaagatc tgcacactgg tatttcggtt      600
tttggggccg cgggcggcga cggggcccgt gcgtcccagc gcacatgttc ggcgaggcgg      660
ggcctgcgag cgcggccacc gagaatcgga cggggtagt ctcaagctgg ccggcctgct      720
ctggtgcctg gccctcgcgcc gccgtgtatc gccccgccct gggcggcaag gctggcccgg      780
tcggcaccag ttgcgtgagc ggaaagatgg ccgcttcccg gccctgctgc agggagctca      840
aaatggagga cgcggcgctc gggagagcgg gcgggtgagt cacccacaca aaggaaaagg      900
gcctttccgt cctcagccgt cgcttcatgt gactccacgg agtaccgggc gccgtccagg      960
cacctcgatt agttctcgag cttttggagt acgtcgtctt taggttgggg ggagggttt     1020
tatgcgatgg agtttccccca cactgagtgg gtggagactg aagttaggcc agcttggcac    1080
ttgatgtaat tctccttgga atttgcccctt tttgagtttg gatcttggtt cattctcaag    1140
cctcagacag tggttcaaag tttttttctt ccatttcagg tgtcgtgaaa actaccccta    1200
aaagccaaaa                                                           1210
```

<210> SEQ ID NO 20
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20

```
uagcuuauca gacugauguu ga                                               22
```

<210> SEQ ID NO 21
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21

```
uggaguguga caaugguguu ugu                                              23
```

<210> SEQ ID NO 22
<211> LENGTH: 21

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uaaggcacgc ggugaaugcc a                                              21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ucguaccgug aguaauaaug c                                              21

<210> SEQ ID NO 24
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
acuuaaacgu gguuguacuu gc                                             22

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
uggaauguaa agaaguaugu a                                              21

<210> SEQ ID NO 26
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
uggaagacua gugauuuugu ug                                             22

<210> SEQ ID NO 27
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
ucuuugguua ucuagcugua uga                                            23

<210> SEQ ID NO 28
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 28
uacccuguag auccgaauuu gug                                              23

<210> SEQ ID NO 29
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
uuuggcacua gcacauuuuu gc                                               22

<210> SEQ ID NO 30
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
uugguccccu ucaaccagcu gu                                               22

<210> SEQ ID NO 31
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
uauugcuuaa gaauacgcgu ag                                               22

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
agugguuuua cccuauggua g                                                21

<210> SEQ ID NO 33
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
ugagaugaag cacuguagcu ca                                               22

<210> SEQ ID NO 34
<211> LENGTH: 24
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 34
guccaguuuu cccaggaauc ccuu                                              24

<210> SEQ ID NO 35
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
aacauucaac gcugucggug agu                                               23

<210> SEQ ID NO 36
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
uggacggaga acugauaagg gu                                                22

<210> SEQ ID NO 37
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
cccaguguuc agacuaccug uuc                                               23

<210> SEQ ID NO 38
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
uaauacugcc ugguaaugau gac                                               23

<210> SEQ ID NO 39
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
gugaaauguu uaggaccacu ag                                                22

<210> SEQ ID NO 40
<211> LENGTH: 22
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 40
gagcuuuugg cccggguuau ac                                        22

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
acagcaggca cagacaggca g                                         21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
uugugcuuga ucuaaccaug u                                         21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
ugucaguuug ucaaauaccc c                                         21

<210> SEQ ID NO 44
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
uccagcauca gugauuuugu uga                                       23

<210> SEQ ID NO 45
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 45
uuuguucguu cggcucgcgu ga                                           22

<210> SEQ ID NO 46
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
aaaccguuac cauuacugag uu                                           22
```

METHOD TO ENGINEER TRANSPLANTABLE HUMAN TISSUES

CROSS-REFERENCE TO RELATED APPLICATION

This application is a national stage entry under U.S.C. § 371 of International Application No. PCT/US2019/040590, filed Jul. 3, 2019, which in turn claims priority under 35 U.S.C. § 119(d) to U.S. Provisional Application No. 62/694,954, filed Jul. 6, 2018, the contents of each of which are hereby incorporated by reference into the present disclosure.

STATEMENT OF GOVERNMENT SUPPORT

This invention was made with government support under the Grant No. GM123313, awarded by the National Institutes of Health. Accordingly, the U.S. government has certain rights to the invention.

SEQUENCE LISTING

The instant application contains a Sequence Listing which has been submitted electronically in ASCII format and is hereby incorporated by reference in its entirety. Said ASCII copy, created on Aug. 5, 2021, is named 114198-0292_SL.txt and is 15,699 bytes in size.

BACKGROUND

Engineered human tissue is needed for use in screens, developmental biology applications, and transplants, among other uses. But existing approaches suffer from particular drawbacks. Human organoids lack vasculature and must be generated with extensive, time-consuming protocols. Three-dimensional printing of human tissues is still rudimentary and time-consuming; moreover, it is difficult to obtain thick, biomimetic, fully vascularized tissues by this method. Further, animal models of human tissues are not truly biomimetic. Methods involving human subjects invoke ethical considerations, and tissue from non-patient donors face a substantial risk of rejection.

Accordingly, there is a need in the art for a method of ethically creating transplantable human tissue within as little as a few months from donor induced stem cells or HLA-matched stem cells. This disclosure satisfies this need and provides related advantages.

SUMMARY

Described herein are methods, systems, and compositions to engineer tissue using lineage-specific biasing. The methods, systems, and compositions described herein provide high utility and versatility when compared to other methods, systems, and compositions for engineering tissue.

The novel methodologies and technologies allows one to engineer transplantable human tissues in both vivo and ex vivo contexts. Thus, in one aspect described herein is an in vivo methodology utilizing a teratoma as a tool to produce vascularized human tissues. As described hine, these teratomas were grown in immunocompromised mice but can also be grown in other mammals such as but not limited to rat, pig, sheep, dog, and non-human primates. The animal hosts may or may not be immune privileged. Teratomas also can be grown subcutaneously in addition to being grown in the host muscle, brain, testis, mammary fat pad, kidney, liver, lung, heart, gut, bone, eye, spleen, pancreas, and peritoneum. Vuscularized human tissues can be engineered in vivo with the teratoma via the disclosed novel mIRNA circuits or via cell fate biasing through transcription factor (TF) overexpression. Notably single or multiple miRNA constructs and single or multiple TFs can be used. These miRNA circuits and TF overexpression vectors can be delivered via lentivirus, knocked into a safe harbor, or delivered during growth of the teratoma itself. The constructs may be constitutively expressed or transiently. Drug administration (ganciclovir, doxycycline, etc) can be used to allow the mIRNA circuits to function constantly or transiently as well. This molecular sculpting technology can also be applied to organoids in vivo and ex vivo.

Also described herein are ex vivo technologies via 3D bioprinting. These technologies allow the capability to grow tissues, teratomas, or organoids ex vivo. All in all, novel technologies and methodologies to grow vascularized transplantable human tissues in vivo and ex vivo are described.

In the aspect Applicant has developed a technology that is capable of growing human tissue by way of biasing the differentiation of a stem cell population using lineage-specific miRNA and transcription factor (TF) overexpression vectors.

Accordingly, in some aspects, provided herein is a method comprising, or alternatively consisting essentially of, or yet further consisting of, the step of administering a prodrug to a mixed cell population comprising a lineage-specific miRNA-binding polynucleotide, wherein the lineage-specific miRNA-binding polynucleotide comprises, or consists essentially of, or yet further consists of: (i) at least one lineage-specific miRNA binding site operably linked to (ii) a polynucleotide encoding a prodrug modification polypeptide, and wherein the mixed cell population comprises at least one cell comprising a lineage-specific miRNA capable of binding to the lineage-specific miRNA binding site. In some embodiments, the binding of the lineage-specific miRNA to the miRNA-binding site silences expression of the prodrug modification polypeptide.

In some embodiments, the prodrug is cytotoxic when modified by the prodrug modification polypeptide. In some embodiments, the prodrug modification polypeptide is selected from a viral tyrosine kinase, a bacterial cytosine deaminase, carboxypeptidase G2, purine nucleoside phosphorylase, nitroreductase, deoxycytidine kinase, cytochrome P450, a horseradish peroxidase, a guanine ribosyltransferase, a β-glucuronidase, a β-galactosidase, a thymidine phosphorylase, methionine-α,γ-lyase, and an equivalent of each thereof. In some embodiments, the prodrug modification polypeptide is herpes simplex virus thymidine kinase (HSV-tk) or an equivalent thereof. In some embodiments, the prodrug is selected from ganciclovir, penciclovir, acyclovir, valacyclovir, (E)-5-(2-bromovinyl)-2'-deoxyuridine (BVDU), zidovudine, 2'-exo-methanocarbathymidine, 5-fluorocytosine, 5-methylpurine deoxyriboside (MEP), fludarabine, cyclophosphamide, ifosfamide, acetaminophen, 4-ipomeanol, 4-[(2-chloroethyl)(2-mesyloxyethyl)amino]benzoyl-L-glutamic acid (CMDA), hydroxy-aniline mustards, amino-ainiline mustards, anthracycline glutamates, methotrexate α-peptides, irinotecan, anthracycline acetals, CB1954, SN23862, 4-nitrobenzyl carbamates, quinones, indole-3-acetic acid, 6-thioxanthine, HM1826, anthracycline acetals, 5'-deoxy-5-fluorouridine, selenomethionine, and an equivalent of each thereof. In some embodiments, the prodrug is ganciclovir or an equivalent thereof.

In some embodiments, the lineage-specific miRNA-binding polynucleotide further comprises (iii) a promoter operably linked to the lineage-specific miRNA binding site. In some embodiments, the promoter is a constitutive promoter. In some embodiments, the promoter is an inducible promoter. In some embodiments, the promoter is selected from promoters for each of elongation factor-1 alpha (EF1-α), cytomegalovirus (CMV), simian virus 40 (SV40), PGK1, ubiquitin C (Ubc), human beta actin, CAG, TRE, UAS, Ac5, polyhedron, CaMKIIa, GAL1, GAL10, TEF1, GDS, ADH1, CaMV35S, Ubi, H1, U6, and an equivalent of each thereof.

In some embodiments, the lineage-specific miRNA-binding polynucleotide further comprises (iv) a polynucleotide encoding a fluorescent protein, wherein the polynucleotide encoding the fluorescent protein is operably linked to the lineage-specific miRNA binding site. In some embodiments, the fluorescent protein is selected from green fluorescent protein (GFP), red fluorescent protein (RFP), cyan fluorescent protein (CFP), blue fluorescent protein (BFP), yellow fluorescent protein (YFP), orange fluorescent protein (OFP), far-red protein, near-IR protein, and an equivalent of each thereof. In some embodiments, the polynucleotide encoding the fluorescent protein and the polynucleotide encoding the prodrug modification polypeptide are linked by a polynucleotide selected from the group consisting of an internal ribosome entry site (IRES) element and a self-cleaving 2A peptide-encoding sequence.

In some embodiments, the lineage-specific miRNA corresponds to a cell lineage selected from pluripotent stem cells, tumors, liver cells, neural cells, endothelial cells, reduced pluripotent stem cells, (iPSC) and an equivalent of each thereof. In some embodiments, the lineage-specific miRNA binding site is capable of binding a polynucleotide selected from the group consisting of miR-21, miR-122, miR-124, miR-126, miR-302A, miR-1, miR-7, miR-9, miR-10, miR-96, miR-133, miR-137, miR-140, miR-143, miR-145, miR-181, miR-184, miR-199, miR-200, miR-203, miR-208a, miR-214, miR-218, miR-223, miR-338, miR-375, and miR-451.

In some embodiments, the mixed cell population is a teratoma. The mixed cell population and/or the teratoma can be in vitro or in vivo. Also provided are non-human animals comprising the mixed cell population and/or teratoma.

In some aspects, provided herein is a miRNA-binding polynucleotide comprising, or alternatively consisting essentially of, or yet further consisting of, a promoter; at least one lineage-specific miRNA binding site; and a polynucleotide encoding a prodrug modification polypeptide; wherein the lineage-specific miRNA binding site is capable of binding a lineage-specific miRNA. In some embodiments, the binding of the lineage-specific miRNA to the miRNA-binding site silences expression of the prodrug modification polypeptide.

In some embodiments, the prodrug modification polypeptide is capable of modifying a prodrug such that the prodrug is cytotoxic. In some embodiments, the prodrug modification polypeptide is selected from a viral tyrosine kinase, a bacterial cytosine deaminase, carboxypeptidase G2, purine nucleoside phosphorylase, nitroreductase, deoxycytidine kinase, cytochrome P450, a horseradish peroxidase, a guanine ribosyltransferase, a β-glucuronidase, a β-galactosidase, a thymidine phosphorylase, methionine-α,γ-lyase, and an equivalent of each thereof. In some embodiments, the prodrug modification polypeptide is herpes simplex virus thymidine kinase (HSV-tk) or an equivalent thereof. In some embodiments, the prodrug is selected from ganciclovir, penciclovir, acyclovir, valacyclovir, (E)-5-(2-bromovinyl)-2'-deoxyuridine (BVDU), zidovudine, 2'-exo-methanocarbathymidine, 5-fluorocytosine, 5-methylpurine deoxyriboside (MEP), fludarabine, cyclophosphamide, ifosfamide, acetaminophen, 4-ipomeanol, 4-[(2-chloroethyl)(2-mesyloxyethyl)amino]benzoyl-L-glutamic acid (CMDA), hydroxy-aniline mustards, amino-ainiline mustards, anthracycline glutamates, methotrexate α-peptides, irinotecan, anthracycline acetals, CB1954, SN23862, 4-nitrobenzyl carbamates, quinones, indole-3-acetic acid, 6-thioxanthine, HM1826, anthracycline acetals, 5'-deoxy-5-fluorouridine, selenomethionine, and an equivalent of each thereof. In some embodiments, the prodrug is ganciclovir or an equivalent thereof.

In some embodiments, the lineage-specific miRNA-binding polynucleotide further comprises (iii) a promoter operably linked to the lineage-specific miRNA binding site. In some embodiments, the promoter is a constitutive promoter. In some embodiments, the promoter is an inducible promoter. In some embodiments, the promoter is selected from promoters for each of elongation factor-1 alpha (EF1-α), cytomegalovirus (CMV), simian virus 40 (SV40), PGK1, ubiquitin C (Ubc), human beta actin, CAG, TRE, UAS, Ac5, polyhedron, CaMKIIa, GAL1, GAL10, TEF1, GDS, ADH1, CaMV35S, Ubi, H1, U6, and an equivalent of each thereof.

In some embodiments, the lineage-specific miRNA corresponds to a cell lineage selected from pluripotent stem cells, tumors, liver cells, neural cells, endothelial cells, induced pluripotent stem cells, and an equivalent of each thereof. In some embodiments, the lineage-specific miRNA binding site is capable of binding a polynucleotide selected from the group consisting of miR-21, miR-122, miR-124, miR-126, miR-302A miR-1, miR-7, miR-9, miR-10, miR-96, miR-133, miR-137, miR-140, miR-143, miR-145, miR-181, miR-184, miR-199, miR-200, miR-203, miR-208a, miR-214, miR-218, miR-223, miR-338, miR-375, and miR-451.

In some embodiments, the mixed cell population is a teratoma. The mixed cell population and/or the teratoma can be in vitro or in vivo.

In some aspects, provided herein is a vector comprising, or alternatively consisting essentially of, or yet further consisting of, the miRNA-binding polynucleotide described herein. In some embodiments, the vector is an adenoviral vector, an adenovirus associated vector, or a lentiviral vector. In some embodiments, the vector further comprises a polynucleotide encoding a selectable marker.

In some aspects, provided herein is a viral particle comprising, or alternatively consisting essentially of, or yet further consisting of, one or more of the miRNA-binding polynucleotide or the vector described herein.

In some aspects, provided herein is a method of producing a lineage-inducible mixed cell population comprising, or alternatively consisting essentially of, or yet further consisting of, (a) transducing a population of stem cells with the viral particle described herein, and (b) culturing the population of transduced stem cells in (a) under conditions suitable to produce a lineage-inducible mixed cell population. In some embodiments, the stem cells are embryonic stem cells, or induced pluripotent stem cells. In some embodiments, the lineage-inducible mixed cell population is a teratoma.

In some aspects, provided herein is a miRNA-binding polynucleotide comprising, or alternatively consisting essentially of, or yet further consisting of, a promoter comprising elongation factor-1 alpha (EF1-α), the promoter being operably linked to a polynucleotide construct comprising: a first lineage-specific miRNA binding site, a polynucleotide encoding herpes simplex virus thymidine kinase (HSV-tk), a polynucleotide encoding self-cleaving 2A peptide, a polynucleotide encoding green fluorescent protein (GFP), and a second lineage-specific miRNA binding site. In some embodiments, provided herein is a system comprising, or alternatively consisting essentially of, or yet further consisting of, the miRNA-binding polynucleotide, a stem cell population, and a prodrug. In some embodiments, the prodrug is cytotoxic when modified by the prodrug modification polypeptide.

In some aspects, provided herein is a method comprising, or alternatively consisting essentially of, or yet further consisting of, overexpressing in a stem cell population of one or more transcription factors capable of biasing differentiation of the stem cell population, and exposing the stem cell population to a growth medium, wherein the growth medium is compatible with biasing differentiation of the stem cell population, and wherein the stem cell population comprises either a teratoma, optionally derived from human pluripotent stem cells (hPSCs), induced pluripotent stem cells (iPSC) or an ex vivo tissue engineered construct.

In some embodiments, the transcription factor is ETV2, MYOD1 or NEUROD1. In some embodiments, the growth medium is an endothelial growth medium.

In some embodiments, the stem cell population comprises one or more transcription-factor overexpression polynucleotides comprising a promoter, the promoter being operably linked to a polynucleotide comprising a polynucleotide encoding the transcription factor capable of biasing differentiation of the stem cell population, a selection marker, and optionally, an internal ribosome entry site (IRES) element or a polynucleotide encoding self-cleaving 2A peptide. In some embodiments, the promoter is a constitutive promoter. In some embodiments, the promoter is an inducible promoter. In some embodiments, the promoter is selected from promoters for each of elongation factor-1 alpha (EF1-α), cytomegalovirus (CMV), simian virus 40 (SV40), PGK1, ubiquitin C (Ubc), human beta actin, CAG, TRE, UAS, Ac5, polyhedron, CaMKIIa, GAL1, GAL10, TEF1, GDS, ADH1, CaMV35S, Ubi, H1, U6, and an equivalent of each thereof.

In some embodiments, the the stem cell population comprises one or more transcription-factor overexpression polynucleotides comprising a polynucleotide encoding the transcription factor capable of biasing differentiation of the stem cell population, a selection marker, and optionally, an internal ribosome entry site (IRES) element or a polynucleotide encoding self-cleaving 2A peptide, wherein transcription of the transcription-factor overexpression polynucleotide is under control of an inducible system. In some embodiments, the inducible system is a doxycycline-induced gene expression system. In some embodiments, the doxycycline-induced gene expression system is Tet-On 3G.

In some embodiments, the stem cell population comprises an inactivated Cas protein lacking DNA endonuclease activity, a transcriptional activation domain operably linked to the inactivated Cas protein, and one or more CRISPR guide RNAs capable of binding to the inactivated Cas protein and capable of binding to endogenous genomic sites of the stem cell population so as to overexpress the transcription factors capable of biasing differentiation of the stem cell population.

In some embodiments, the stem cell population comprises an optically controlled overexpression protein complex comprising a first half of a photodimerisable protein, operably linked to an inactivated Cas protein lacking DNA endonuclease activity; a second half of a photodimerisable protein, operably linked to a transcriptional activation domain and capable of being operably linked to the first half of the photodimerisable protein through photodimerisation; and one or more CRISPR guide RNAs capable of binding to the inactivated Cas protein and capable of binding to endogenous genomic sites of the stem cell population so as to overexpress the transcription factors capable of biasing differentiation of the stem cell population when the first half and the second half of the photodimerisable protein are linked.

In some embodiments, the stem cell population comprises an optically controlled overexpression protein complex comprising a first half of a photodimerisable protein, operably linked to a first half of an inactivated Cas protein lacking DNA endonuclease activity; a second half of a photodimerisable protein, operably linked to molecule comprising a second half of an inactivated Cas protein lacking DNA endonuclease activity operably linked to a transcriptional activation domain, wherein the second half of the photodimerisable protein is capable of being operably linked to the first half of the photodimerisable protein through photodimerisation; and one or more CRISPR guide RNAs capable of binding to the inactivated Cas protein and capable of binding to endogenous genomic sites of the stem cell population so as to overexpress the transcription factors capable of biasing differentiation of the stem cell population when the first half and the second half of the photodimerisable protein are linked.

In some aspects, provided herein is one or more transcription-factor overexpression polynucleotides comprising, or alternatively consisting essentially of, or yet further consisting of, a promoter, the promoter being operably linked to a polynucleotide comprising a polynucleotide encoding a transcription factor capable of biasing differentiation of a stem cell population, a selection marker; and optionally, an internal ribosome entry site (IRES) element or a polynucleotide encoding self-cleaving 2A peptide.

In some aspects, provided herein is one or more transcription-factor overexpression polynucleotides comprising, or alternatively consisting essentially of, or yet further consisting of, a polynucleotide encoding a transcription factor capable of biasing differentiation of a stem cell population, a selection marker, and, optionally, an internal ribosome entry site (IRES) element or a polynucleotide encoding self-cleaving 2A peptide, wherein transcription of the transcription-factor overexpression polynucleotide is under control of an inducible system.

In some aspects, provided herein is a polypeptide encoded by the transcription-factor overexpression polynucleotides described herein.

In some aspects, provided herein is a system comprising, or alternatively consisting essentially of, or yet further consisting of, a stem cell population and one or more transcription-factor overexpression polynucleotides comprising a promoter, the promoter being operably linked to a polynucleotide comprising a polynucleotide encoding a transcription factor capable of biasing differentiation of a stem cell population, a selection marker, and, optionally, an internal ribosome entry site (IRES) element or a polynucleotide encoding self-cleaving 2A peptide.

In some aspects, provided herein is a system comprising, or alternatively consisting essentially of, or yet further consisting of, a stem cell population and one or more transcription-factor overexpression polynucleotides comprising a polynucleotide encoding a transcription factor capable of biasing differentiation of a stem cell population, a selection marker, and, optionally, an internal ribosome entry site (IRES) element or a polynucleotide encoding self-cleaving 2A peptide, wherein transcription of the transcription-factor overexpression polynucleotide is under control of an inducible system.

In some aspects, provided herein is a system comprising, or alternatively consisting essentially of, or yet further consisting of, a stem cell population, an inactivated Cas protein lacking DNA endonuclease activity, a transcriptional activation domain operably linked to the inactivated Cas protein, and at least one CRISPR guide RNA capable of binding to the inactivated Cas protein and capable of binding to an endogenous genomic site of the stem cell population so as to overexpress at least one transcription factor capable of biasing differentiation of the stem cell population.

In some aspects, provided herein is a system comprising, or alternatively consisting essentially of, or yet further consisting of, a stem cell population and an optically controlled overexpression protein complex comprising a first half of a photodimerisable protein, operably linked to an inactivated Cas protein lacking DNA endonuclease activity, a second half of a photodimerisable protein, operably linked to a transcriptional activation domain and capable of being operably linked to the first half of the photodimerisable protein through photodimerisation, and at least one CRISPR guide RNA capable of binding to the inactivated Cas protein and capable of binding to an endogenous genomic site of the stem cell population so as to overexpress at least one transcription factor capable of biasing differentiation of the stem cell population when the first half and the second half of the photodimerisable protein are linked.

In some aspects, provided herein is a system comprising, or alternatively consisting essentially of, or yet further consisting of, a stem cell population and an optically controlled overexpression protein complex comprising a first half of a photodimerisable protein, operably linked to a first half of an inactivated Cas protein lacking DNA endonuclease activity, a second half of a photodimerisable protein, operably linked to molecule comprising a second half of an inactivated Cas protein lacking DNA endonuclease activity operably linked to a transcriptional activation domain, wherein the second half of the photodimerisable protein is capable of being operably linked to the first half of the photodimerisable protein through photodimerisation, and at least one CRISPR guide RNA capable of binding to the inactivated Cas protein and capable of binding to an endogenous genomic site of the stem cell population so as to overexpress at least one transcription factor capable of biasing differentiation of the stem cell population when the first half and the second half of the photodimerisable protein are linked.

In some aspects, provided herein is an optically controlled overexpression system comprising, or alternatively consisting essentially of, or yet further consisting of, a first half of a photodimerisable protein, operably linked to an inactivated Cas protein lacking DNA endonuclease activity, a second half of a photodimerisable protein, operably linked to a transcriptional activation domain and capable of being operably linked to the first half of the photodimerisable protein through photodimerisation, and at least one CRISPR guide RNA capable of binding to the inactivated Cas protein and capable of binding to an endogenous genomic site of the stem cell population so as to overexpress at least one transcription factor capable of biasing differentiation of the stem cell population when the first half and the second half of the photodimerisable protein are linked.

In some aspects, provided herein is an optically controlled overexpression system comprising, or alternatively consisting essentially of, or yet further consisting of, a first half of a photodimerisable protein, operably linked to a first half of an inactivated Cas protein lacking DNA endonuclease activity, a second half of a photodimerisable protein, operably linked to molecule comprising a second half of an inactivated Cas protein lacking DNA endonuclease activity operably linked to a transcriptional activation domain, wherein the second half of the photodimerisable protein is capable of being operably linked to the first half of the photodimerisable protein through photodimerisation, and at least one CRISPR guide RNA capable of binding to the inactivated Cas protein and capable of binding to an endogenous genomic site of the stem cell population so as to overexpress at least one transcription factor capable of biasing differentiation of the stem cell population when the first half and the second half of the photodimerisable protein are linked.

In some aspects, provided herein is an overexpression system comprising, or alternatively consisting essentially of, or yet further consisting of, an inactivated Cas protein lacking DNA endonuclease activity, a transcriptional activation domain operably linked to the inactivated Cas protein, and at least one CRISPR guide RNA capable of binding to the inactivated Cas protein and capable of binding to an endogenous genomic site of the stem cell population so as to overexpress a transcription factor capable of biasing differentiation of a stem cell population.

In some aspects, the photodimerisable protein is derived from the CRY2-CIB1 system.

In some aspects, provided herein is a method comprising, or alternatively consisting essentially of, or yet further consisting of, one or more of the steps, in any order, of one or more of the steps, in any order, of (a) administering a prodrug to a mixed cell population comprising a lineage-specific miRNA-binding polynucleotide, wherein the lineage-specific miRNA-binding polynucleotide comprises a lineage-specific miRNA binding site operably linked to a polynucleotide encoding a prodrug modification polypeptide and wherein the mixed cell population comprises at least one cell type that expresses a lineage-specific miRNA that binds to the lineage-specific miRNA binding site; and (b) overexpressing in the mixed cell population a transcription factor capable of biasing differentiation of the mixed cell population and exposing the mixed cell population to a growth medium, wherein the growth medium is compatible with biasing differentiation of the mixed cell population.

In some embodiments, binding of the lineage-specific miRNA to the miRNA-binding site silences expression of the prodrug modification polypeptide.

In some embodiments, the prodrug is cytotoxic when modified by the prodrug modification polypeptide. In some embodiments, the prodrug modification polypeptide is selected from a viral tyrosine kinase, a bacterial cytosine deaminase, carboxypeptidase G2, purine nucleoside phosphorylase, nitroreductase, deoxycytidine kinase, cytochrome P450, a horseradish peroxidase, a guanine ribosyltransferase, a β-glucuronidase, a β-galactosidase, a thymidine phosphorylase, methionine-α,γ-lyase, and an equivalent of each thereof. In some embodiments, the prodrug modification polypeptide is herpes simplex virus thymidine kinase (HSV-tk), or an equivalent thereof. In some embodiments, the prodrug is selected from ganciclovir, penciclovir, acyclovir, valacyclovir, (E)-5-(2-bromovinyl)-2'-deoxyuridine (BVDU), zidovudine, 2'-exo-methanocarbathymidine, 5-fluorocytosine, 5-methylpurine deoxyriboside (MEP), fludarabine, cyclophosphamide, ifosfamide, acetaminophen, 4-ipomeanol, 4-[(2-chloroethyl)(2-mesyloxyethyl)amino]benzoyl-L-glutamic acid (CMDA), hydroxy-aniline mustards, amino-ainiline mustards, anthracycline glutamates, methotrexate α-peptides, irinotecan, anthracycline acetals, CB1954, SN23862, 4-nitrobenzyl carbamates, quinones, indole-3-acetic acid, 6-thioxanthine, HM1826, anthracycline acetals, 5'-deoxy-5-fluorouridine, selenomethionine, and an equivalent of each thereof. In some embodiments, the prodrug is ganciclovir or an equivalent thereof.

In some embodiments, the mixed cell population is a teratoma. The mixed cell population and/or the teratoma can be in vitro or in vivo. Also provided are non-human animals comprising the mixed cell population and/or teratoma.

In some embodiments, the lineage-specific miRNA-binding polynucleotide further comprises a promoter operably linked to the lineage-specific miRNA binding site. In some embodiments, the promoter is a constitutive promoter. In some embodiments, the promoter is an inducible promoter. In some embodiments, the promoter is selected from promoters for each of elongation factor-1 alpha (EF1-α), cytomegalovirus (CMV), simian virus 40 (SV40), PGK1, ubiquitin C (Ubc), human beta actin, CAG, TRE, UAS, Ac5, polyhedron, CaMKIIa, GAL1, GAL10, TEF1, GDS, ADH1, CaMV35S, Ubi, H1, U6, and an equivalent of each thereof.

In some embodiments, the lineage-specific miRNA-binding polynucleotide further comprises a polynucleotide encoding a fluorescent protein, wherein the polynucleotide encoding the fluorescent protein is operably linked to the lineage-specific miRNA binding site. In some embodiments, the fluorescent protein is selected from green fluorescent protein (GFP), red fluorescent protein (RFP), cyan fluorescent protein (CFP), blue fluorescent protein (BFP), yellow fluorescent protein (YFP), orange fluorescent protein (OFP), far-red protein, near-IR protein, and an equivalent of each thereof. In some embodiments, the polynucleotide encoding the fluorescent protein and the polynucleotide encoding the prodrug modification polypeptide are linked by a polynucleotide selected from the group consisting of an internal ribosome entry site (IRES) element and a self-cleaving 2A peptide-encoding sequence.

In some embodiments, the lineage-specific miRNA corresponds to a cell lineage selected from pluripotent stem cells, iPSCs, tumors, liver cells, neural cells, endothelial cells, pluripotent stem cells, and an equivalent of each thereof. In some embodiments, the lineage-specific miRNA binding site is capable of binding a polynucleotide selected from the group consisting of miR-21, miR-122, miR-124, miR-126, miR-302A miR-1, miR-7, miR-9, miR-10, miR-96, miR-133, miR-137, miR-140, miR-143, miR-145, miR-181, miR-184, miR-199, miR-200, miR-203, miR-208a, miR-214, miR-218, miR-223, miR-338, miR-375, and miR-451.

In some aspects, provided herein is a method comprising, or alternatively consisting essentially of, or yet further consisting of, the steps of (a)(i) transducing a stem cell population with the viral particle described herein, or more polynucleotides encoding one or more transcription factors, and/or miRNA, and (ii) culturing the population of transduced stem cells in (a)(i) under conditions suitable to produce a lineage-inducible mixed cell population; and (b) overexpressing in the stem cell population at least one transcription factor capable of biasing differentiation of the stem cell population; and exposing the stem cell population to a growth medium, wherein the growth medium is compatible with biasing differentiation of the stem cell population. The stem cell can be an embryonic stem cell, an iPSC, or an adult or somatic stem cell.

In some embodiments, the stem cell population is a teratoma.

In some embodiments, the transcription factor is ETV2, MYOD1 or NEUROD1, or an equivalent thereof.

In some embodiments, the growth medium is an endothelial growth medium or an equivalent thereof.

In some embodiments, the stem cell or mixed cell population comprises one or more transcription-factor overexpression polynucleotides comprising a promoter, the promoter being operably linked to a polynucleotide comprising a polynucleotide encoding the transcription factor capable of biasing differentiation of the mixed cell population, a selection marker, and, optionally, an internal ribosome entry site (IRES) element or a polynucleotide encoding self-cleaving 2A peptide. In some embodiments, the promoter is a constitutive promoter. In some embodiments, the promoter is an inducible promoter. In some embodiments, the promoter is selected from promoters for each of elongation factor-1 alpha (EF1-α), cytomegalovirus (CMV), simian virus 40 (SV40), PGK1, ubiquitin C (Ubc), human beta actin, CAG, TRE, UAS, Ac5, polyhedron, CaMKIIa, GAL1, GAL10, TEF1, GDS, ADH1, CaMV35S, Ubi, H1, U6, and an equivalent of each thereof.

In some embodiments, the stem cell or mixed cell population comprises one or more transcription-factor overexpression polynucleotides comprising a polynucleotide encoding the transcription factor capable of biasing differentiation of the mixed cell population, a selection marker, and, optionally, an internal ribosome entry site (IRES) element or a polynucleotide encoding self-cleaving 2A peptide, wherein transcription of the transcription-factor overexpression polynucleotide is under control of an inducible system. In some embodiments, the inducible system is a doxycycline-induced gene expression system. In some embodiments, the doxycycline-induced gene expression system is Tet-On 3G.

In some embodiments, the stem cell or mixed cell population comprises an inactivated Cas protein lacking DNA endonuclease activity, a transcriptional activation domain operably linked to the inactivated Cas protein, and at least one CRISPR guide RNA capable of binding to the inactivated Cas protein and capable of binding to an endogenous genomic site of the mixed cell population so as to overexpress the transcription factor capable of biasing differentiation of the mixed cell population.

In some embodiments, the stem cell or mixed cell population comprises an optically controlled overexpression protein complex comprising a first half of a photodimerisable protein, operably linked to an inactivated Cas protein lacking DNA endonuclease activity, a second half of a photodimerisable protein, operably linked to a transcriptional activation domain and capable of being operably linked to the first half of the photodimerisable protein through photodimerisation, and at least one CRISPR guide RNA capable of binding to the inactivated Cas protein and capable of binding to an endogenous genomic site of the mixed cell population so as to overexpress the transcription factor capable of biasing differentiation of the mixed cell population when the first half and the second half of the photodimerisable protein are linked.

In some embodiments, the stem cell or mixed cell population comprises an optically controlled overexpression protein complex comprising a first half of a photodimerisable protein, operably linked to a first half of an inactivated Cas protein lacking DNA endonuclease activity, a second half of a photodimerisable protein, operably linked to molecule comprising a second half of an inactivated Cas protein lacking DNA endonuclease activity operably linked to a transcriptional activation domain, wherein the second half of the photodimerisable protein is capable of being operably linked to the first half of the photodimerisable protein through photodimerisation, and CRISPR guide RNA capable of binding to the inactivated Cas protein and capable of binding to an endogenous genomic site of the stem cell population so as to overexpress the transcription factor capable of biasing differentiation of the mixed cell population when the first half and the second half of the photodimerisable protein are linked.

In some embodiments, the teratoma is derived from human pluripotent stem cells (hPSCs) or human induced pluripotent stem cells (iPSCs).

In some embodiments, the mixed cell or stem cell population comprises an ex vivo tissue engineered construct.

In some aspects, provided herein is a cell population obtained using any of the methods or systems described herein.

In some aspects, provided herein is a cell or a cell population comprising any of the miRNA-binding polynucleotides, transcription-factor overexpression polynucleotides, optically controlled overexpression systems, overexpression systems, vectors, or viral particles described herein.

The methods as described herein can further comprise combining the mixed cell population with an effective amount of a scaffold matrix that encapsulates the mixed cell population, and optionally comprises one or more hollow lumens allowing for perfusion. Non-limiting examples of scaffold materials include a biological polymer, a hydrogel, polyethylene glycol, hyaluronic acid, alginate, collagen, gelatin, fibrin, Matrigel® (a solubilized basement membrane preparation), gelatin methacrylate hyaluronic acid methacrylate, poly (vinyl alcohol), a blend of alginate/Pluronic™ F127 (a nonionic, surfactant polyol), Pluronic™ F127, and blends of alginate/Pluronic™ F127. In one aspect, the scaffold comprises from about 5 to about 15 mg/mL gelatin, from about 1 to 7 mg/mL Matrigel®, and from about 5 to about 10 mg/mL fibrin.

In a further aspect, the method further comprises liquefying or evacuating the scaffold matrix and depositing the mixed cell population into a perfusion chamber or bioorganic printer for 3D printing.

Also provided are mixed cell populations prepared by these methods.

BRIEF DESCRIPTION OF THE DRAWINGS

(FIG. 1A) Schematic of miRNA-HSV-tk-GFP construct. 2A is gene encoding for a self-cleaving peptide. Upon transcription of construct it will silenced if appropriate endogenously expressed miRNA is present in the cell. (FIG. 1B) Schematic of how developing teratoma should form in the presence of Ganciclovir (GCV, 80 mg/kg/d) if cells were transduced with miRNA-HSV-tk construct. (FIG. 1C) Phase images from light microscopy showing H1 cell survival after 3 and 5 days in the presence of GCV (10 µM). H1 ESC line was either transduced with GFP control (EGIP backbone) or miR-124-HSV-tk-GFP. (FIG. 1D) Fluorescent microscopy and phase images showing HEK293T and HeLA cells transduced with either No GFP control, HSV-tk-GFP, or miR-21-HSV-tk-GFP. (FIG. 1E) Quantification of (FIG. 1D) using flow cytometry and gating based on the presence or absence of GFP. (FIG. 1F) In vivo studies of miR-124-HSV-tk-GFP teratomas in the presence of GCV administration (80 mg/kg/d) showing cell type fraction log fold-change based on different cell types with accompanying Z-scores compared to miR-124-HSV-tk-GFP teratomas in the absence of GCV.

(FIG. 2A) Schematic of Molecular Sculpting. Schematic (FIG. 2B) PSCs transduced with single/multiple miRNA circuit(s) and/or TF overexpression vectors. (FIGS. 2C-2D) Growth, differentiation, and maturation of cells into desired human tissue via self-organization, miRNA circuit+GCV administration, and/or TF overexpression in an (FIG. 2C) in vivo or (FIG. 2D) ex vivo context. (FIG. 2E) Derived vascularized human tissue. (FIG. 2F) Tissue transplant into host.

(FIG. 6A) Overexpression vector design; (FIG. 6B) Morphology change of ETV2-overexpressing cells vs control mCherry expressing cells in endothelial growth medium; (FIG. 6C) CDH5 staining of ETV2-reprogrammed cells vs mCherry expressing control cells and primary human umbilical vein endothelial cells (HUVEC); (FIG. 6D) qPCR validation of endothelial marker upregulation in ETV2-reprogrammed cells; (FIG. 6E) Functional validation of endothelial-like behavior by tube formation assay.

(FIG. 8A) Schematic of the LACE light-inducible gene expression system; (FIG. 8B) Demonstration using a GFP reporter induced by the LACE system, showing increased GFP signal upon optical stimulation for up to 48 hrs, shown by imaging and image histogram data; (FIG. 8C) Schematic of the Magnet light-inducible geneexpression system; (FIG. 8D) Demonstration using a GFP reporter induced by the Magnet system, showing increased GFP signal upon optical stimulation for up to 24 hrs, shown by imaging and image histogram data.

(FIG. 9A) Schematic of general workflow. Subcutaneous injection of H1 PSCs in a slurry of Matrigel® and embryonic stem cell medium was made in the right flank of Rag2$^{-/-}$;γc$^{-/-}$ immunodeficient mice. Weekly monitoring of teratoma growth was quantified by approximating elliptical area (mm$^2$). Tumors were then extracted after 8-10 wks of growth and observed for external heterogeneity before small sections were frozen for H&E staining. Remaining tumor dissociated into a single cell suspension via standard GentleMACS protocols. Single cell suspension used for scRNA-seq (10× Genomics). (FIG. 9B) Growth kinetics of four H1 teratomas. (FIG. 9D) Images of four teratomas generated from H1 cells. (FIG. 9C) H&E stains of the four teratoma histology sections. The presence of ectoderm, mesoderm, and endoderm confirmed for pluripotency and developmental potential. (FIG. 9E) UMAP visualization of cell types identified from single cell RNA-sequencing of the four H1 teratomas combined with three additional H1 teratomas with individual cells barcoded with lentiviruses.

(FIG. 10A) Heatmap of top marker genes for each cell type. (FIG. 10B) Distribution of cell types represented in each individual teratoma (FIG. 10C) Distribution of germ layer representation in each individual teratoma compared to zebrafish. (FIG. 10D) H1 cells were uniquely barcoded at low MOI with lentiviral vectors before teratoma formation. The barcodes were counted and assessed for lineage/cell type priming of cells. (FIG. 10E) Fraction of barcodes retained after teratoma formation. (FIG. 10F) Cell type enrichment was computed for each lentiviral barcode with at least 15 cells detected in the scRNA-seq data. (FIG. 10G) Cell type variance across teratomas vs cell type bias across lentiviral barcodes.

(FIG. 11A) PGP1-Cas9 iPSCs were induced with a CRISPR library targeting a panel of 24 key developmental genes with 2 gRNAs per gene. After teratoma formation, scRNA-seq was used to identify shifts in cell type formation as a result of gene knockouts. (FIG. 11B) Average effect of gene knockout on cell type enrichment/depletion versus the correlation of cell type enrichment for the gRNAs. Error bars represent bootstrap standard deviation (Methods) Genes in the top right quadrant were selected for further analysis. (FIG. 11C) Average effect of gene knockout on cell type enrichment/depletion versus average editing rate for guide RNAs targeting that gene. (FIG. 11D) Effect size (regression coefficient) of gene knockout enrichment for cell types and germ layers.

FIGS. 12A-12B: TF overexpression and inducible hES lines. (FIG. 12A) Construct design of dox-inducible TF overexpression vector between piggyBac transposon inverted terminal repeats. (FIG. 12B) Generation of clonal inducible overexpression hES lines.

FIG. 13: Schematic of printed tissue construct capable of long-term ex vivo perfusion.

(FIG. 15A) Schematic demonstrating the experimental workflow for ex vivo vascular-organoid coupling. A mixture of Human Umbilical Vein Cord Endothelial Cells (HUVECs) and Mesenchymal Stem Cells (MSCs) in a fibrin gel are combined with an organoid and cast into a perfusion chamber. (FIG. 15B) Preliminary experiment depicting perfusable, self-organized vasculature in a fibrin gel cocultured with an organoid. Arrows point to vasculature that is perfused with media containing FITC labelled dextran. Bottom arrow shows signs of vascular-organoid coupling.

(FIG. 16G) Mesenchyme (FIG. 16H) Bone (FIG. 16I) Developing cardiac muscle/skeletal muscle (FIG. 16J) Blood bessel (FIG. 16K) Squamous epithelium (skin) (FIG. 16L) Human cell type abundances in the H1 teratomas. (FIG. 16M) UMAP plot of mouse cell types in the H1 teratomas.

(FIG. 17A) HUES62, PGP1, H9, and H1 cell lines were mixed in equal ratios and injected to create chimeric teratomas. (FIG. 17B) Proportion of cells profiled with scRNA-seq belonging to each cell line. (FIG. 17C) UMAP plot of transcriptome profiles from cells isolated from chimeric teratomas. (FIG. 17D) Cell line identities overlaid on UMAP plots.

(FIG. 18A) Average expression of teratoma cell types was correlated with fetal cell types from different stages of development. Fetal single cell transcriptomes from the appropriate stage were projected onto SWNE embeddings of teratoma cells, and correlation of key markers was assessed. (FIG. 18B) Cosine similarity of teratoma brain cells with fetal brain cells of different ages. (FIG. 18C) Key marker gene correlation across Radial Glia, Intermediate Neuronal Progenitors, and Early Neurons. (FIG. 18D) Projection of fetal brain cell types onto a teratoma neural SWNE embedding. (FIG. 18E) Fraction of brain related cell types in the teratoma and fetal brain. (FIG. 18F) H&E stain (left) and RNAScope image (right) of HESS (radial glia marker) expression. DAPI is a nuclear stain. 4-10 punctate dots/cell is a positive result.

(FIG. 19A) Cosine similarity of teratoma gut cells with fetal gut cells of different ages (FIG. 19B) Key marker gene correlation across mid/hindgut and foregut. (FIG. 19C) Projection of fetal gut cell types onto a teratoma gut SWNE embedding. (FIG. 19D) Proportion of foregut and mid/hindgut cells in the teratoma and fetal gut. (FIG. 19E) H&E stain as well as FOXJ1 staining of ciliated respiratory epithelium. (FIG. 19F) Positive (left) and negative (right) RNAScope® control staining. DAPI is a nuclear stain. 4-10 punctate dots/cell is a positive result.

(FIG. 20A) UMAP projection of PGP1 cell types classified using the H1 cell types as a reference. (FIG. 20B—FIG. 20C) Scatterplot of individual guide RNA effects on cell type abundance for (FIG. 20B) CDX2 and (FIG. 20C) TWIST1. (FIG. 20D) Cells per gRNA and cells per gene for the screen.

(FIG. 21A) Lentiviral barcode construct map (FIG. 21B) Left: the normalized proportion of each teratoma in every cell type. Right: the coefficient of variance for every cell type across the 7 H1 teratomas.

(FIG. 22A) Phase images from light microscopy showing HEK293T cell survival after 3 days in the presence of GCV (1004, 100 µM). HEK293T line was either transduced with GFP control (EGIP backbone) or miR-122-HSV-tk-GFP. (FIG. 22B) Fluorescent microscopy and phase images showing HEK293T and HUVECs transduced with either No GFP control, HSV-tk-GFP, or miR-126-HSV-tk-GFP. (FIG. 22C) Quantification of (FIG. 22B) using flow cytometry and gating based on the presence or absence of GFP. (FIG. 22D) Images of teratomas grown in the absence and presence of GCV administration (80 mg/kg/d) for 10 weeks.

(FIG. 23A) ETV2 Validation: Endothelial-like cells differentiated by ETV2 overexpression were validated by gene expression analysis, immunofluorescence, and functional testing—tube formation assay. (FIG. 23B) NEUROD1 Validation: Neurons differentiated by NEUROD1 overexpression were validated by gene expression analysis and immunofluorescence. (FIG. 23C) MYOD1 Validation: Skeletal muscle cells differentiated by MYOD1 overexpression examined by morphology and immunofluorescence.

(FIG. 24A) Image of printed tissue construct capable of long-term ex vivo perfusion. (FIG. 24B) Widefield microscopy image of GFP-labeled induced pluripotent stem cell masses grown within a printed construct. Scalebar: 1.5 mm.

DETAILED DESCRIPTION

Figures 1A, 1B, 1C, 1D, 1E, 1F:
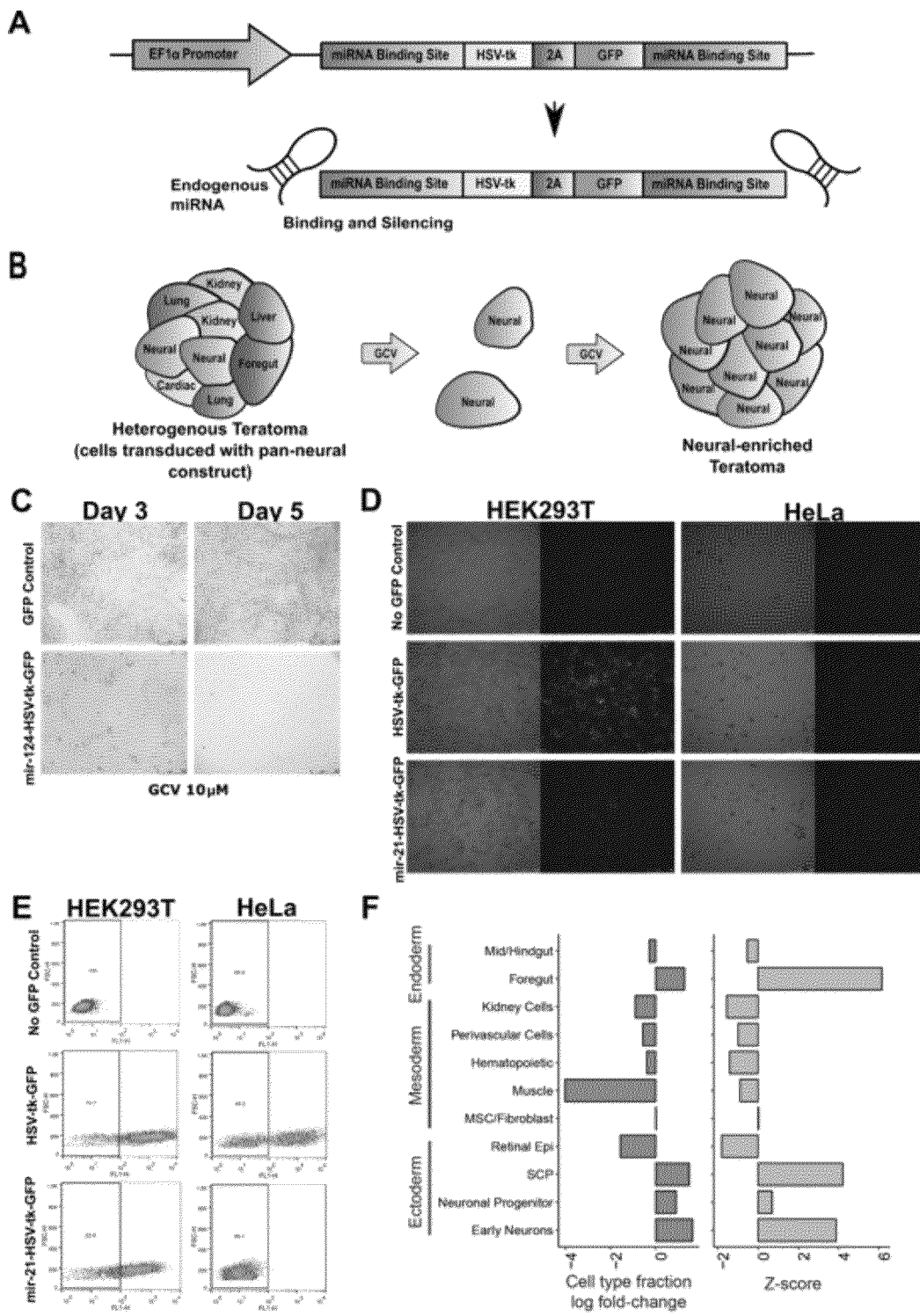
FIGS. 1A-1F: Molecular Sculpting of the Teratoma through miRNAs.

Embodiments according to the present disclosure will be described more fully hereinafter. Aspects of the disclosure may, however, be embodied in different forms and should not be construed as limited to the embodiments set forth herein. Rather, these embodiments are provided so that this disclosure will be thorough and complete, and will fully convey the scope of the invention to those skilled in the art. The terminology used in the description herein is for the purpose of describing particular embodiments only and is not intended to be limiting.

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

Throughout and within this application technical and patent literature are referenced by a citation. For certain of these references, the identifying citation is found at the end of this application immediately preceding the claims. All publications are incorporated by reference into the present disclosure to more fully describe the state of the art to which this disclosure pertains.

The terminology used in the description herein is for the purpose of describing particular embodiments only and is not intended to be limiting of the invention. All publications, patent applications, patents and other references mentioned herein are incorporated by reference in their entirety.

The practice of the present disclosure will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, $3^{rd}$ edition (Cold Spring Harbor Laboratory Press (2002)); Sohail (ed.) (2004) Gene Silencing by RNA Interference: Technology and Application (CRC Press). Gibson assembly, a molecular cloning method which allows for the joining of multiple DNA fragments in a single, isothermal reaction is widely known in the art and has been described by Gibson, D. G. et al. (2009), Nature Methods 6: 343-45. See also addgene.org/protocols/gibson-assembly/.

All numerical designations, e.g., pH, temperature, time, concentration, and molecular weight, including ranges, are approximations which are varied (+) or (−) by increments of 0.1 or 1.0, where appropriate, or alternatively by a variation of +/−15%, or alternatively 10%, or alternatively 5%, or alternatively 2%. It is to be understood, although not always explicitly stated that all numerical designations are preceded by the term "about." It also is to be understood, although not always explicitly stated, that the reagents described herein are merely exemplary and that equivalents of such are known in the art.

Definitions

As used in the specification and claims, the singular form "a", "an" and "the" include plural references unless the context clearly dictates otherwise. For example, the term "a cell" includes a plurality of cells, including mixtures thereof.

As used herein, the "administration" of an agent (e.g., a fusion RNA, viral particle, vector, polynucleotide, cell, population of cells, composition, or pharmaceutical composition) to a subject includes any route of introducing or delivering to a subject the agent to perform its intended function. Administration can be carried out by any suitable route, including orally, intranasally, intraocularly, ophthalmically, parenterally (intravenously, intramuscularly, intraperitoneally, or subcutaneously), or topically. Administration includes self-administration and the administration by another.

The term "cell" as used herein refers to a prokaryotic or eukaryotic cell. In some embodiments, the cell is a eukaryotic cell, optionally obtained from a subject or a commercially available source. In some embodiments, the cell is an isolated cell.

As used herein, the term "comprising" is intended to mean that the compositions and methods include the recited elements, but do not exclude others. As used herein, the transitional phrase "consisting essentially of" (and grammatical variants) is to be interpreted as encompassing the recited materials or steps "and those that do not materially affect the basic and novel characteristic(s)" of the recited embodiment. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising." "Consisting of" shall mean excluding more than trace elements of other ingredients and substantial method steps for administering the compositions disclosed herein. Aspects defined by each of these transition terms are within the scope of the present disclosure.

As used herein, the term "CRISPR" refers to Clustered Regularly Interspaced Short Palindromic Repeats (CRISPR). CRISPR may also refer to a technique or system of sequence-specific genetic manipulation relying on the CRISPR pathway. A CRISPR recombinant expression system can be programmed to cleave a target polynucleotide using a CRISPR endonuclease and a guideRNA or a combination of a crRNA and a tracrRNA. A CRISPR system can be used to cause double stranded or single stranded breaks in a target polynucleotide such as DNA or RNA. A CRISPR system can also be used to recruit proteins or label a target polynucleotide. In some aspects, CRISPR-mediated gene editing utilizes the pathways of nonhomologous end-joining (NHEJ) or homologous recombination to perform the edits. These applications of CRISPR technology are known and widely practiced in the art. See, e.g., U.S. Pat. No. 8,697,359 and Hsu et al. (2014) Cell 156(6): 1262-1278.

The term "guide RNA" as used herein refers to the guide RNA sequences used to target specific genes for correction employing the CRISPR technique. Techniques of designing gRNAs and donor therapeutic polynucleotides for target specificity are well known in the art. For example, Doench, J., et al. *Nature Biotechnology* 2014; 32(12):1262-7, Mohr, S. et al. (2016)*FEBS Journal* 283: 3232-38, and Graham, D., et al. *Genome Biol.* 2015; 16: 260. Guide RNA comprises or alternatively consists essentially of, or yet further consists of a fusion polynucleotide comprising CRISPR RNA (crRNA) and trans-activating CRIPSPR RNA (tracrRNA); or a polynucleotide comprising CRISPR RNA (crRNA) and transactivating CRIPSPR RNA (tracrRNA). In some aspects, a gRNA is synthetic (Kelley, M. et al. (2016) *J. of Biotechnology* 233 (2016) 74-83). As used herein, a biological equivalent of a gRNA includes but is not limited to polynucleotides or targeting molecules that can guide a Cas9 or equivalent thereof to a specific nucleotide sequence such as a specific region of a cell's genome.

Expression of CRISPR in cells can be achieved using conventional CRISPR/Cas systems and guide RNAs specific to the target genes in the cells. Suitable expression systems, e.g. lentiviral or adenoviral expression systems are known in the art. It is further appreciated that a CRISPR editing construct may be useful in binding to an endogenous nucleic acid, knocking out an endogenous nucleic acid, or knocking in a nucleic acid. Accordingly, it is appreciated that a CRISPR system can be designed for to accomplish one or both of these purposes.

The term "Cas protein" refers to a CRISPR-associated, RNA-guided endonuclease such as *Streptococcus pyogenes* Cas9 (spCas9) and orthologs and biological equivalents thereof. Biological equivalents of Cas9 include but are not limited to Type VI CRISPR systems, such as Cas13a, C2c2, and Cas13b, which target RNA rather than DNA. A Cas protein refers to an endonuclease that causes breaks or nicks in RNA as well as other variations such as dead Cas9 or dCas9, which lack endonuclease activity. In particular embodiments, the Cas protein is modified to eliminate endonuclease activity (referred to herein as "inactivated Cas protein"). For example, both RuvC and HNH nuclease domains can be rendered inactive by point mutations (e.g., D10A and H840A in SpCas9), resulting in a nuclease dead Cas9 (dCas9) molecule that cannot cleave target DNA. The dCas9 molecule retains the ability to bind to target RNA based on the guide RNA targeting sequence. A Cas protein can also refer to a "split" protein in which the protein is split into two halves (e.g., C-Cas9 and N-Cas9) and fused with two intein moieties. See, e.g., U.S. Pat. No. 9,074,199 B 1; Zetsche et al. (2015) Nat Biotechnol. 33(2):139-42; Wright et al. (2015) PNAS 112(10) 2984-89.

As used herein the terms "culture media" and "culture medium" are used interchangeably and refer to a solid or a liquid substance used to support the growth of cells (e.g., stem cells). Preferably, the culture media as used herein refers to a liquid substance capable of maintaining stem cells in an undifferentiated state. The culture media can be a water-based media which includes a combination of ingredients such as salts, nutrients, minerals, vitamins, amino acids, nucleic acids, proteins such as cytokines, growth factors and hormones, all of which are needed for cell proliferation and are capable of maintaining stem cells in an undifferentiated state. For example, a culture media can be a synthetic culture media such as, for example, minimum essential media α (MEM-α) (HyClone Thermo Scientific, Waltham, Mass., USA), DMEM/F12, GlutaMAX (Life Technologies, Carlsbad, Calif., USA), Neurobasal Medium (Life Technologies, Carlsbad, Calif., USA), KO-DMEM (Life Technologies, Carlsbad, Calif., USA), DMEM/F12 (Life Technologies, Carlsbad, Calif., USA), supplemented with the necessary additives as is further described herein. In some embodiments, the cell culture media can be a mixture of culture media. Preferably, all ingredients included in the culture media of the present disclosure are substantially pure and tissue culture grade. "Conditioned medium" and "conditioned culture medium" are used interchangeably and refer to culture medium that cells have been cultured in for a period of time and wherein the cells release/secrete components (e.g., proteins, cytokines, chemicals, etc.) into the medium.

The term "lineage-specific miRNA" as used herein refers to an miRNA that is unique or enriched in a particular cell type, cell lineage, or disease state. Certain types of cells express certain miRNAs for the purpose of RNA silenceing and post-transcriptional regulation of gene expression, guiding cell phenotypes. The term "lineage-specific miRNA binding polynucleotide" as used herein refers to a polynucleotide that is capable of hybridizing with a lineage-specific miRNA, for example by having a complementary nucleotide sequence. The term "lineage-specific miRNA binding site" as used herein refers the portion of the lineage-specific miRNA binding polynucleotide that hybridizes with the lineage-specific miRNA.

The term "prodrug" as used herein refers to a compound that must undergo chemical modification, optionally by metabolic processes or enzymatic catalysis, before becoming an active pharmacological agent. The term "prodrug modification polypeptide" as used herein refers to a protein, enzyme, polypeptide, or any biological catalyst that chemically modifies a particular prodrug. In some embodiments, prodrugs include compounds that are cytotoxic upon modification. For instance, ganciclovir is a prodrug that can be functionally phosphorylated by a kinase, such as herpes simplex virus thymidine kinase (HSV-tk) to yield phosphorylated ganciclovir, a cytotoxic guanosine analog. The use of prodrugs paired with prodrug modification peptides is well-known in the art. See, e.g., Denny, W. A. (2003) J. Biomed. Biotechnol. 2003:1, 48-70.

The term "modification" and "modified" as used herein in reference to a prodrug refers to a chemical modification— that is, the making or breaking of one or more chemical bonds in the prodrug. For example, modifications can include phosphorylation, oxidation, reduction, substitution, acylation, cleavage, rearrangement, sulfonylation, nitration, halogenation, protonation, condensation, hydrolysis, or the reverse of each. In particular, ganciclovir is rendered cytotoxic upon phosphorylation by a thymidine kinase.

The term "photodimerisable protein" as used herein refers a protein or other polypeptide that may exist as two sub-units that may be joined by the formation of one or more chemical bonds, hydrogen bonds, or other binding interactions through light-mediated photodimerisation. Examples in the literature demonstrate that a skilled artisan may use a photodimerisable protein fused to other polypeptide components in order to prepare a polypeptide that may be activated upon such dimerization. See, e.g., Taslimi, A. et al. (2016) *Nat. Chem. Biol.* 12(6): 425-30. For instance, the CRY2-CIB1 system derived from *Arabidopsis thaliana* may be employed. See, e.g., Mühlhäuser, W. W. et al. (2017), *Methods Mol. Bio.* 1596:267-70.

The term "teratoma" as used herein refers to a benign germ call tumor containing a mix of tissues and organ components resembling normal derivatives of multiple germ layers. It is known that teratomas modify their microenvironment to establish vasculature and obtain the necessary nutrients for development.

The terms "polynucleotide", "nucleic acid" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

A polynucleotide or polynucleotide region (or a polypeptide or polypeptide region) has a certain percentage (for example, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

An equivalent or biological equivalent nucleic acid, polynucleotide or oligonucleotide or peptide is one having at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence identity to the reference nucleic acid, polynucleotide, oligonucleotide or peptide.

A "gene" refers to a polynucleotide containing at least one open reading frame (ORF) that is capable of encoding a particular polypeptide or protein after being transcribed and translated.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

The term "express" refers to the production of a gene product.

A "gene product" or alternatively a "gene expression product" refers to the amino acid (e.g., peptide or polypeptide) generated when a gene is transcribed and translated.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample; further, the expression level of multiple genes can be determined to establish an expression profile for a particular sample.

The term "IRES" refers to an internal ribosome entry site of viral, prokaryotic, or eukaryotic origin. In some embodiments, an IRES is an RNA element that allows for translation initiation in a cap-independent manner. Common structural features of IRES elements are described in Gritsenko A., et al. (2017) *PLoS Comput Biol* 13(9): e1005734, incorporated herein by reference.

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" intends the polynucleotides are arranged in a manner that allows them to function in a cell.

The term "culturing" refers to the in vitro propagation of cells or organisms on or in media of various kinds. It is understood that the descendants of a cell grown in culture may not be completely identical (i.e., morphologically, genetically, or phenotypically) to the parent cell.

As used herein, the term "vector" refers to a non-chromosomal nucleic acid comprising an intact replicon such that the vector may be replicated when placed within a cell, for example by a process of transformation. Vectors may be viral or non-viral. Viral vectors include retroviruses, adenoviruses, herpesvirus, bacculoviruses, modified bacculoviruses, papovirus, or otherwise modified naturally occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA.

A "viral vector" is defined as a recombinantly produced virus or viral particle that comprises a polynucleotide to be delivered into a host cell, either in vivo, ex vivo or in vitro. Examples of viral vectors include retroviral vectors, lentiviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See Schlesinger and Dubensky (1999) Curr. Opin. Biotechnol. 5:434-439; Ying, et al. (1999) Nat. Med. 5(7):823-827.

In aspects where gene transfer is mediated by a lentiviral vector, a vector construct refers to the polynucleotide comprising the lentiviral genome or part thereof, and a therapeutic gene. As used herein, "lentiviral mediated gene transfer" or "lentiviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. Retroviruses carry their genetic information in the form of RNA; however, once the virus infects a cell, the RNA is reverse-transcribed into the DNA form which integrates into the genomic DNA of the infected cell. The integrated DNA form is called a provirus. As used herein, lentiviral vector refers to a viral particle capable of introducing exogenous nucleic acid into a cell through a viral or viral-like entry mechanism. A "lentiviral vector" is a type of retroviral vector well-known in the art that has certain advantages in transducing non-dividing cells as compared to other retroviral vectors. See, Trono D. (2002) Lentiviral vectors, New York: Spring-Verlag Berlin Heidelberg.

Lentiviral vectors of this invention are based on or derived from oncoretroviruses (the sub-group of retroviruses containing MLV), and lentiviruses (the sub-group of retroviruses containing HIV). Examples include ASLV, SNV and RSV all of which have been split into packaging and vector components for lentiviral vector particle production systems. The lentiviral vector particle according to the invention may be based on a genetically or otherwise (e.g. by specific choice of packaging cell system) altered version of a particular retrovirus.

That the vector particle according to the invention is "based on" a particular retrovirus means that the vector is derived from that particular retrovirus. The genome of the vector particle comprises components from that retrovirus as a backbone. The vector particle contains essential vector components compatible with the RNA genome, including reverse transcription and integration systems. Usually these will include gag and pol proteins derived from the particular retrovirus. Thus, the majority of the structural components of the vector particle will normally be derived from that retrovirus, although they may have been altered genetically or otherwise so as to provide desired useful properties. However, certain structural components and in particular the env proteins, may originate from a different virus. The vector host range and cell types infected or transduced can be altered by using different env genes in the vector particle production system to give the vector particle a different specificity.

As used herein, the term "mixed" in reference to a population of cells refers to population of cells that have differing amounts of an indentifying phenotype or marker, or differing amounts of an exogenous protein, are of a different size, or combinations thereof.

Cell-derived exosomes or microvesicles, also referred to as extracellular exosomes or microvesicles, are membrane surrounded structures that are released by cells in vitro and in vivo. Extracellular exosomes or microvesicles can contain proteins, lipids, and nucleic acids and can mediate intercellular communication between different cells, including different cell types, in the body. Two types of extracellular exosomes or microvesicles are exosomes or microvesicles and microvesicles. Exosomes or microvesicles are small lipid-bound, cellularly secreted exosomes or microvesicles that mediate intercellular communication via cell-to-cell transport of proteins and RNA (El Andaloussi, S. et al. (2013) Nature Reviews: Drug Discovery 12(5):347-357). Exosomes or microvesicles range in size from approximately 30 nm to about 200 nm. Exosomes or microvesicles are released from a cell by fusion of multivesicular endosomes (MVE) with the plasma membrane. Microvescicles, on the other hand, are released from a cell upon direct budding from the plasma membrane (PM) and are packaged with different factors. Microvesicles are typically larger than exosomes or microvesicles and range from approximately 200 nm to 1 μm and have different functionalities.

Cell-derived exosomes or microvesicles can be isolated from eukaryotic cells using commercially available kits as disclosed herein and available from biovision.com and novusbio.com, or using the methods described herein. Non-limiting examples of cells that cell-derived exosomes or microvesicles can be isolated from include stem cells. Non-limiting examples of such stem cells include adult stem cells, embryonic stem cells, embryonic-like stem cells, non-embryonic stem cells, or induced pluripotent stem cells.

As used herein, the terms "overexpress," "overexpression," and the like are intended to encompass increasing the expression of a nucleic acid or a protein to a level greater than the cell, exosome, or microvesicle naturally contains. It is intended that the term encompass overexpression of endogenous, as well as exogenous or heterologous nucleic acids and proteins.

The term "polypeptide", "peptide", and "protein" are used interchangeably and in their broadest sense to refer to a compound of two or more subunits of amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 70% homology or identity, or at least 80% homology or identity and alternatively, or at least about 85%, or alternatively at least about 90%, or alternatively at least about 95%, or alternatively 98% percent homology or identity and exhibits substantially equivalent biological activity to the reference protein, polypeptide or nucleic acid. Alternatively, when referring to polynucleotides, an equivalent thereof is a polynucleotide that hybridizes under stringent conditions to the reference polynucleotide or its complement.

Applicants have provided herein the polypeptide and/or polynucleotide sequences for use in gene and protein transfer and expression techniques described below. It should be understood, although not always explicitly stated that the sequences provided herein can be used to provide the expression product as well as substantially identical sequences that produce a protein that has the same biological properties. These "biologically equivalent" or "biologically active" polypeptides are encoded by equivalent polynucleotides as described herein. They may possess at least 60%, or alternatively, at least 65%, or alternatively, at least 70%, or alternatively, at least 75%, or alternatively at least 80%, or alternatively at least 85%, or alternatively at least 90%, or alternatively at least 95% or alternatively at least 98%, identical primary amino acid sequence to the reference polypeptide when compared using sequence identity methods run under default conditions. Specific polypeptide sequences are provided as examples of particular embodiments. Modifications to the sequences to amino acids with alternate amino acids that have similar charge. Additionally, an equivalent polynucleotide is one that hybridizes under stringent conditions to the reference polynucleotide or its complement or in reference to a polypeptide, a polypeptide encoded by a polynucleotide that hybridizes to the reference encoding polynucleotide under stringent conditions or its complementary strand. Alternatively, an equivalent polypeptide or protein is one that is expressed from an equivalent polynucleotide.

As used herein, the term "microRNAs" or "miRNAs" refers to post-transcriptional regulators that typically bind to complementary sequences in the three prime untranslated regions (3' UTRs) of target messenger RNA transcripts (mRNAs), usually resulting in gene silencing. Typically, miRNAs are short, non-coding ribonucleic acid (RNA) molecules, for example, 21 or 22 nucleotides long. The terms "microRNA" and "miRNA" and "miR" are used interchangeably. Examples of miRNAs are given in Table 1.

A "primer" is a short polynucleotide, generally with a free 3'-OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in MacPherson et al. (1991) PCR 1: A Practical Approach (IRL Press at Oxford University Press). All processes of producing replicate copies of a polynucleotide, such as PCR or gene cloning, are collectively referred to herein as "replication." A primer can also be used as a probe in hybridization reactions, such as Southern or Northern blot analyses. Sambrook and Russell (2001), infra.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC. Additional examples of stringent hybridization conditions include: low stringency of incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed. Hybridization reactions can also be performed under "physiological conditions" which is well known to one of skill in the art. A non-limiting example of a physiological condition is the temperature, ionic strength, pH and concentration of $Mg^{2+}$ normally found in a cell.

When hybridization occurs in an antiparallel configuration between two single-stranded polynucleotides, the reaction is called "annealing" and those polynucleotides are described as "complementary." A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

The term "promoter" refers to a region of DNA that initiates transcription of a particular gene. The promoter includes the core promoter, which is the minimal portion of the promoter required to properly initiate transcription and can also include regulatory elements such as transcription factor binding sites. The regulatory elements may promote transcription or inhibit transcription. Regulatory elements in the promoter can be binding sites for transcriptional activators or transcriptional repressors. A promoter can be constitutive or inducible. A constitutive promoter refers to one that is always active and/or constantly directs transcription of a gene above a basal level of transcription. An inducible promoter is one which is capable of being induced by a molecule or a factor added to the cell or expressed in the cell. An inducible promoter may still produce a basal level of transcription in the absence of induction, but induction typically leads to significantly more production of the protein. Non-limiting examples of promoters include cytomegalovirus (CMV), simian virus 40 (SV40), PGK1, ubiquitin C (Ubc), human beta actin, CAG, TRE, UAS, Ac5, polyhedron, CaMKIIa, GAL1, GAL10, TEF1, GDS, ADH1, CaMV35S, Ubi, H1, U6, SSFV, MNDU3, and EF1-α (alternatively named Ef1a). Promoters can also be tissue specific. A tissue specific promoter allows for the production of a protein in a certain population of cells that have the appropriate transcriptional factors to activate the promoter. Numerous promoters are commercially available and widely known in the art; an exemplary sequence of EF1-α is given in Table 4; another exemplary sequence can be found at Entrez Gene ID 1915.

As used herein, "stem cell" defines a cell with the ability to divide for indefinite periods in culture and give rise to specialized cells. At this time and for convenience, stem cells are categorized as somatic (adult) or embryonic. A somatic stem cell is an undifferentiated cell found in a differentiated tissue that can renew itself (clonal) and (with certain limitations) differentiate to yield all the specialized cell types of the tissue from which it originated. An embryonic stem cell is a primitive (undifferentiated) cell from the embryo that has the potential to become a wide variety of specialized cell types. An embryonic stem cell is one that has been cultured under in vitro conditions that allow proliferation without differentiation for months to years. A clone is a line of cells that is genetically identical to the originating cell; in this case, a stem cell.

A population of cells intends a collection of more than one cell that is identical (clonal) or non-identical in phenotype and/or genotype. A substantially homogenous population of cells is a population having at least 70%, or alternatively at least 75%, or alternatively at least 80%, or alternatively at least 85%, or alternatively at least 90%, or alternatively at least 95%, or alternatively at least 98% identical phenotype, as measured by pre-selected markers.

As used herein, "embryonic stem cells" refers to stem cells derived from tissue formed after fertilization but before the end of gestation, including pre-embryonic tissue (such as, for example, a blastocyst), embryonic tissue, or fetal tissue taken any time during gestation, typically but not necessarily before approximately 10-12 weeks gestation. Most frequently, embryonic stem cells are pluripotent cells derived from the early embryo or blastocyst. Embryonic stem cells can be obtained directly from suitable tissue, including, but not limited to human tissue, or from established embryonic cell lines. "Embryonic-like stem cells" refer to cells that share one or more, but not all characteristics, of an embryonic stem cell.

"Differentiation" describes the process whereby an unspecialized cell acquires the features of a specialized cell such as a heart, liver, or muscle cell.

As used herein, the term "differentiates or differentiated" defines a cell that takes on a more committed ("differentiated") position within the lineage of a cell.

As used herein, the "lineage" of a cell defines the heredity of the cell, i.e. its predecessors and progeny. The lineage of a cell places the cell within a hereditary scheme of development and differentiation.

As used herein, a "pluripotent cell" defines a less differentiated cell that can give rise to at least two distinct (genotypically and/or phenotypically) further differentiated progeny cells. In another aspect, a "pluripotent cell" includes an Induced Pluripotent Stem Cell (iPSC) which is an artificially derived stem cell from a non-pluripotent cell, typically an adult somatic cell, that has historically been produced by inducing expression of one or more stem cell specific genes. Such stem cell specific genes include, but are not limited to, the family of octamer transcription factors, i.e. Oct-3/4; the family of Sox genes, i.e., Sox1, Sox2, Sox3, Sox 15 and Sox 18; the family of Klf genes, i.e. Klf1, Klf2, Klf4 and Klf5; the family of Myc genes, i.e. c-myc and L-myc; the family of Nanog genes, i.e., OCT4, NANOG and REX1; or LIN28. Examples of iPSCs are described in Takahashi et al. (2007) Cell advance online publication 20 Nov. 2007; Takahashi & Yamanaka (2006) Cell 126:663-76; Okita et al. (2007) Nature 448:260-262; Yu et al. (2007) Science advance online publication 20 Nov. 2007; and Nakagawa et al. (2007) Nat. Biotechnol. Advance online publication 30 Nov. 2007.

An "induced pluripotent cell" intends embryonic-like cells reprogrammed to the immature phenotype from adult cells. Various methods are known in the art, e.g., "A simple new way to induce pluripotency: Acid." Nature, 29 Jan. 2014 and available at sciencedaily.com/releases/2014/01/140129184445, last accessed on Feb. 5, 2014 and U.S. Patent Application Publication No. 2010/0041054. Human iPSCs also express stem cell markers and are capable of generating cells characteristic of all three germ layers.

As used herein, the term "thymidine kinase" or "TK" intends a thymidine kinase gene "TK" suitable for use as a suicide gene to provide biosafety to recombinant vectors. The sequence of herpes simplex virus thymidine kinase ("HSV-tk") is provided in Table 3 (nucleotides 1-1,128) and at GenBank Accession No. AB45318.1 (nucleotides 3331-4458). Other non-limiting examples examples are found at GenBank Accession Nos. AF057310.1 (nucleotides 306-1436), among others. Other non-limiting examples of such include codon optimized TK or tk30, tk75 and sr39tk, described in Pantuck et al. (2004) Human Gene Therapy, Vol. 13(7): 777-789; Black et al. (2001) Cancer Res. 61:3022-3026; and Ardiani, et al. (2010) Cancer Gene Therapy 17:86-96. Additional examples of equivalents or biological equivalents include polynucleotides having the TK biological activity and which have at least 80%, or alternatively at least 85%, or alternatively at least 90%, or alternatively at least 95%, or alternatively at least 97% sequence identity to HSV-tk or GenBank Accession No. AB45318.1 (nucleotides 3331-4458), or a polynucleotide that hybridizes under conditions of high stringency to GenBank Accession No. AB45318.1 (nucleotides 3331-4458) or its complement or GenBank Accession Nos. AF057310.1 (nucleotides 306-1436) or its complement, wherein conditions of high stringency comprise incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water.

The term "transcription factor" includes proteins that are involved in gene regulation in prokaryotic and/or eukaryotic organisms. In some embodiments, a transcription factor has a positive effect on gene expression and, thus, may be referred to as an "activator" or a "transcriptional activation factor." In some embodiments, a transcription factor can negatively effect gene expression and, thus, may be referred to as a "repressor" or a "transcription repression factor." Activators and repressors are generally used terms and their functions are discerned by those skilled in the art. Non-limiting examples of transcription factors include ETV2 (Entrez Gene ID 2116), MYOD1 (myoblast determination protein 1; Entrez Gene ID 4654), and NEUROD1 (neuronal differentiation 1; Entrez Gene ID 4760), among others.

A "composition" is intended to mean a combination of active polypeptide, polynucleotide or antibody and another compound or composition, inert (e.g. a detectable label) or active (e.g. a gene delivery vehicle).

A "pharmaceutical composition" is intended to include the combination of an active polypeptide, polynucleotide or antibody with a carrier, inert or active such as a solid support, making the composition suitable for diagnostic or therapeutic use in vitro, in vivo or ex vivo.

A "subject," "individual" or "patient" is used interchangeably herein, and refers to a vertebrate, preferably a mammal, more preferably a human. Mammals include, but are not limited to, murines, rats, rabbit, simians, bovines, ovine, porcine, canines, feline, farm animals, sport animals, pets, equine, and primate, particularly human. Besides being useful for human treatment, the present invention is also useful for veterinary treatment of companion mammals, exotic animals and domesticated animals, including mammals, rodents, and the like which is susceptible to neurodegenerative disease. In one embodiment, the mammals include horses, dogs, and cats. In another embodiment of the present invention, the human is an adolescent or infant under the age of eighteen years of age.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

The term "suffering" as it related to the term "treatment" refers to a patient or individual who has been diagnosed with or is predisposed to infection or a disease incident to infection. A patient may also be referred to being "at risk of suffering" from a disease because of active or latent infection. This patient has not yet developed characteristic disease pathology.

"Treating" or "treatment" of a disease includes: (1) preventing the disease, i.e., causing the clinical symptoms of the disease not to develop in a patient that may be predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present invention for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. In general, one will desire to administer an amount of the compound that is effective to achieve a serum level commensurate with the concentrations found to be effective in vitro. Determination of these parameters is well within the skill of the art. These considerations, as well as effective formulations and administration procedures are well known in the art and are described in standard textbooks. Consistent with this definition, as used herein, the term "therapeutically effective amount" is an amount sufficient to inhibit RNA virus replication ex vivo, in vitro or in vivo.

DESCRIPTIVE EMBODIMENTS

Having been generally described herein, the follow examples are provided to further illustrate this invention.

Applicant has developed a technology that is capable of growing human tissue by way of biasing the differentiation of a stem cell population using lineage-specific miRNA and transcription factor (TF) overexpression vectors—i.e., lineage-specific biasing.

Methods of Sculpting Through miRNA

Described herein are methods, systems, and compositions to engineer tissue using lineage-specific biasing. The methods, systems, and compositions described herein provide high utility and versatility when compared to other methods, systems, and compositions for engineering tissue.

Accordingly, in some aspects, provided herein is a method comprising, or alternatively consisting essentially of, or yet further consisting of, the step of administering a prodrug to a mixed cell population comprising a lineage-specific miRNA-binding polynucleotide, wherein the lineage-specific miRNA-binding polynucleotide comprises (i) at least one lineage-specific miRNA binding site operably linked to (ii) a polynucleotide encoding a prodrug modification polypeptide, and wherein the mixed cell population comprises at least one cell comprising a lineage-specific miRNA capable of binding to the lineage-specific miRNA binding site. In some embodiments, the binding of the lineage-specific miRNA to the miRNA-binding site silences expression of the prodrug modification polypeptide.

In some embodiments, the prodrug is cytotoxic when modified by the prodrug modification polypeptide. In some embodiments, the prodrug modification polypeptide is selected from a viral tyrosine kinase, a bacterial cytosine deaminase, carboxypeptidase G2, purine nucleoside phosphorylase, nitroreductase, deoxycytidine kinase, cytochrome P450, a horseradish peroxidase, a guanine ribosyltransferase, a β-glucuronidase, a β-galactosidase, a thymidine phosphorylase, methionine-α,γ-lyase, and an equivalent of each thereof. In some embodiments, the prodrug modification polypeptide is herpes simplex virus thymidine kinase (HSV-tk) or an equivalent thereof. In some embodiments, the prodrug is selected from ganciclovir, penciclovir, acyclovir, valacyclovir, (E)-5-(2-bromovinyl)-2'-deoxyuridine (BVDU), zidovudine, 2'-exo-methanocarbathymidine, 5-fluorocytosine, 5-methylpurine deoxyriboside (MEP), fludarabine, cyclophosphamide, ifosfamide, acetaminophen, 4-ipomeanol, 4-[(2-chloroethyl)(2-mesyloxyethyl)amino] benzoyl-L-glutamic acid (CMDA), hydroxy-aniline mustards, amino-ainiline mustards, anthracycline glutamates, methotrexate α-peptides, irinotecan, anthracycline acetals, CB1954, SN23862, 4-nitrobenzyl carbamates, quinones, indole-3-acetic acid, 6-thioxanthine, HM1826, anthracycline acetals, 5'-deoxy-5-fluorouridine, selenomethionine, and an equivalent of each thereof. In some embodiments, the prodrug is ganciclovir or an equivalent thereof.

In some embodiments, the lineage-specific miRNA-binding polynucleotide further comprises (iii) a promoter operably linked to the lineage-specific miRNA binding site. In some embodiments, the promoter is a constitutive promoter. In some embodiments, the promoter is an inducible promoter. In some embodiments, the promoter is selected from promoters for each of elongation factor-1 alpha (EF1-α), cytomegalovirus (CMV), simian virus 40 (SV40), PGK1, ubiquitin C (Ubc), human beta actin, CAG, TRE, UAS, Ac5, polyhedron, CaMKIIa, GAL1, GAL10, TEF1, GDS, ADH1, CaMV35S, Ubi, H1, U6, and an equivalent of each thereof.

In some embodiments, the lineage-specific miRNA-binding polynucleotide further comprises (iv) a polynucleotide encoding a fluorescent protein, wherein the polynucleotide encoding the fluorescent protein is operably linked to the lineage-specific miRNA binding site. In some embodiments, the fluorescent protein is selected from green fluorescent protein (GFP), red fluorescent protein (RFP), cyan fluorescent protein (CFP), blue fluorescent protein (BFP), yellow fluorescent protein (YFP), orange fluorescent protein (OFP), far-red protein, near-IR protein, and an equivalent of each thereof. In some embodiments, the polynucleotide encoding the fluorescent protein and the polynucleotide encoding the prodrug modification polypeptide are linked by a polynucleotide selected from the group consisting of an internal ribosome entry site (IRES) element and a self-cleaving 2A peptide-encoding sequence.

In some embodiments, the lineage-specific miRNA corresponds to a cell lineage selected from pluripotent stem cells, tumors, liver cells, neural cells, endothelial cells, pluripotent stem cells, and an equivalent of each thereof. In some embodiments, the lineage-specific miRNA binding site is capable of binding a polynucleotide selected from the group consisting of miR-21, miR-122, miR-124, miR-126, miR-302A, miR-1, miR-7, miR-9, miR-10, miR-96, miR-133, miR-137, miR-140, miR-143, miR-145, miR-181, miR-184, miR-199, miR-200, miR-203, miR-208a, miR-214, miR-218, miR-223, miR-338, miR-375, and miR-451.

In some embodiments, the mixed cell population is a teratoma.

miRNA-Binding Polynucleotides

In some aspects, provided herein is a miRNA-binding polynucleotide comprising, or alternatively consisting essentially of, or yet further consisting of, a promoter; at least one lineage-specific miRNA binding site; and a polynucleotide encoding a prodrug modification polypeptide; wherein the lineage-specific miRNA binding site is capable of binding a lineage-specific miRNA. In some embodiments, the binding of the lineage-specific miRNA to the miRNA-binding site silences expression of the prodrug modification polypeptide.

In some embodiments, the prodrug modification polypeptide is capable of modifying a prodrug such that the prodrug is cytotoxic. In some embodiments, the prodrug modification polypeptide is selected from a viral tyrosine kinase, a bacterial cytosine deaminase, carboxypeptidase G2, purine nucleoside phosphorylase, nitroreductase, deoxycytidine kinase, cytochrome P450, a horseradish peroxidase, a guanine ribosyltransferase, a β-glucuronidase, a β-galactosidase, a thymidine phosphorylase, methionine-α,γ-lyase, and an equivalent of each thereof. In some embodiments, the prodrug modification polypeptide is herpes simplex virus thymidine kinase (HSV-tk) or an equivalent thereof. In some embodiments, the prodrug is selected from ganciclovir, penciclovir, acyclovir, valacyclovir, (E)-5-(2-bromovinyl)-2'-deoxyuridine (BVDU), zidovudine, 2'-exo-methanocarbathymidine, 5-fluorocytosine, 5-methylpurine deoxyriboside (MEP), fludarabine, cyclophosphamide, ifosfamide, acetaminophen, 4-ipomeanol, 4-[(2-chloroethyl)(2-mesyloxyethyl)amino]benzoyl-L-glutamic acid (CMDA), hydroxy-aniline mustards, amino-ainiline mustards, anthracycline glutamates, methotrexate α-peptides, irinotecan, anthracycline acetals, CB1954, SN23862, 4-nitrobenzyl carbamates, quinones, indole-3-acetic acid, 6-thioxanthine, HM1826, anthracycline acetals, 5'-deoxy-5-fluorouridine, selenomethionine, and an equivalent of each thereof. In some embodiments, the prodrug is ganciclovir or an equivalent thereof.

In some embodiments, the lineage-specific miRNA-binding polynucleotide further comprises (iii) a promoter operably linked to the lineage-specific miRNA binding site. In some embodiments, the promoter is a constitutive promoter. In some embodiments, the promoter is an inducible promoter. In some embodiments, the promoter is selected from promoters for each of elongation factor-1 alpha (EF1-α), cytomegalovirus (CMV), simian virus 40 (SV40), PGK1, ubiquitin C (Ubc), human beta actin, CAG, TRE, UAS, Ac5, polyhedron, CaMKIIa, GAL1, GAL10, TEF1, GDS, ADH1, CaMV35S, Ubi, H1, U6, and an equivalent of each thereof.

In some embodiments, the lineage-specific miRNA corresponds to a cell lineage selected from pluripotent stem cells, tumors, liver cells, neural cells, endothelial cells, pluripotent stem cells, and an equivalent of each thereof. In some embodiments, the lineage-specific miRNA binding site is capable of binding a polynucleotide selected from the group consisting of miR-21, miR-122, miR-124, miR-126, miR-302A miR-1, miR-7, miR-9, miR-10, miR-96, miR-133, miR-137, miR-140, miR-143, miR-145, miR-181, miR-184, miR-199, miR-200, miR-203, miR-208a, miR-214, miR-218, miR-223, miR-338, miR-375, and miR-451.

In some embodiments, the mixed cell population is a teratoma.

Vectors for miRNA Sculpting

In some aspects, provided herein is a vector comprising, or alternatively consisting essentially of, or yet further consisting of, an miRNA binding polynucleotide comprising, or alternatively consisting essentially of, or yet further consisting of, a promoter; at least one lineage-specific miRNA binding site; and a polynucleotide encoding a prodrug modification polypeptide; wherein the lineage-specific miRNA binding site is capable of binding a lineage-specific miRNA. In some embodiments, the binding of the lineage-specific miRNA to the miRNA-binding site silences expression of the prodrug modification polypeptide.

In some embodiments, the vector is an adenoviral vector, an adenovirus associated vector, or a lentiviral vector.

In some embodiments, the vector further comprises a polynucleotide encoding a selectable marker. In some embodiments, the selectable marker is a gene that confers a trait suitable for artificial selection of a prokaryotic or eukaryotic host cell. Nonlimiting examples of selectable markers suitable for prokaryotic host cells include beta-lactamase which confers resistance to ampicillin and URA3. Nonlimiting examples of selectable markers for eukaryotic transduced cells include genes that confer resistance to blasticidin (bsd), G418/Geneticin (neo), hygromycin (hygB), puromycin (pac), and zeocin (Sh bla).

Viral Particles for miRNA Sculpting

In some aspects, provided herein is a viral particle comprising, or alternatively consisting essentially of, or yet further consisting of, one or more miRNA binding polynucleotide comprising, or alternatively consisting essentially of, or yet further consisting of, a promoter; at least one lineage-specific miRNA binding site; and a polynucleotide encoding a prodrug modification polypeptide; wherein the lineage-specific miRNA binding site is capable of binding a lineage-specific miRNA. In some embodiments, the binding of the lineage-specific miRNA to the miRNA-binding site silences expression of the prodrug modification polypeptide.

Lineage-Inducible Mixed Cell Populations

In some aspects, provided herein is a method of producing a lineage-inducible mixed cell population comprising, or alternatively consisting essentially of, or yet further consisting of, (a) transducing a population of stem cells with one or more viral particles described herein, and (b) culturing the population of transduced stem cells in (a) under conditions suitable to produce a lineage-inducible mixed cell population.

In some embodiments, the stem cells are embryonic stem cells or induced pluripotent stem cells. In some embodiments, the lineage-inducible mixed cell population is a teratoma.

In some embodiments, the suitable conditions comprise one or more of: culturing the transduced stem cells in the presence of one or more cytokines or growth factors, culturing the cells in conditioned medium, culturing the cells in low oxygen or hypoxic conditions, culturing the cells on a scaffold, and culturing the cells for at least 1, at least 2, at least 3, at least 4, at least 5, at least 6, at least 7, at least 8, at least 9, at least 10, at least 11, at least 12, at least 13, at least 14, or at least 21 days. In some embodiments, suitable conditions comprise selection of cells transduced with the one or more viral particles.

Also provided herein are populations of lineage-inducible mixed cells produced by the methods described herein.

In some embodiments, provided herein are kits comprising the populations of lineage-inducible mixed cells produced by the methods described herein, and optionally instructions for their use. In some embodiments, the kits further comprise a prodrug.

miRNA-Binding Polynucleotides and Systems of their Use

In some aspects, provided herein is a miRNA-binding polynucleotide comprising, or alternatively consisting essentially of, or yet further consisting of, a promoter comprising elongation factor-1 alpha (EF1-α), the promoter being operably linked to a polynucleotide construct comprising: a first lineage-specific miRNA binding site, a polynucleotide encoding herpes simplex virus thymidine kinase (HSV-tk), a polynucleotide encoding self-cleaving 2A peptide, a polynucleotide encoding green fluorescent protein (GFP), and a second lineage-specific miRNA binding site. In some embodiments, provided herein is a system comprising, or alternatively consisting essentially of, or yet further consisting of, the miRNA-binding polynucleotide, a stem cell population, and a prodrug. In some embodiments, the prodrug is cytotoxic when modified by the prodrug modification polypeptide.

Methods of Transcription Factor Overexpression

In some aspects, provided herein is a method comprising, or alternatively consisting essentially of, or yet further consisting of, overexpressing in a stem cell population at least one transcription factor capable of biasing differentiation of the stem cell population, and exposing the stem cell population to a growth medium, wherein the growth medium is compatible with biasing differentiation of the stem cell population, and wherein the stem cell population comprises either a teratoma, optionally derived from human pluripotent stem cells (hPSCs), iPSCs, or an ex vivo tissue engineered construct.

In some embodiments, 1, 2, 3, 4, 5, 6, 7, 8, 9, or 10 transcription factors are overexpressed in the stem cell population. In some embodiments, each transcription factor is overexpressed in the same cell. In other embodiments, the transcription factors are overexpressed in different stem cells. In some embodiments, stem cells overexpressing different transcription factors are mixed together to provide a single population of cells.

In some embodiments, the transcription factor is ETV2, MYOD1 and NEUROD1. In some embodiments, the growth medium is an endothelial growth medium.

In some embodiments, the stem cell population comprises one or more transcription-factor overexpression polynucleotides comprising a promoter, the promoter being operably linked to a polynucleotide comprising a polynucleotide encoding the transcription factor capable of biasing differentiation of the stem cell population, a selection marker, and optionally, an internal ribosome entry site (IRES) element or a polynucleotide encoding self-cleaving 2A peptide. In some embodiments, the promoter is a constitutive promoter. In some embodiments, the promoter is an inducible promoter. In some embodiments, the promoter is selected from promoters for each of elongation factor-1 alpha (EF1-α), cytomegalovirus (CMV), simian virus 40 (SV40), PGK1, ubiquitin C (Ubc), human beta actin, CAG, TRE, UAS, Ac5, polyhedron, CaMKIIa, GAL1, GAL10, TEF1, GDS, ADH1, CaMV35S, Ubi, H1, U6, and an equivalent of each thereof.

In some embodiments, the the stem cell population comprises one or more transcription-factor overexpression polynucleotides comprising a polynucleotide encoding the transcription factor capable of biasing differentiation of the stem cell population, a selection marker, and optionally, an internal ribosome entry site (IRES) element or a polynucleotide encoding self-cleaving 2A peptide, wherein transcription of the transcription-factor overexpression polynucleotide is under control of an inducible system. In some embodiments, the inducible system is a doxycycline-induced gene expression system. In some embodiments, the doxycycline-induced gene expression system is Tet-On 3G.

In some embodiments, the stem cell population comprises an inactivated Cas protein lacking DNA endonuclease activity, a transcriptional activation domain operably linked to the inactivated Cas protein, and at least one CRISPR guide RNA capable of binding to the inactivated Cas protein and capable of binding to an endogenous genomic site of the stem cell population so as to overexpress the transcription factor capable of biasing differentiation of the stem cell population.

In some embodiments, the stem cell population comprises an optically controlled overexpression protein complex comprising a first half of a photodimerisable protein, operably linked to an inactivated Cas protein lacking DNA endonuclease activity; a second half of a photodimerisable protein, operably linked to a transcriptional activation domain and capable of being operably linked to the first half of the photodimerisable protein through photodimerisation; and at least one CRISPR guide RNA capable of binding to the inactivated Cas protein and capable of binding to an endogenous genomic site of the stem cell population so as to overexpress the transcription factor capable of biasing differentiation of the stem cell population when the first half and the second half of the photodimerisable protein are linked.

In some embodiments, the stem cell population comprises an optically controlled overexpression protein complex comprising a first half of a photodimerisable protein, operably linked to a first half of an inactivated Cas protein lacking DNA endonuclease activity; a second half of a photodimerisable protein, operably linked to molecule comprising a second half of an inactivated Cas protein lacking DNA endonuclease activity operably linked to a transcriptional activation domain, wherein the second half of the photodimerisable protein is capable of being operably linked to the first half of the photodimerisable protein through photodimerisation; and at least one CRISPR guide RNA capable of binding to the inactivated Cas protein and capable of binding to an endogenous genomic site of the stem cell population so as to overexpress the transcription factor capable of biasing differentiation of the stem cell population when the first half and the second half of the photodimerisable protein are linked.

Transcription-Factor Overexpression Polynucleotides and Polypeptides

In some aspects, provided herein is one or more transcription-factor overexpression polynucleotides comprising, or alternatively consisting essentially of, or yet further consisting of, a promoter, the promoter being operably linked to a polynucleotide comprising a polynucleotide encoding a transcription factor capable of biasing differentiation of a stem cell population, a selection marker; and optionally, an internal ribosome entry site (IRES) element or a polynucleotide encoding self-cleaving 2A peptide.

In some aspects, provided herein is one or more transcription-factor overexpression polynucleotides comprising, or alternatively consisting essentially of, or yet further consisting of, a polynucleotide encoding a transcription factor capable of biasing differentiation of a stem cell population, a selection marker, and, optionally, an internal ribosome entry site (IRES) element or a polynucleotide encoding self-cleaving 2A peptide, wherein transcription of the transcription-factor overexpression polynucleotide is under control of an inducible system.

In some aspects, provided herein is a polypeptide encoded by the transcription-factor overexpression polynucleotides described herein.

Systems for Transcription-Factor Overexpression-Based Lineage Biasing

In some aspects, provided herein is a system comprising, or alternatively consisting essentially of, or yet further consisting of, a stem cell population and one or more transcription-factor overexpression polynucleotides comprising a promoter, the promoter being operably linked to a polynucleotide comprising a polynucleotide encoding a transcription factor capable of biasing differentiation of a stem cell population, a selection marker, and, optionally, an internal ribosome entry site (IRES) element or a polynucleotide encoding self-cleaving 2A peptide.

In some aspects, provided herein is a system comprising, or alternatively consisting essentially of, or yet further consisting of, a stem cell population and one or more transcription-factor overexpression polynucleotides comprising a polynucleotide encoding a transcription factor capable of biasing differentiation of a stem cell population, a selection marker, and, optionally, an internal ribosome entry site (IRES) element or a polynucleotide encoding self-cleaving 2A peptide, wherein transcription of the transcription-factor overexpression polynucleotide is under control of an inducible system.

In some aspects, provided herein is a system comprising, or alternatively consisting essentially of, or yet further consisting of, a stem cell population, an inactivated Cas protein lacking DNA endonuclease activity, a transcriptional activation domain operably linked to the inactivated Cas protein, and at least one CRISPR guide RNA capable of binding to the inactivated Cas protein and capable of binding to an endogenous genomic site of the stem cell population so as to overexpress at least one transcription factor capable of biasing differentiation of the stem cell population.

In some aspects, provided herein is a system comprising, or alternatively consisting essentially of, or yet further consisting of, a stem cell population and an optically controlled overexpression protein complex comprising a first half of a photodimerisable protein, operably linked to an inactivated Cas protein lacking DNA endonuclease activity, a second half of a photodimerisable protein, operably linked to a transcriptional activation domain and capable of being operably linked to the first half of the photodimerisable protein through photodimerisation, and at least one CRISPR guide RNA capable of binding to the inactivated Cas protein and capable of binding to an endogenous genomic site of the stem cell population so as to overexpress at least one transcription factor capable of biasing differentiation of the stem cell population when the first half and the second half of the photodimerisable protein are linked.

In some aspects, provided herein is a system comprising, or alternatively consisting essentially of, or yet further consisting of, a stem cell population and an optically controlled overexpression protein complex comprising a first half of a photodimerisable protein, operably linked to a first half of an inactivated Cas protein lacking DNA endonuclease activity, a second half of a photodimerisable protein, operably linked to molecule comprising a second half of an inactivated Cas protein lacking DNA endonuclease activity operably linked to a transcriptional activation domain, wherein the second half of the photodimerisable protein is capable of being operably linked to the first half of the photodimerisable protein through photodimerisation, and at least one CRISPR guide RNA capable of binding to the inactivated Cas protein and capable of binding to an endogenous genomic site of the stem cell population so as to overexpress at least one transcription factor capable of biasing differentiation of the stem cell population when the first half and the second half of the photodimerisable protein are linked.

Overexpression Systems

In some aspects, provided herein is an optically controlled overexpression system comprising, or alternatively consisting essentially of, or yet further consisting of, a first half of a photodimerisable protein, operably linked to an inactivated Cas protein lacking DNA endonuclease activity, a second half of a photodimerisable protein, operably linked to a transcriptional activation domain and capable of being operably linked to the first half of the photodimerisable protein through photodimerisation, and at least one CRISPR guide RNA capable of binding to the inactivated Cas protein and capable of binding to an endogenous genomic site of the stem cell population so as to overexpress at least one transcription factor capable of biasing differentiation of the stem cell population when the first half and the second half of the photodimerisable protein are linked.

In some aspects, provided herein is an optically controlled overexpression system comprising, or alternatively consisting essentially of, or yet further consisting of, a first half of a photodimerisable protein, operably linked to a first half of an inactivated Cas protein lacking DNA endonuclease activity, a second half of a photodimerisable protein, operably linked to molecule comprising a second half of an inactivated Cas protein lacking DNA endonuclease activity operably linked to a transcriptional activation domain, wherein the second half of the photodimerisable protein is capable of being operably linked to the first half of the photodimerisable protein through photodimerisation, and at least one CRISPR guide RNA capable of binding to the inactivated Cas protein and capable of binding to an endogenous genomic site of the stem cell population so as to overexpress at least one transcription factor capable of biasing differentiation of the stem cell population when the first half and the second half of the photodimerisable protein are linked.

In some aspects, provided herein is an overexpression system comprising, or alternatively consisting essentially of, or yet further consisting of, an inactivated Cas protein lacking DNA endonuclease activity, a transcriptional activation domain operably linked to the inactivated Cas protein, and at least one CRISPR guide RNA capable of binding to the inactivated Cas protein and capable of binding to an endogenous genomic site of the stem cell population so as to overexpress a transcription factor capable of biasing differentiation of a stem cell population.

In some aspects, the photodimerisable protein is derived from the CRY2-CIB1 system.

Methods using miRNA Sculpting and Transcription-Factor Overexpression

In some aspects, provided herein is a method comprising, or alternatively consisting essentially of, or yet further consisting of, one or more of the steps, in any order, of one or more of the steps, in any order, of (a) administering a prodrug to a mixed cell population comprising a lineage-specific miRNA-binding polynucleotide, wherein the lineage-specific miRNA-binding polynucleotide comprises a lineage-specific miRNA binding site operably linked to a polynucleotide encoding a prodrug modification polypeptide and wherein the mixed cell population comprises at least one cell type that expresses a lineage-specific miRNA that binds to the lineage-specific miRNA binding site; and (b) overexpressing in the mixed cell population a transcription factor capable of biasing differentiation of the mixed cell population and exposing the mixed cell population to a growth medium, wherein the growth medium is compatible with biasing differentiation of the mixed cell population.

In some embodiments, binding of the lineage-specific miRNA to the miRNA-binding site silences expression of the prodrug modification polypeptide.

In some embodiments, the prodrug is cytotoxic when modified by the prodrug modification polypeptide. In some embodiments, the prodrug modification polypeptide is selected from a viral tyrosine kinase, a bacterial cytosine deaminase, carboxypeptidase G2, purine nucleoside phosphorylase, nitroreductase, deoxycytidine kinase, cytochrome P450, a horseradish peroxidase, a guanine ribosyltransferase, a β-glucuronidase, a β-galactosidase, a thymidine phosphorylase, methionine-α,γ-lyase, and an equivalent of each thereof. In some embodiments, the prodrug modification polypeptide is herpes simplex virus thymidine kinase (HSV-tk), or an equivalent thereof. In some embodiments, the prodrug is selected from ganciclovir, penciclovir, acyclovir, valacyclovir, (E)-5-(2-bromovinyl)-2'-deoxyuridine (BVDU), zidovudine, 2'-exo-methanocarbathymidine, 5-fluorocytosine, 5-methylpurine deoxyriboside (MEP), fludarabine, cyclophosphamide, ifosfamide, acetaminophen, 4-ipomeanol, 4-[(2-chloroethyl)(2-mesyloxyethyl)amino]benzoyl-L-glutamic acid (CMDA), hydroxy-aniline mustards, amino-ainiline mustards, anthracycline glutamates, methotrexate α-peptides, irinotecan, anthracycline acetals, CB1954, SN23862, 4-nitrobenzyl carbamates, quinones, indole-3-acetic acid, 6-thioxanthine, HM1826, anthracycline acetals, 5'-deoxy-5-fluorouridine, selenomethionine, and an equivalent of each thereof. In some embodiments, the prodrug is ganciclovir or an equivalent thereof.

In some embodiments, the mixed cell population is a teratoma.

In some embodiments, the lineage-specific miRNA-binding polynucleotide further comprises a promoter operably linked to the lineage-specific miRNA binding site. In some embodiments, the promoter is a constitutive promoter. In some embodiments, the promoter is an inducible promoter. In some embodiments, the promoter is selected from promoters for each of elongation factor-1 alpha (EF1-α), cytomegalovirus (CMV), simian virus 40 (SV40), PGK1, ubiquitin C (Ubc), human beta actin, CAG, TRE, UAS, Ac5, polyhedron, CaMKIIa, GAL1, GAL10, TEF1, GDS, ADH1, CaMV35S, Ubi, H1, U6, and an equivalent of each thereof.

In some embodiments, the lineage-specific miRNA-binding polynucleotide further comprises a polynucleotide encoding a fluorescent protein, wherein the polynucleotide encoding the fluorescent protein is operably linked to the lineage-specific miRNA binding site. In some embodiments, the fluorescent protein is selected from green fluorescent protein (GFP), red fluorescent protein (RFP), cyan fluorescent protein (CFP), blue fluorescent protein (BFP), yellow fluorescent protein (YFP), orange fluorescent protein (OFP), far-red protein, near-IR protein, and an equivalent of each thereof. In some embodiments, the polynucleotide encoding the fluorescent protein and the polynucleotide encoding the prodrug modification polypeptide are linked by a polynucleotide selected from the group consisting of an internal ribosome entry site (IRES) element and a self-cleaving 2A peptide-encoding sequence.

In some embodiments, the lineage-specific miRNA corresponds to a cell lineage selected from pluripotent stem cells, tumors, liver cells, neural cells, endothelial cells, pluripotent stem cells, iPSCs and an equivalent of each thereof. In some embodiments, the lineage-specific miRNA binding site is capable of binding a polynucleotide selected from the group consisting of miR-21, miR-122, miR-124, miR-126, miR-302A miR-1, miR-7, miR-9, miR-10, miR-96, miR-133, miR-137, miR-140, miR-143, miR-145, miR-181, miR-184, miR-199, miR-200, miR-203, miR-208a, miR-214, miR-218, miR-223, miR-338, miR-375, and miR-451.

In some aspects, provided herein is a method comprising, or alternatively consisting essentially of, or yet further consisting of, the steps of (a)(i) transducing a stem cell population with the viral particle described herein or more polynucleotides encoding one or more transcription factors, and/or miRNA and (ii) culturing the population of transduced stem cells in (a)(i) under conditions suitable to produce a lineage-inducible mixed cell population; and (b) overexpressing in the stem cell population at least one transcription factor capable of biasing differentiation of the stem cell population; and exposing the stem cell population to a growth medium, wherein the growth medium is compatible with biasing differentiation of the stem cell population.

In some embodiments, the stem cell population is a teratoma.

In some embodiments, the transcription factor is ETV2, MYOD1 and NEUROD1 or an equivalent thereof.

In some embodiments, the growth medium is an endothelial growth medium or an equivalent thereof.

In some embodiments, the stem cell or mixed cell population comprises one or more transcription-factor overexpression polynucleotides comprising a promoter, the promoter being operably linked to a polynucleotide comprising a polynucleotide encoding the transcription factor capable of biasing differentiation of the mixed cell population, a selection marker, and, optionally, an internal ribosome entry site (IRES) element or a polynucleotide encoding self-cleaving 2A peptide. In some embodiments, the promoter is a constitutive promoter. In some embodiments, the promoter is an inducible promoter. In some embodiments, the promoter is selected from promoters for each of elongation factor-1 alpha (EF1-α), cytomegalovirus (CMV), simian virus 40 (SV40), PGK1, ubiquitin C (Ubc), human beta actin, CAG, TRE, UAS, Ac5, polyhedron, CaMKIIa, GAL1, GAL10, TEF1, GDS, ADH1, CaMV35S, Ubi, H1, U6, and an equivalent of each thereof.

In some embodiments, the stem cell or mixed cell population comprises one or more transcription-factor overexpression polynucleotides comprising a polynucleotide encoding the transcription factor capable of biasing differentiation of the mixed cell population, a selection marker, and, optionally, an internal ribosome entry site (IRES) element or a polynucleotide encoding self-cleaving 2A peptide, wherein transcription of the transcription-factor overexpression polynucleotide is under control of an inducible system. In some embodiments, the inducible system is a doxycycline-induced gene expression system. In some embodiments, the doxycycline-induced gene expression system is Tet-On 3G.

In some embodiments, the stem cell or mixed cell population comprises an inactivated Cas protein lacking DNA endonuclease activity, a transcriptional activation domain operably linked to the inactivated Cas protein, and at least one CRISPR guide RNA capable of binding to the inactivated Cas protein and capable of binding to an endogenous genomic site of the mixed cell population so as to overexpress the transcription factor capable of biasing differentiation of the mixed cell population.

In some embodiments, the stem cell or mixed cell population comprises an optically controlled overexpression protein complex comprising a first half of a photodimerisable protein, operably linked to an inactivated Cas protein lacking DNA endonuclease activity, a second half of a photodimerisable protein, operably linked to a transcriptional activation domain and capable of being operably linked to the first half of the photodimerisable protein through photodimerisation, and at least one CRISPR guide RNA capable of binding to the inactivated Cas protein and capable of binding to an endogenous genomic site of the mixed cell population so as to overexpress the transcription factor capable of biasing differentiation of the mixed cell population when the first half and the second half of the photodimerisable protein are linked.

In some embodiments, the stem cell or mixed cell population comprises an optically controlled overexpression protein complex comprising a first half of a photodimerisable protein, operably linked to a first half of an inactivated Cas protein lacking DNA endonuclease activity, a second half of a photodimerisable protein, operably linked to molecule comprising a second half of an inactivated Cas protein lacking DNA endonuclease activity operably linked to a transcriptional activation domain, wherein the second half of the photodimerisable protein is capable of being operably linked to the first half of the photodimerisable protein through photodimerisation, and CRISPR guide RNA capable of binding to the inactivated Cas protein and capable of binding to an endogenous genomic site of the stem cell population so as to overexpress the transcription factor capable of biasing differentiation of the mixed cell population when the first half and the second half of the photodimerisable protein are linked.

In some embodiments, the teratoma is derived from human pluripotent stem cells (hPSCs) or iPSCs.

In some embodiments, the mixed cell or stem cell population comprises an ex vivo tissue engineered construct.

Cells and Cell Populations

In some aspects, provided herein is a cell population obtained using any of the methods or systems described herein. In some embodiments, the cell population is isolated.

In some aspects, provided herein is a cell or a cell population comprising any of the miRNA-binding polynucleotides, transcription-factor overexpression polynucleotides, optically controlled overexpression systems, overexpression systems, vectors, or viral particles described herein. In some embodiments, the cell or cell population is isolated.

In some embodiments, the cell population is substantially homogenous, comprising at least 99%, at least 98%, at least 97%, at least 95%, at least 90%, at least 85%, at least 80%, at least 75%, at least 70%, at least 65%, at least 60%, at least 55%, or at least 50% of cells of the same lineage. A cell's lineage can be determined, for example, by morphology and/or by detecting expression of one or more lineage-specific markers. Expression of a lineage-specific marker can be determined by methods known in the art including but not limited to immunohistochemistry, flow cytometry, immunofluorescence, Western blot, Northern blot, PCR, quantitative PCR, Southern blot, nucleic acid sequencing, and ELISA In some aspects, provided herein is a composition comprising a cell or cell population is obtained using any of the methods or systems described herein and a carrier. In some embodiments, the carrier is a pharmaceutically acceptable carrier.

Therapeutic Methods

In some aspects, provided herein is a method of treating a subject in need thereof, the method comprising administering a cell or a cell population comprising any of the miRNA-binding polynucleotides, transcription-factor overexpression polynucleotides, optically controlled overexpression systems, overexpression systems, vectors, or viral particles described herein. In some embodiments, an effective amount of the cell or cell population is administered to the subject.

In some embodiments, the subject in need thereof is a subject in need of a tissue transplant.

In some embodiments, the cell or cell population autologous to the subject. In some embodiments, the cell or cell population is allogenic to the subject. In some embodiments, the cell or cell population is derived from a donor that shares one or more HLA markers with the subject.

Additional advantages and applications of the present invention are provided in the following examples, which should be considered as illustrative and nonlimiting.

Example 1: Molecular Sculpting Through miRNAs

Micro RNAs (miRNAs) are a class of regulatory non-coding RNA molecules that are approximately 21-24 nucleotides long. They form unique short hairpin structures and are present in plants, animals, and viruses. miRNAs work through RNA silencing and post-transcriptional regulation of gene expression. Their sequence is complementary to regions within specific messenger RNAs (mRNAs). When the miRNA (in association with argonaute proteins of the RNA-Induced Silencing Complex [RISC]) binds to its mRNA target, the mRNA is either cleaved, destabilized, or its translation efficiency is reduced. This effect is critical in regulating gene expression in a cell-specific manner as many miRNAs are unique to explicit cell types, lineages, or disease states. The miRNA profile is often more precise and informative than the mRNA profile in characterizing developmental lineages. To this end, miRNA capabilities can be coopted to skew and molecularly sculpt teratomas down one lineage.

Teratomas are benign germ cell tumors containing a mix of tissues and organ components resembling normal derivatives of all germ layers. They are notorious for containing teeth, hair, nails, and bone. Teratomas modify their microenvironment to establish vasculature and obtain the necessary nutrients for development. This unique tumor may have the potential to be a microcosm for human development forming all functioning tissue types known in the developing human fetus. The teratoma may be engineered using miRNA vector constructs to grow single-lineage human tissues useful for drug screening, developmental biology studies, and, potentially, transplantation. This is a novel platform to better obtain human tissues for research.

An example vector construct utilizes an EF1-alpha promoter, GFP, IRES domain, and puromycin-resistance gene (EGIP) backbone that has been digested with ECORV-HF to excise out the GFP domain. A gBlock was amplified containing the Herpes Simplex Virus thymidine kinase (HSV-tk), 2A self-cleaving peptide, and GFP. The primers used to amplify the gBlock contain unique miRNA binding sites. The amplicon thus contains HSV-tk, 2A, and GFP flanked by a unique miRNA binding site. This amplicon was into the digested EGIP backbone using standard Gibson assembly. A schematic of the final construct can be seen in FIG. 1. The miRNA target sites, primers used, and gBlock sequence can be seen in Tables 1-3, 7 and 8. Editing efficiency of sgRNA are shown in Table 6.

Figure 2A:
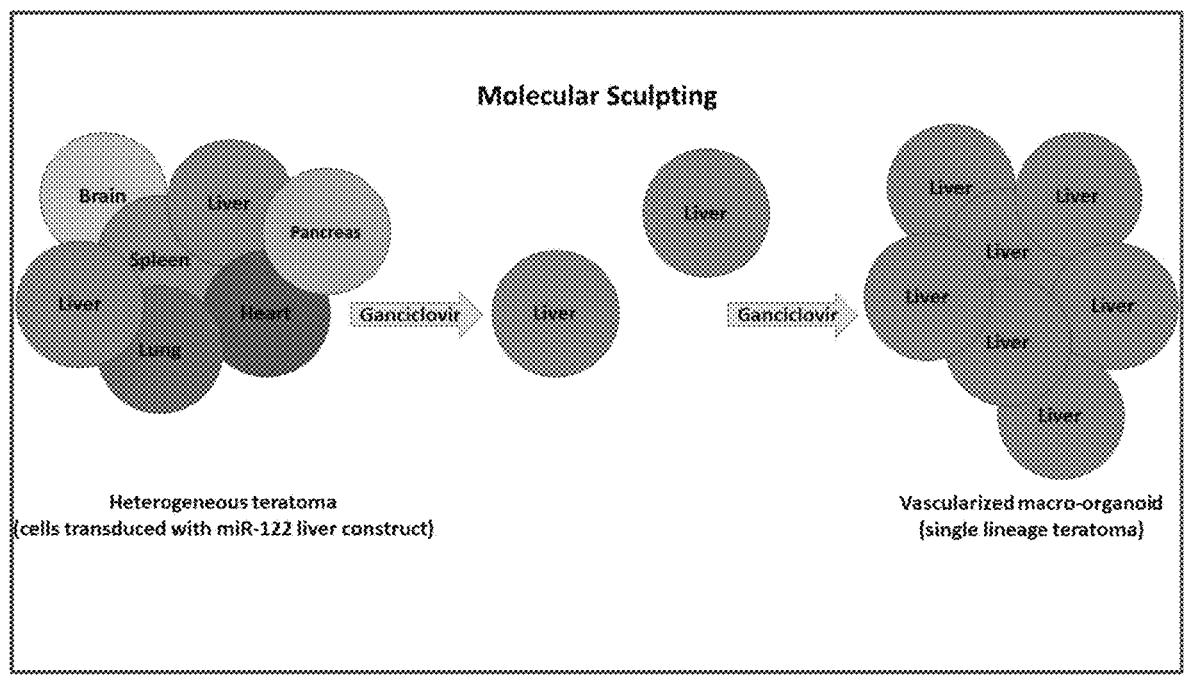
FIGS. 2A-2F.
Figures 2B, 2C, 2D, 2E, 2F:
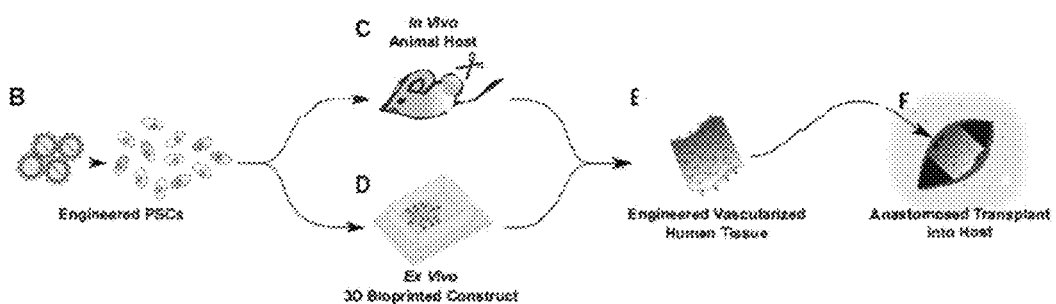
Figure 3:
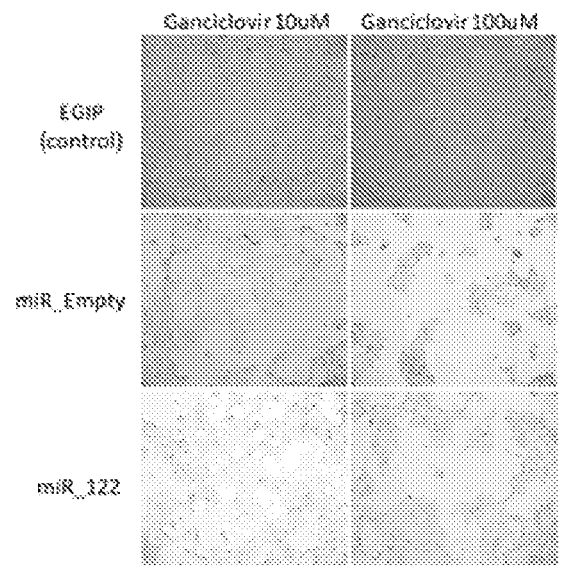
FIG. 3: HSV-tk killing test with Ganciclovir administration for 4 days in HEK293T cells.
Figure 4:
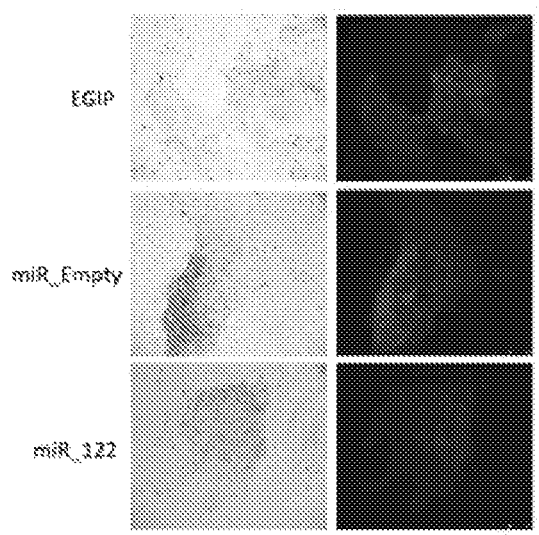
FIG. 4: H1 hESCs transduced with miRNA constructs.

Without being bound by theory, this novel technology can be explained as follows. The novel miRNA constructs all contain unique miRNA binding sites (e.g., miR-122: Liver, miR-124: Pan-neural, etc.) that determine which lineage the teratoma will exclusively follow as it grows. HEK293T cells are transfected with the miRNA constructs and lentiviral packaging vectors to produce miRNA lentivirus. This lentivirus is then transduced into H1 human embryonic stem cells (hESCs). After proper selection with puromycin for several days and confirmation that all cells fluoresce green through microscopy, enough hESCs are cultured for injection subcutaneously into Rag2 γC immunodeficient mice (at least $1 \times 10^6$ cells per injection). The injection is with miRNA construct-transduced hESCs in a 1:1 suspension of Matrigel® and mTeSR embryonic stem cell culture medium. It is a subcutaneous injection above the right flank. Once the teratoma becomes palpable, approximately 4-6 weeks after injection, the prodrug ganciclovir is administered to the mouse. The HSV-tk can begin to functionally phosphorylate ganciclovir causing the drug to be active in mammalian cells. Phosphorylated ganciclovir is a guanosine analog that incorporates into DNA causing senescence and cell death. Thus, without being bound by theory, all cells that divide and differentiate during teratoma growth and development will die as they contain HSV-tk, unless they are of the specific cell type that mirrors the unique miRNA binding sites transduced. For example, stem cells transduced with the miR-122 binding sites will only survive ganciclovir if they have developed into liver cells as only liver cells will contain miR-122. This is because miR-122 specific to liver cells will bind around the thymidine kinase region (which has been flanked with miR-122 binding sites) effectively silencing thymidine kinase expression allowing ganciclovir to pass through un- phosphorylated and not leading to liver cell death. Over time with constant administration of ganciclovir, a teratoma will form that is derived from a single lineage (e.g., liver). It will be, in essence, a vascularized macro-organoid that has been molecularly sculpted by the use of miRNAs, HSV-tk, and ganciclovir. A schematic of this process can be seen in FIG. 2. After successful growth, this single lineage human tissue can be analyzed by histological studies and single cell sequencing for validation of tissue type.

Example 2: Cell Fate Biasing Through Transcription Factor Overexpression

The derivation of various types of cells as well as complex tissue present in the human body is a critical need for regenerative medicine, drug development, disease research and the study of human biology. The availability of these diverse cells is limited from primary sources, and even if available have limited capacity for culture and expansion in vitro. On the other hand, human pluripotent stem cells (hPSCs) have the potential to differentiate into any mature human cell type and an almost unlimited capacity for in vitro culture. The use of these cells to derive mature cell fates as well as engineer complex tissue is an important challenge and will fulfill a critical need.

Figure 5:
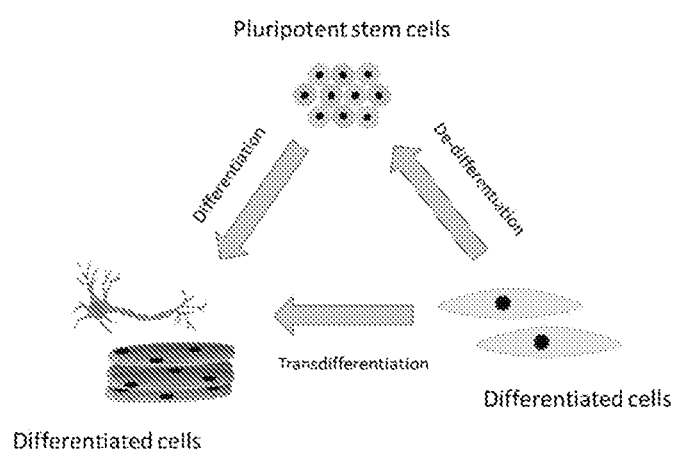
FIG. 5: Reprogramming landscape. Pluripotent stem cells can be differentiated to various lineages, differentiated cells can be transdifferentiated to other lineages, and differentiated cells can be de-differentiated to pluripotency by TF overexpression.

Overexpression of single or combinations of TFs can drive changes of the cell state (FIG. 5).

Applicants engineered an open reading frame (ORF)-based overexpression system that is capable of engineering or biasing cell fates. Using a lentiviral overexpression system, an exemplary case entails TF overexpression based differentiation of hPSCs to endothelial like cells by overexpression of ETV2. The overexpression of this TF combined with exposure to endothelial growth medium leads to rapid and efficient differentiation of hPSCs into endothelial like cells, as functionally validated (FIG. 6).

The demonstrated lentiviral system constitutively expresses the TF to drive differentiation. For tissue engineering applications, in order to have a temporally controllable differentiation process, a doxycycline inducible gene expression system is engineered. This system is enabled by an ORF expression cassette placed downstream of tetracycline response element repeats. This is combined with a Tet-On 3G system to drive doxycycline-induced gene expression.

Figures 7A, 7B:
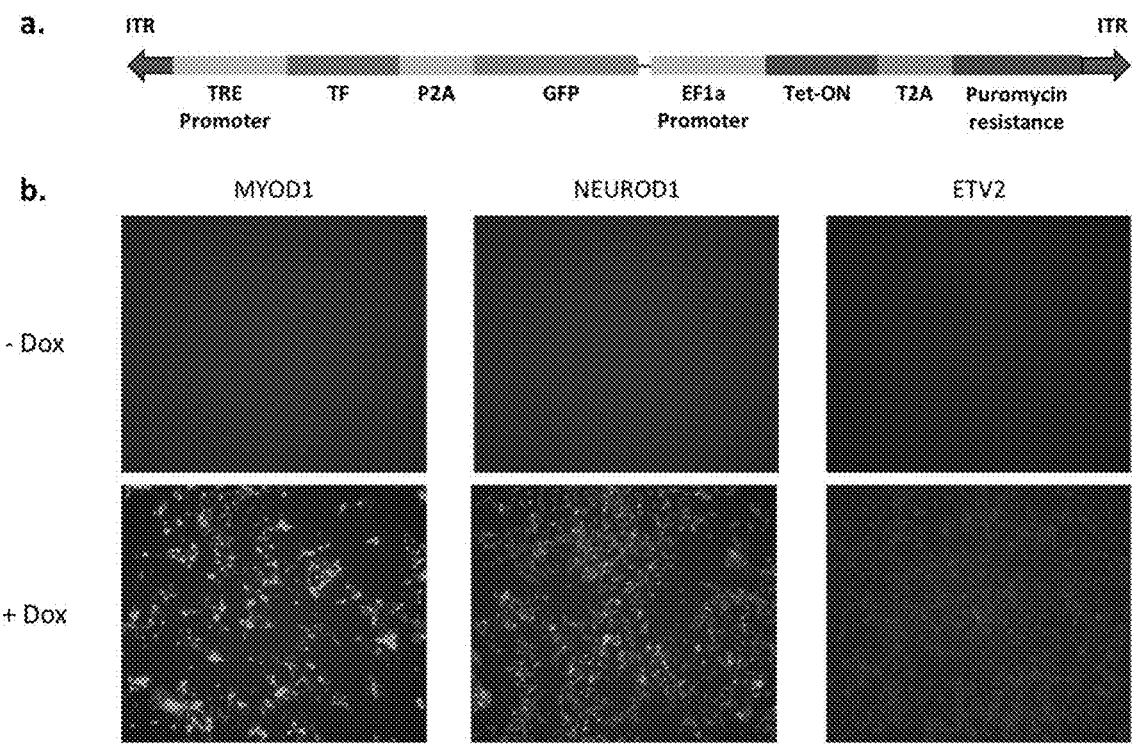
FIG. 7A-B: PiggyBac transposon based design and testing of ORF overexpression constructs. Construct design of dox-inducible TF overexpression vector between piggyBac transposon inverted terminal repeats (FIG. 7A). Transfection test of cloned constructs in HEK 293T cells. Overexpressed TFs are MYOD1, NEUROD1, ETV2 (FIG. 7B).

The combined system—ORF expression and Tet-ON 3G—has been cloned into a piggyBac transposon based system for integration into the target cell genome (FIG. 7). Transposons or transposable genetic elements are mobile genetic elements that can move positions in the genome. The piggyBac transposon was derived from the cabbage looper moth, *Trichoplusia ni*, and consists of conserved inverted terminal repeat regions between which transgenes can be inserted. Typically for cellular engineering applications, the transposon is delivered to the cell in a carrier vector along with the piggyBac transposase enzyme. The enzyme recognizes the inverted terminal repeats on the transposon and uses a 'cut-and-paste' mechanism to cut the transposon from the carrier vector and insert it into the genome in random TTAA locations. While the enzyme has both insertion and excision activity, engineered forms of the enzyme are available which preferentially insert the transposon into the genome and which have been codon optimized for expression in mammalian cells. The inducible activity of these vectors via transfection in human embryonic kidney (HEK) 293T cells has been demonstrated (FIG. 7).

Building on the system demonstrated using ORF based overexpression vectors, it can be applied to a CRISPR-Cas based gene activation systems. These systems harness the DNA recognition capability of the CRISPR-Cas system but use an inactivated version of the Cas enzyme so that there is no cleavage activity, instead fusing transcriptional activation domains to the Cas protein, enabling gene expression from endogenous loci which are recognized by the associated guide RNAs.

Figures 8A, 8B, 8C, 8D:
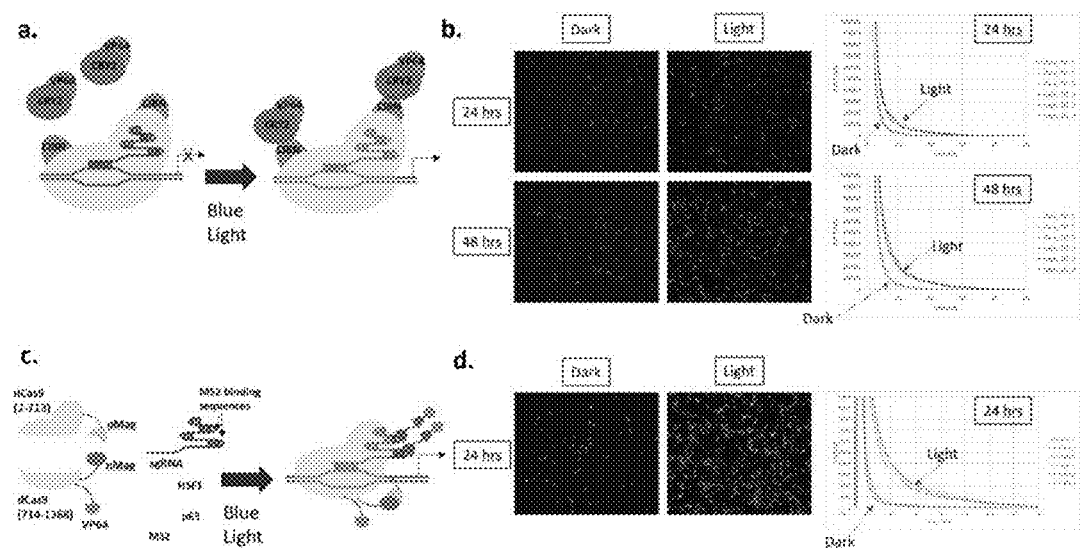
FIGS. 8A-8D: Optically actuated gene expression systems adapted for TF overexpression.

Additionally, optically controlled overexpression systems are engineered so as to obtain spatial control of overexpression to pattern differentiation and fate changes in a controlled manner. These systems use photodimerisable proteins typically derived from plant sources, such as the CRY2-CIB1 system derived from *Arabidopsis thaliana*. The two halves of such a photodimerisable protein are fused to two halves of transcriptional activators such that transcriptional programs are started only in the presence of the dimerising wavelength of light. Optically controlled gene expression systems are created from CRISPR-Cas systems, where one half of the photodimerisable protein is fused to the Cas protein while the other half is fused to a transcriptional activator, or alternately the Cas protein itself can be split in half and each of the photodimerisable proteins fused to one half. Similar systems have been demonstrated with ORF vectors where the Tet-On system is split and each half fused to photodimerising proteins. Optical activation of reporter fluorescent markers using CRISPR-Cas constructs adapted from the literature[20-22] have been demonstrated and are extended to optogenetic TF overexpression for tissue engineering applications (FIG. 8). These systems have been demonstrated in culture contexts, but not for tissue engineering and offer not only of temporal but also spatial control of cell fate changes.

To use these systems to create models of and transplantable human tissue, two platforms can be used. First, the previously described teratoma platform, where hPSCs containing inducible TF overexpression constructs are used for teratoma formation and the TFs are overexpressed to bias cell fate decisions toward particular lineages. Alternatively, TF overexpression in ex vivo tissue engineered constructs, such as 3D printed tissues where, again, TF overexpression is used to drive certain cell fates and optogenetically driven overexpression is harnessed to pattern biologically relevant geometries.

Teratoma Characterization

Figures 9A, 9B, 9C, 9D, 9E:
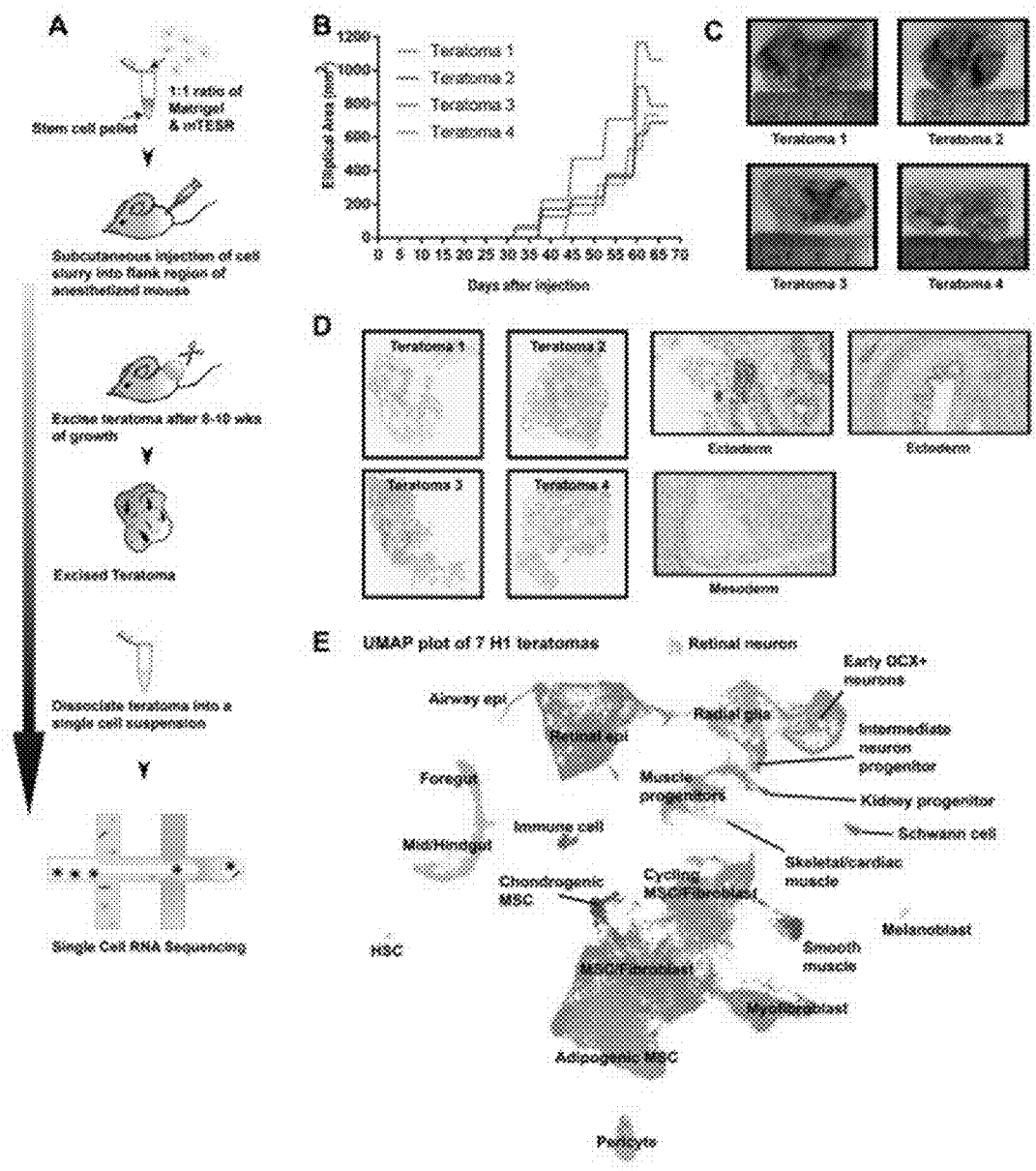
FIGS. 9A-9E: Teratoma Characterization.

Seven teratomas using H1 ESCs were generated and their cell types were characterized using both single cell RNA-seq and histology, with RNA FISH validation. To generate a teratoma, a subcutaneous injection of 5-10 million ESCs in a slurry of Matrigel® and embryonic stem cell medium was made in the right flank of anesthetized Rag2$^{-/-}$;γc$^{-/-}$ immunodeficient mice (FIG. 9A). Weekly monitoring of teratoma growth was made by quantifying approximate elliptical area (mm$^2$). Kinetic trajectories show an average time point of around 37 days when it is possible to outwardly see and measure tumor size. Growth continued for up to 70 days until the tumors were of a sufficient size for extraction and downstream analyses (~820 mm$^2$, FIG. 9B).

Figures 10A, 10B, 10C, 10D, 10E, 10F, 10G:
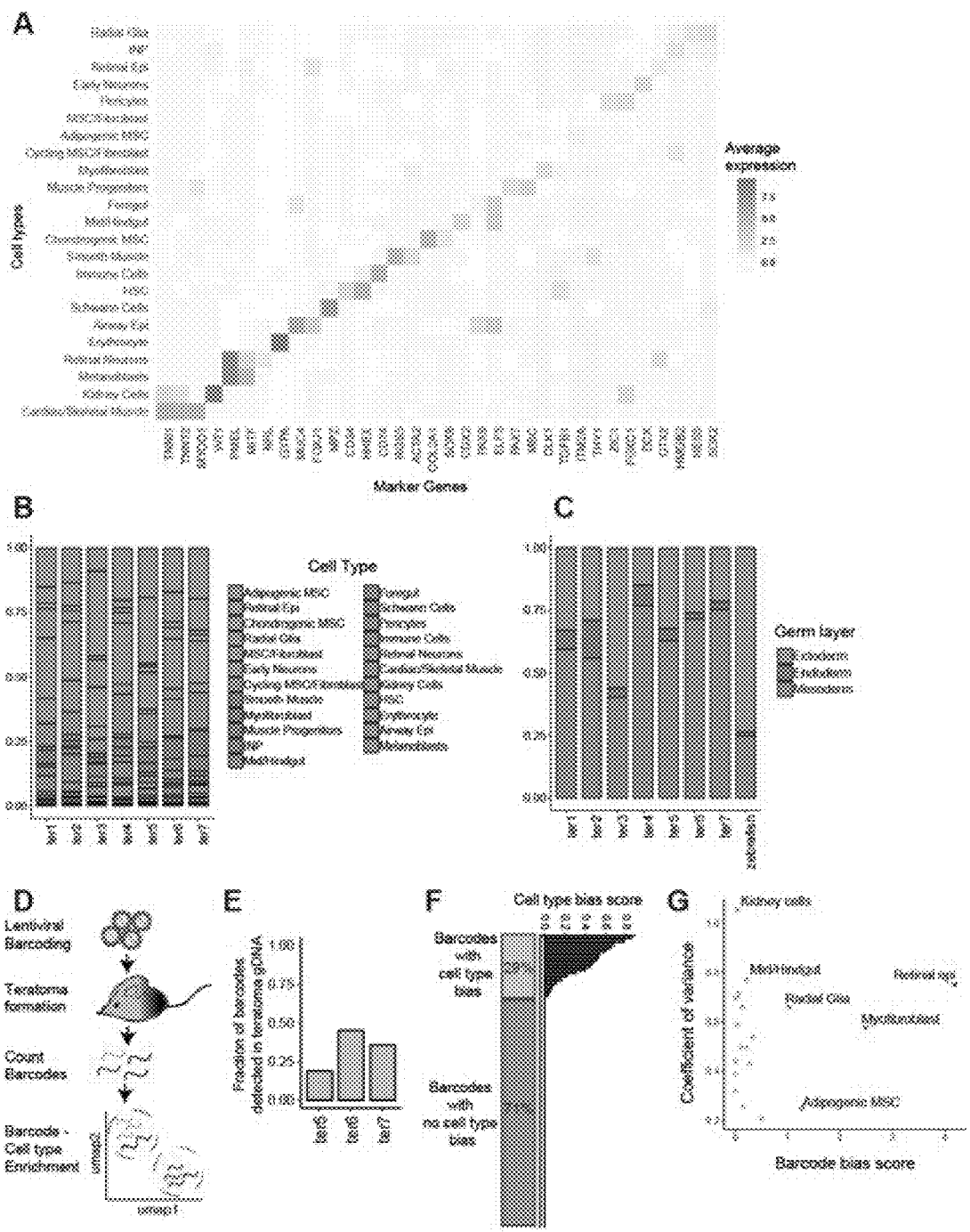
FIGS. 10A-10G: Heatmaps.

Post-extraction, tumors were observed for external heterogeneity (i.e. presence of dark pigmented regions, white tough areas, connective tissue, and vasculature) before being cut and frozen for sectioning and H&E staining (FIG. 9C). The presence of all 3 germ layers (ectoderm, mesoderm, endoderm) were validated to confirm pluripotency and developmental potential (FIG. 9D). Specific structures were consistently seen such as developing airways, retina, fetal cartilage and bone, muscle, vasculature, GI tract, and a predominance of connective tissue and neuroectoderm (FIGS. 16A-16K). Remaining tissue was dissociated down to the single cell level using GentleMACs™ for single-cell RNA sequencing with the droplet-based 10× genomics chromium platform[51]. A combined single cell gene expression matrix across the 7 teratomas for both human and mouse cells using the cellranger[51] pipeline from 10× genomics was generated. Any teratoma specific batch effects were removed by using the Seurat data integration pipeline[55], which uses mutual nearest neighbors and canonical correlation analysis to correct for batch specific effects, while retaining any batch specific cell types. With this batch-corrected matrix, the cells were clustered using a shared nearest neighbors (SNN) community detection algorithm[56], and generated a rough biological annotation of the clusters using a k-nearest neighbors classifier[57] trained on the Mouse Cell Atlas[58]. For the human clusters, the cluster annotations were further refined manually using canonical cell type markers (Table 5). Both the human and mouse cells were visualized with Uniform Manifold Approximation and Projection (UMAP)[59] scatterplot (data not shown). In the human cells, 23 cell types across all three germ layers, including endodermal cell types (foregut, mid/hindgut), and an abundance of mesodermal cell types were detected (data not shown). Each human cell type was validated by assessing the expression of key marker genes (FIG. 10A). In the mouse cells, invading immune cells, endothelial cells, and stromal cells were seen (data not shown).

Teratoma Bottlenecking and Heterogeneity

Heterogeneity present in and between teratomas assests with repeatability and utility of this model. The top marker genes for each cell type (FIG. 10A) and assessed the distribution of cell types represented in each individual teratoma (FIG. 10B) were calculated. The germ layer representation between teratomas to the standard zebrafish model were compared (FIG. 10C). The teratomas comprise a greater mesodermal population than the zebrafish. The zebrafish model has a greater ectodermal population than these teratomas.

One question in teratoma formation is how many cells engraft into the teratoma after stem cell injection. This is especially important in the context of using teratomas in perturbation screens, as one must ensure that enough cells contribute to the final tumor and ultimately a developmental screen. Severe bottlenecking can limit screen potential and teratoma utility. Thus, a lentiviral barcoding was used to assess the fraction of injected PSCs that engraft and go on to form the teratoma.

For 3 out of the 7 H1 ESC teratomas, prior to PSC injection, cells were transduced with an integrating lentiviral ORF barcode (FIG. 10D). The barcode consisted of a 25 random base pair sequence upstream of the lentiviral 3' long terminal repeat (LTR) region and a polyA tail, and can thus, be detected by scRNA-seq (FIG. 10A). In this way cells can be individually labeled prior to teratoma formation and teratoma cells that descend from these cells can be later captured via scRNA-seq. Transduced PSCs were evenly split: half for teratoma formation and half were frozen down for DNA sequencing. By comparing unique barcodes extracted from genomic DNA in these two cell populations the proportion of cells that engraft. Results show that across the three teratomas, about 25% of cells engraft can be calculated, out of a total of 10 million injected cells, which suggests that large scale perturbation screens are indeed feasible in teratomas (FIG. 10E).

Barcodes were tracked in individual cells by amplifying the expressed barcode from scRNA-seq. Since cells from the teratoma with the same barcode originated from the same PSC, it was possible to track whether certain PSCs were primed to develop into certain lineages. With this, we saw in general there is little biasing occurring with 79% of barcodes being equally distributed to all cell lineages represented (FIG. 10F). For each cell type, a barcode bias score was computed, which reflects the level to which barcodes tend to be enriched or depleted in that cell type (FIG. 10G). A teratoma variance score was computed for each cell type, which reflects how much the proportion of that cell type varies across teratomas and plotted the correlation of the teratoma variance score with the barcode bias score (FIG. 10G). It was observed that retinal epithelium has both a high teratoma variance, and a high barcode bias (FIG. 10G). Some cell types are represented equally in all teratomas processed (MSCs) while others have a higher degree of variability in each teratoma (kidney cells) (FIG. 10G, FIG. 10B).

Stem Cell Line Potential via Teratoma Chimeras

To ensure these studies can be performed with many stem cell lines with similar pluripotency and developmental potential 4 embryonic stem cell lines were pooled together in equal ratios prior to injection for chimeric teratoma formation. Lines were later tracked via cell line-unique single nucleotide polymorphisms (SNPs). HUES62, PGP1, H9, and H1 cell lines were mixed in equal ratios and injected to create chimeric teratomas. The proportion of cells profiled with scRNA-seq belonging to each cell line can be assessed and the UMAP plot of transcriptome profiles from cells isolated from chimeric teratomas can be visualized. Cell line identities were then overlaid on UMAP plots to determine relative contributions of each cell line to the final teratoma.

Teratoma Maturity and Fidelity

The stage in embryonic development in the teratoma was deferred to ascertain to determine its applicability and relevance as a tool for modeling. These results may vary drastically depending on time and/or size allowed for growth and size/species of animal used to form the human teratoma. These results are derived from the teratomas all being allowed to grow for a maximum of 70 days in $Rag2^{-/-};\gamma c^{-/-}$ immunodeficent mice.

Figures 18A, 18B, 18C, 18D, 18E, 18F:
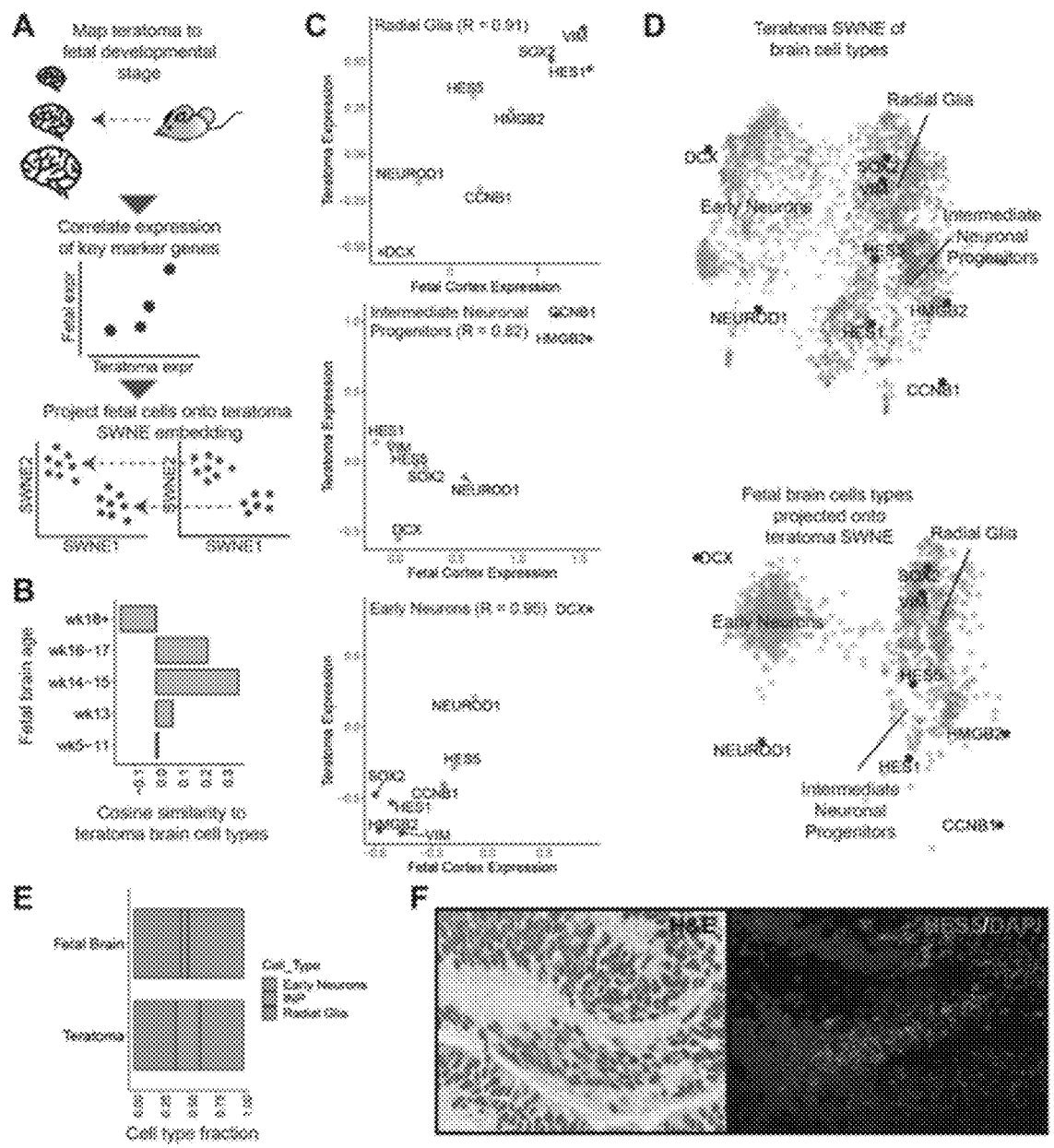
FIGS. 18A-18F.

Due to the semi-random nature of teratoma differentiation, it is possible that different cell types will resemble different stages of embryonic development. Thus, individual tissue types were separately staged, initially analyzing the neural subtypes present including radial glia, intermediate neuronal progenitors, and early neurons. Staging and validating teratoma neural subtypes was performed utilizing the same cell types from a published fetal brain dataset[60]. The cosine similarity metric was used to compare the average expression of all cells belonging to neural subtypes with the average expression of the same subtypes in the fetal brain dataset at different stages of development. The teratoma neuronal cells were most similar to the fetal human brain at weeks 14-15 (FIG. 18B). To assess the similarity of these neuronal cell types to the fetal brain cell types, a panel of neuronal cell type marker genes were used: DCX, NEUROD1, HESS, CCNB1, SOX2, HMGB2, VIM, and then correlated the expression of these marker genes between the teratoma cells and fetal brain cells for every neuronal cell type (FIG. 18A, FIG. 18C). A fairly high correlation overall, with R=0.91 for radial glia, R=0.82 for intermediate neuronal progenitors, and R=0.95 for early neurons was found. Similarity Weighted Nonnegative Embedding (SWNE) visualizations of the teratoma neural cells were generated, and projected the fetal data set onto the teratoma SWNE (FIG. 18A, FIG. 18D)[61]. Briefly, SWNE embeds single cell gene expression data in two dimensions, similar to t-SNE and UMAP, while preserving more of the global structure and enabling genes to be visualized alongside the cells. The closer an embedded gene is to a group of cells, the higher the expression level of that gene in those cells[61]. Similar cell types map to similar spatial positions in the SWNE embedding, although the teratoma SWNE embedding is not able to resolve the fetal intermediate neuronal progenitors and radial glia as well FIG. 18D). The cell type proportions in the fetal brain were compared, showing that the teratoma has a higher proportion of intermediate neuronal progenitor cells (FIG. 18E).

Figures 19A, 19B, 19C, 19D, 19E, 19F:
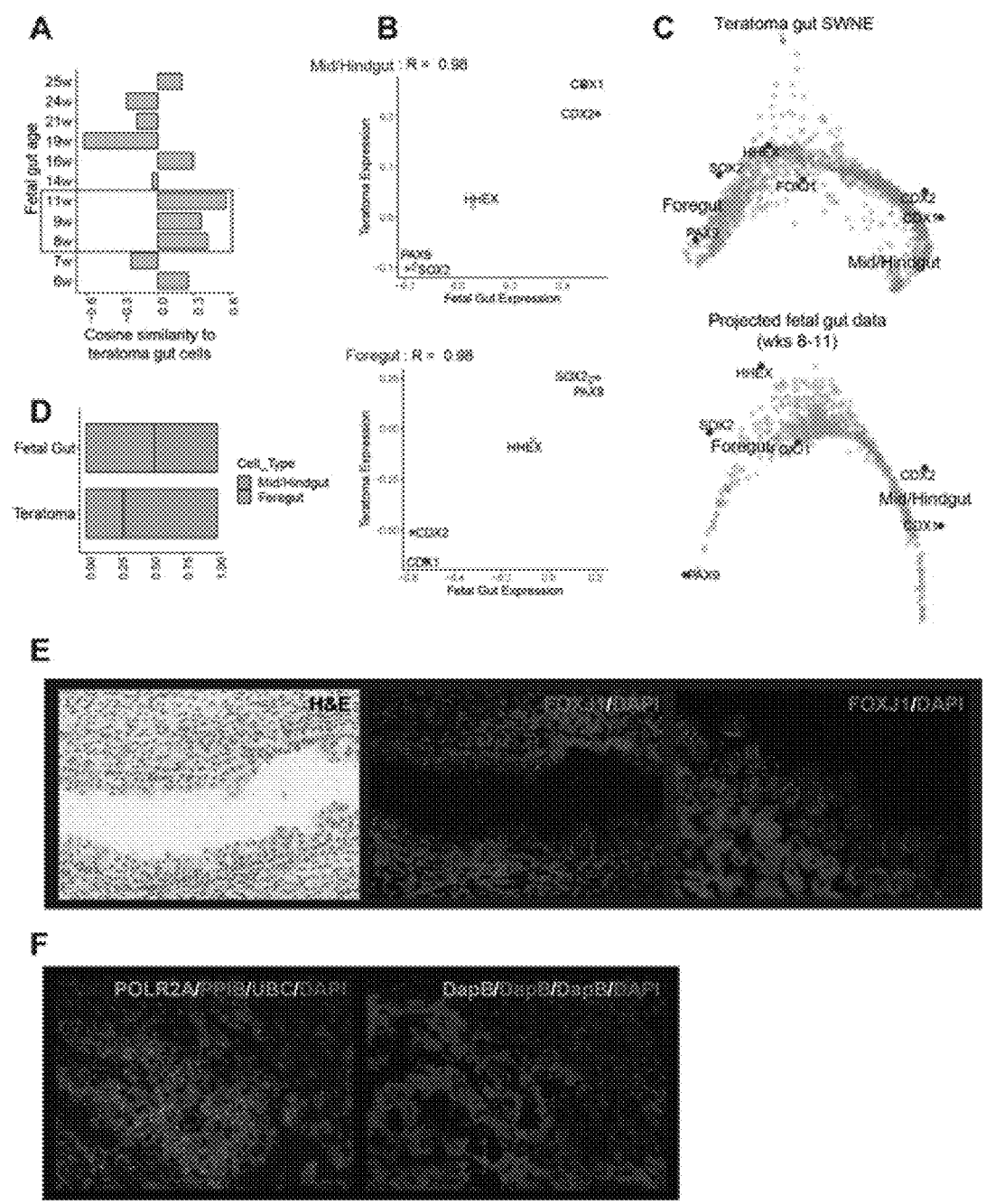
FIGS. 19A-19F: Teratoma characterization.

This analysis was similarly performed with teratoma gut subtypes using a published fetal gut dataset as reference[62]. The teratoma gut cells were most similar to week 8-11 fetal gut age (FIG. 19A). Marker genes for gut cell types (CDX1, CDX2, HHEX, FOXJ1, PAX9, SOX2) between teratoma and fetal cells were used and found a high overall correlation, with an R=0.96 for foregut and R=0.97 for mid/hindgut (FIG. 19B). The projection of fetal gut data onto the teratoma SWNE again shows relatively similar spatial positioning (FIG. 19C). Interestingly, different embryonic stages were seen in development depending on tissue type analyzed, suggesting teratoma development is asynchronous. Without being bound by theory, it is postulated that since the teratoma dataset is largely neural in origin, this tissue type may be permitted longer time for development and maturity. Conversely, the gut subtypes may appear later in teratoma development and thus, in smaller proportions with less maturation. When looking at the proportion of foregut vs mid/hindgut across the teratoma and fetal gut, the teratoma produces less foregut and more mid/hindgut (FIG. 19D).

Figures 17A, 17B, 17C, 17D:
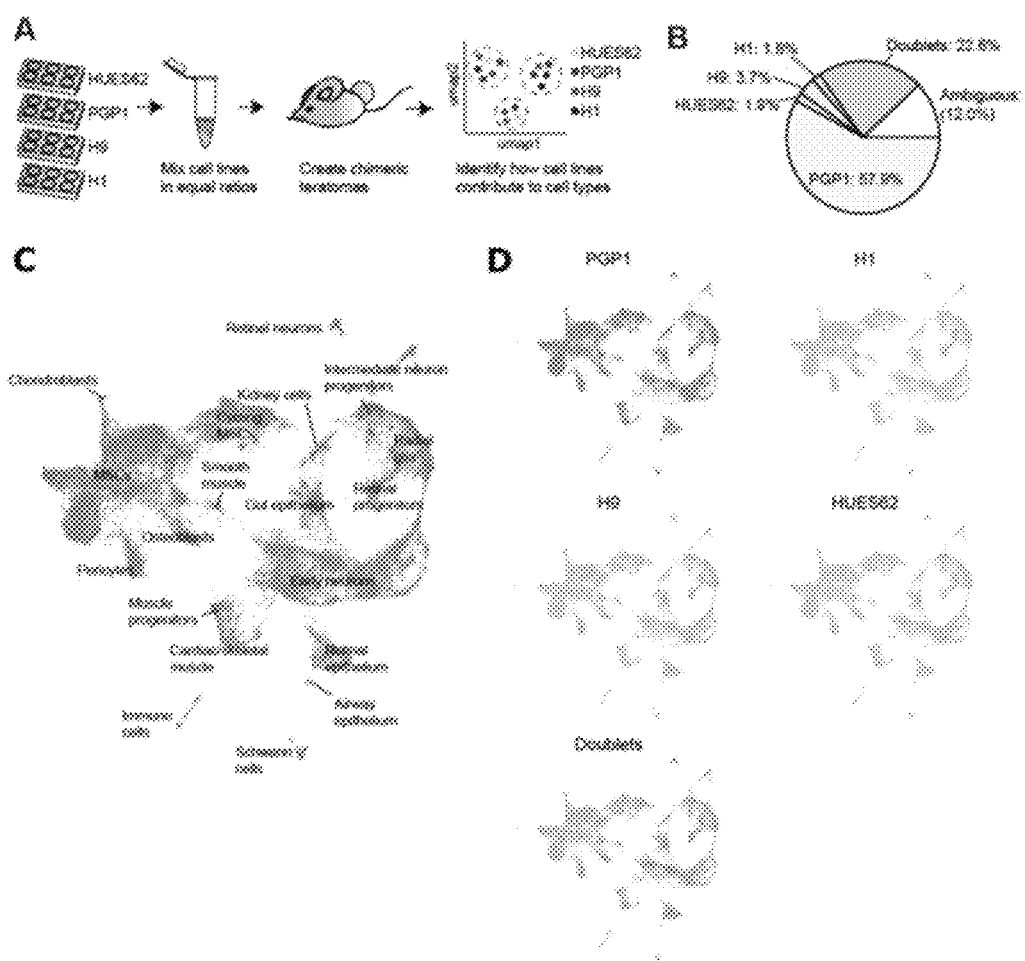
FIGS. 17A-17D.

The presence of cell subtypes was further validated utilizing RNAScope® ISH technology. The radial glia marker HESS was probed which showed high abundance in regions of neuroectoderm in fixed teratoma tissue sections (FIG. 18F). Additionally, FOXJ1 (marker for cilia) was probed and by imaging a speculative airway in a teratoma tissue section, visualized high abundance of FOXJ1 lining the airway, using POLR2A, PPIB, and UBC as positive controls (FIG. 18F. FIG. 17E). These studies encompass a deeper characterization of the teratoma in terms of embryonic staging and validation of cell types present.

Three-Dimensional Developmental Screen Utilizing the Teratoma

Figures 11A, 11B, 11C, 11D:
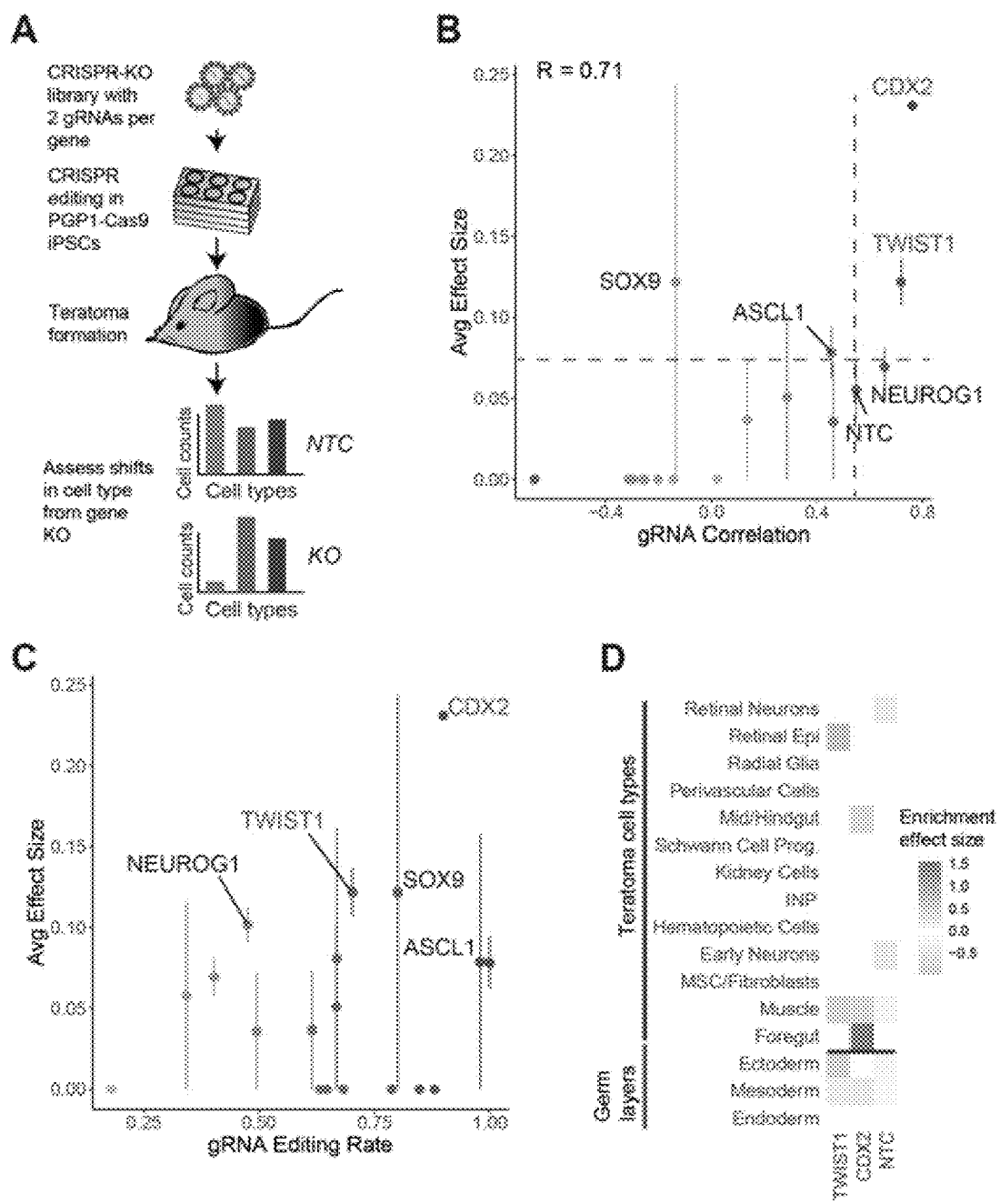
FIGS. 11A-11D.

The teratoma as a developmental model was validated by performing a single-cell genetic perturbation screen utilizing CRISPR/Cas9. Thus, one can determine whether the teratoma correctly models cell fate specification and lineage permissibility. A list of 24 major organ/lineage specification genes were compiled that are embryonically lethal upon knockout in mice via literature review. Studying the effects of these genes using cell lines or organoid models would require different experiments and different models for each cell lineage. With the teratoma model, once can screen the effects of these genetic perturbations in all major lineages in the same experiment. Utilizing the CROPseq-Guide-Puro vector backbone, 48 individual single guide RNAs (sgRNAs) directed at each developmental gene (2 sgRNAs per gene)[63] were cloned. After creating a pooled lentiviral library with these sgRNAs, a stable Cas9-expressing induced PSC (IPSC) line (PGP1) was transduced at a MOI of 0.1, so that each cell received approximately one perturbation. After selection, these cells were injected subcutaneously into 3 Rag2$^{-/-}$;γc$^{-/-}$ immunodeficient mice for teratoma formation, extraction, and downstream scRNA-seq processing with 10× genomics (FIG. 11A).

Figures 20A, 20B, 20C, 20D:
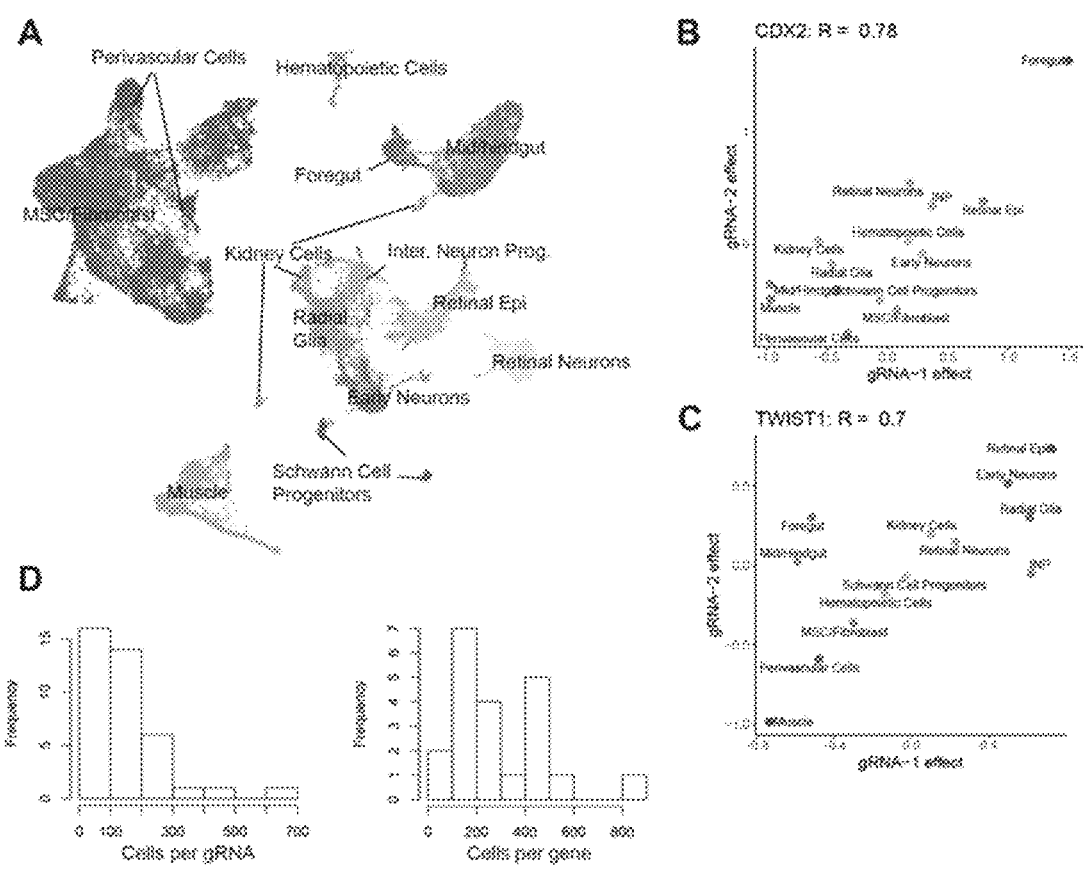
FIGS. 20A-20D.
Figure 21A:
FIGS. 21A-21B: Lentiviral barcodes.
Figure 21B:
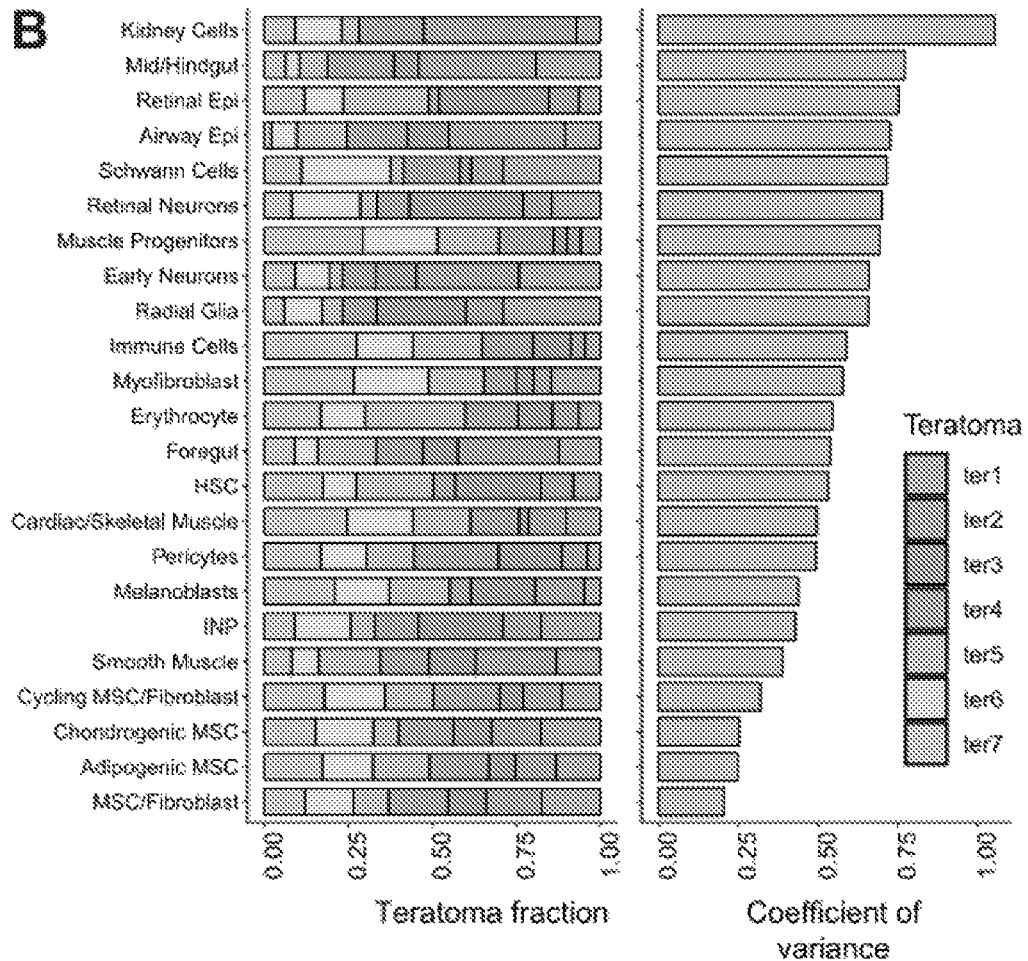
Figures 22A, 22B, 22C, 22D:
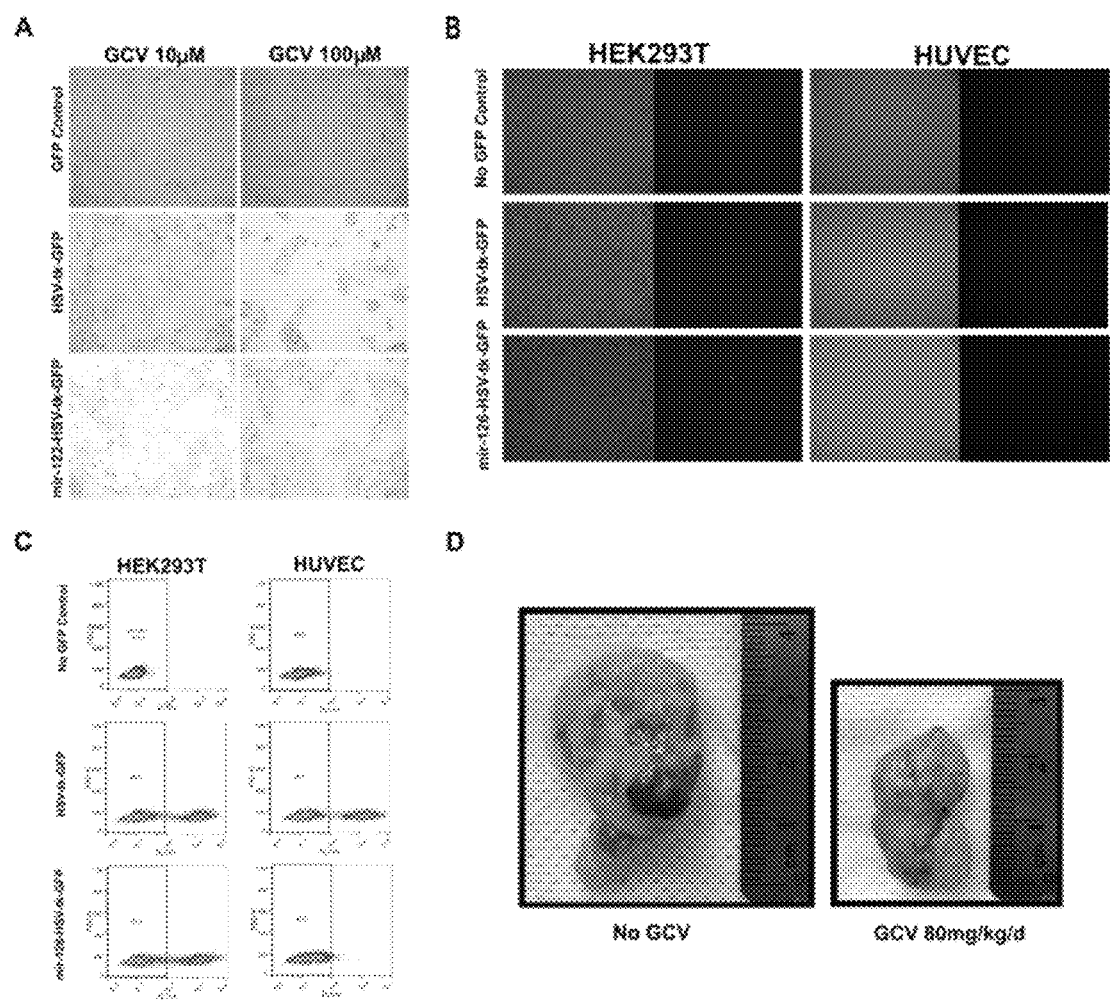
FIGS. 22A-22D.
Figures 23A, 23B, 23C:
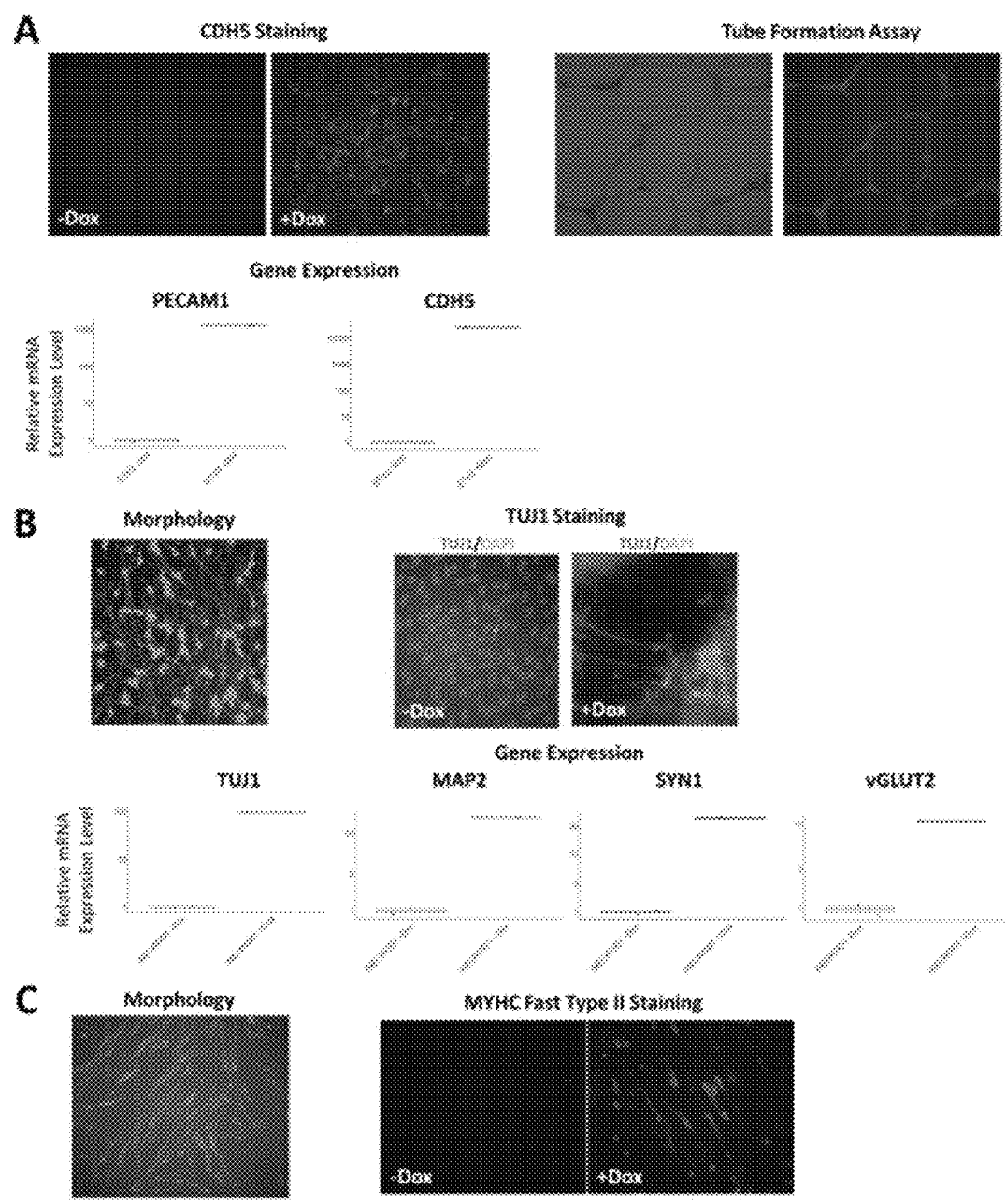
FIGS. 23A-23C: TR validation.
Figure 24A:
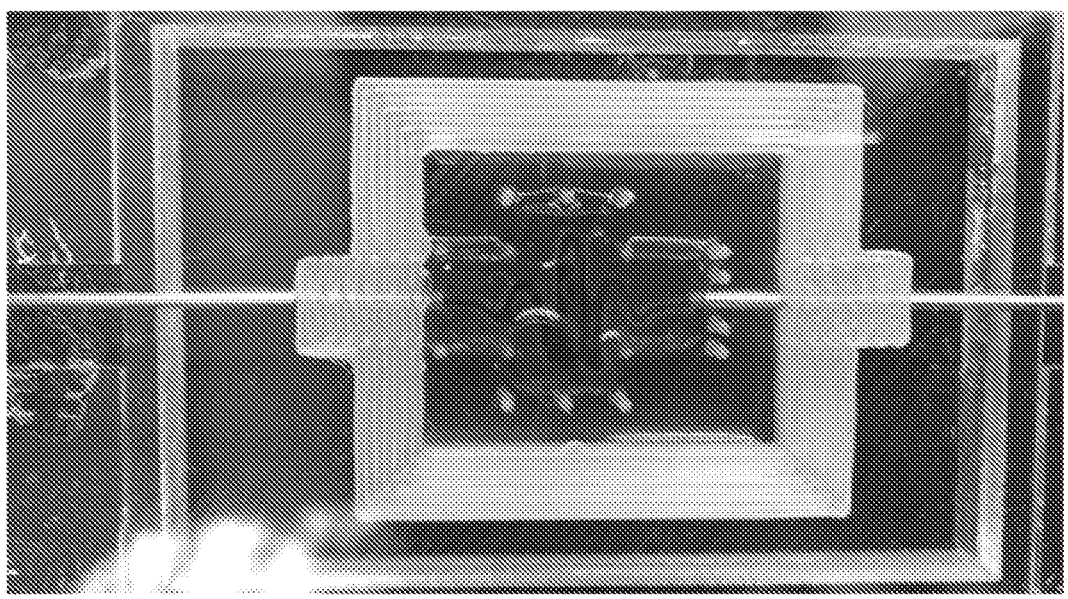
FIGS. 24A-24B: Long-term tissue construct.
Figure 24B:
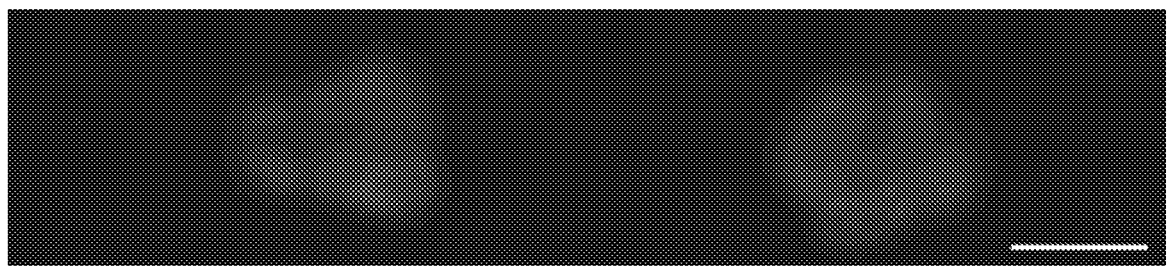
Figure 25:
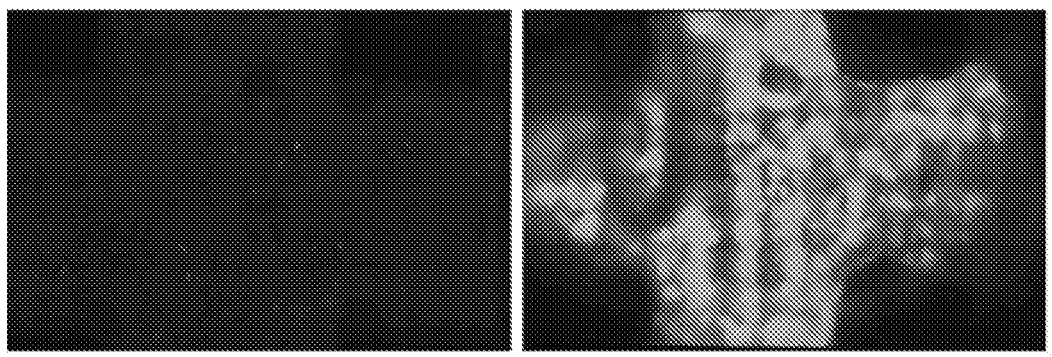
FIG. 25: Example of widefield microscopy image cell growth within a printed construct.
Figure 26:
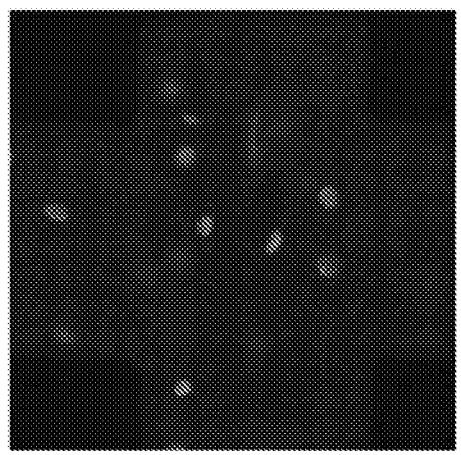
FIG. 26: Example of cell growth from spheroids within a printed construct.
Figure 26:
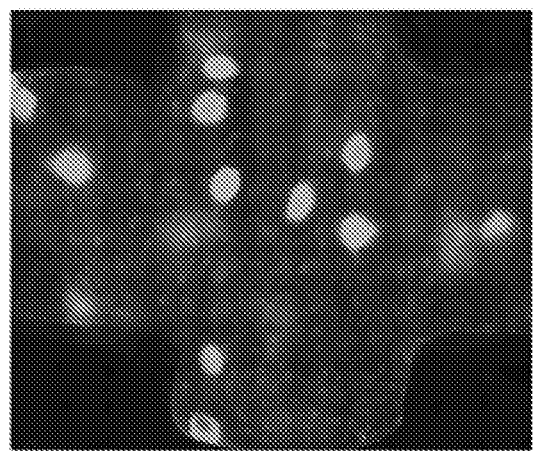

Cell types in the PGP1 teratoma cells were called using a kNN classifier trained on the H1 teratoma data. Cell types with fewer than 100 cells were collapsed into their closest neighboring cell type, and the resulting cell types were visualized using a UMAP plot (FIG. 11B). Cell type enrichment and/or depletion was assessed based on gene knockout using a ridge regression model (FIG. 11A). Regression analysis was run at both the gene and gRNA level, generating regression coefficients that represent the effects of each gene/gRNA knockout on cell type enrichment/depletion. P-values for each gene coefficient were computed by shuffling gene assignments and generating a null distribution. A significance threshold of p=0.01 was set and all gene coefficients with a larger p-value were set to zero. A median of 218 cells per gene and 112 cells per sgRNA were captured (FIG. 20D). For each gene, the average effect of each gene knockout on cell type enrichment/depletion was computed by summing the absolute value of all significant coefficients for that gene across cell types, as well as the Pearson correlation of the coefficients for the two gRNAs targeting that gene giving a sense of both the effect size and reproducibility of each gene knockout. Plotting the average effect size the gRNA correlation shows that gene knockouts with strong effect sizes tend to be more reproducible (R=0.79) (FIG. 11B). A bootstrap standard deviation for each effect size was computed, shown in the error bars for the effect size axis, which further suggests that gene knockouts with large effect sizes and high gRNA correlations tend to be robust to resampling (FIG. 11B). CDX2 and TWIST1 showed a significantly larger effect size and gRNA correlation than the NTC controls and directed our studies further (FIG. 11B). Additionally, the editing efficiencies of all our guide RNAs were validated, showing that genes that had a large effect size and gRNA correlation also had relatively high editing rates (FIG. 11C). Specifically, CDX2 and TWIST1 had average editing efficiencies of 0.89 and 0.70 respectively (FIG. 11C, data not shown).

CDX2 is a known major organ specification gene for the development of the midgut and hindgut[64,65]. Interestingly, the data shows that cells containing a CDX2 knockout are shifting away from midgut/hindgut tissues with enrichment in foregut (FIG. 11D). This has been shown in past literature that CDX2 knockout shifts the differentiation pathway away from intestine and instead promotes gastric activation[66,67]. TWIST1 also showed a large effect size in this screen and is a known transcription factor for epithelial-to-mesenchymal transition important in development as well as disease such as metastatic cancers[68,69]. Interestingly, this screen validates such findings as cells containing a TWIST1 knockout are shifting away from muscle (mesenchymal tissue) and enriching for retinal epithelium (FIG. 11D). Studies have shown the importance of TWIST1 for mesodermal specification and differentiation[70]. A more detailed plot of all the effects of CDX2 and TWIST1 knockouts was created (FIG. 20B, FIG. 20C). Overall, these results help validate the teratoma as a tool to study human development and potentially understand novel biology that would otherwise be difficult to research.

Molecular Sculpting of the Teratoma Through miRNAs

Finally, a single lineage in the developing teratoma was enriched. Endogenously expressed micro RNAs (miRNAs) were used.

The construct utilizes an EGIP backbone (EF1-alpha promoter/GFP/IRES domain/puromycin-resistance gene) with a gBlock cloned in containing the Herpes Simplex Virus thymidine kinase (HSV-tk) suicide gene, 2A self-cleaving peptide, and GFP all flanked by a unique miRNA binding site of choice (FIG. 1A).

The novel miRNA-HSV-tk constructs contain unique miRNA binding sites (i.e. miR-122:Liver, miR-124:Pan-neural) which determine the enrichment for the developing teratoma upon administration of ganciclovir (GCV) to the host. GCV is a guanosine analog that becomes incorporated into the genome of dividing cells only upon phosphorylation by HSV-tk and thus, halts DNA replication causing cell death to cells engineered with HSV-tk while leaving surrounding wild-type cells unaffected[76-79]. If the dividing and differentiating ESCs in the teratoma have reached a desired lineage and begin to endogenously express the miRNA of interest, that miRNA will silence the construct allowing cell survival and continued growth (and depletion of GFP fluorescence) even in the presence of GCV. However, there will be continued killing of undesired lineages (FIG. 1B).

miRNA-HSV-tk constructs were tested in vitro in the H1 ESC line. The functionality of the suicide gene HSV-tk was assessed in the presence of GCV. After the H1 line was properly transduced and selected with either our miRNA-HSV-tk construct or a GFP control (EGIP backbone alone), GCV (10 μM) was added to the media. After 5 days of culturing cells in the presence of GCV, those transduced with the miRNA-HSV-tk construct showed total cell death where the GFP control cells were unaffected becoming confluent (FIG. 1C). Furthermore, the unique miRNA specificity of the constructs was assessed based on cell type. A cell type that faithfully expresses the miRNA of interest and a control cell type that was transduced. HeLa cells are cervical carcinoma cells that express miR-21 which is highly specific to cancers[73,80-82]. HEK293T cells are embryonic kidney cells that show little to no expression of miR-21 and should therefore serve as a control[83-85]. After transduction of each cell line with our miR-21-HSV-tk construct, the cells were cultured for 5 days and then imaged and performed flow cytometry analysis. Strikingly, a loss in GFP expression in the HeLA cells expressing the miR-21-HSV-tk construct was observed, but not in the HEK293T cells (FIG. 1D, 1E). This would indicate that the GFP expression was silenced by the endogenously expressing miR-21 in HeLa cells. The 2 cell lines also were transduced with an HSV-tk construct lacking any miRNA binding sites, and both cell lines showed continued GFP expression even after 5 days.

Applicant then tested the miRNA-HSV-tk constructs in vivo with the goal to grow a teratoma that is enriched for a desired lineage. For this task the miR-124-HSV-tk construct was selected to enrich for the neural lineage. After the H1 ESC line was successfully transduced and selected for the miR-124-HSV-tk construct, cells were subcutaneously injected into Rag2$^{-/-}$;γc$^{-/-}$ immunodeficient mice and allowed to form teratomas as described above. Once teratomas reached a minimum of 1 cm in diameter, intratumoral injections with GCV (80 mg/kg/d) for half to tumors began until they grew an appropriate time for extraction (~10 weeks).

Figures 6A, 6B, 6C, 6D, 6E:
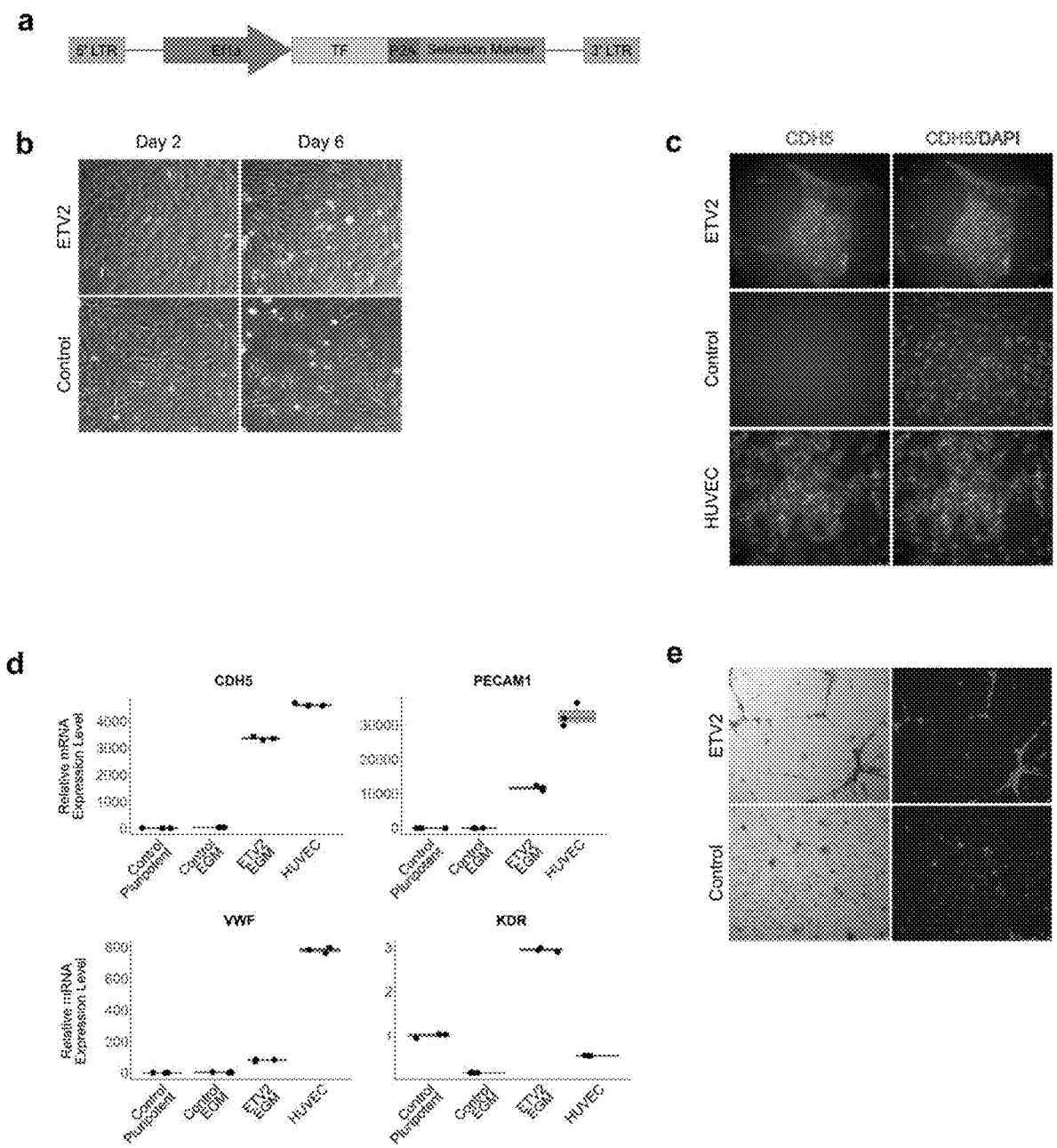
FIGS. 6A-6E: Design of lentiviral TF overexpression vector and validation of reprogramming of hPSCs to endothelial-like cells by ETV2 overexpression.

Post-extraction, tumors were observed for external heterogeneity. Strikingly the tumor that received intratumoral GCV injections was of a smaller size and appeared less heterogeneous than the tumor without GCV injections (FIG. 6D). Upon single cell RNA-seq analysis of the tumors, enrichment in cell-type fraction for early neurons, neuronal progenitors, Schwann cells, and foregut in the tumor receiving GCV injections were seen. In addition, depletion in muscle, retinal pigmented epithelium, and many other cell types was observed (FIG. 1F). These data suggest that GCV in combination with our miR-124-HSV-tk construct allowed for proper selection and enrichment for neural populations within the teratoma compared to tumors not in the presence of daily GCV administration. However, enrichment for foregut was also observed. To the best os Applicant's knowledge, there is no known published literature on miR-124 having a role in foregut development.

Discussion

Developmental biology has utilized in vitro systems such as cell line models and organoids, as well as animal models to elucidate key properties of human embryogenesis and organogenesis. Some of most recent progress has come from organoid systems to better model human development and disease yet limitations still exist (i.e. tissue maturity, thickness, scalability, and efficiency)[19,20,86].

The teratoma has the potential to be a multilineage model for human development. A few studies have opted to use the teratoma as a tool to derive rare cell types such as muscle progenitors and hematopoietic stem cells[46-50].

In this study, it is shown that the teratoma can give rise to a vast array of cell types and lineages from radial glia to ciliated respiratory epithelium using scRNA-seq analysis, histological H&E staining, and RNAScope® ISH studies. The frequency and proportion of cells and delineate potential cell biasing that may occur through lentiviral barcoding strategies was determined. Multiple stem cell lines can give rise to teratomas with similar heterogeneity. Additionally, some of these tissue types were developmentally staged based on published datasets from past literature and validate that the teratoma develops cell types similar to what is seen in fetal human data. A developmental knockout screen was performed within the teratoma utilizing CRISPR/Cas9 to demonstrate the utility of the teratoma as a multilineage model. Interestingly, a robust response with CDX2 and TWIST1 knockout stem cells was observed. Not only did these gene knockouts cause a robust response, but they were biologically accurate (i.e. CDX2 knockouts showed depletion in midgut/hindgut and enrichment in foregut). Not only does this validate the teratoma as a model but can be a means to utilize the teratoma in discovering novel biology through additional screens and disease modeling. Finally, to enrichment for the neural lineage in teratomas via the miRNA circuit and administration of GCV in vivo displaying an enrichment for early neurons, neuronal progenitors, Schwann cells, and foregut was clone. These data could be beneficial in future functional studies in drug screening, developmental biology, disease modeling, tissue engineering, and eventual transplant studies.

The strengths in this system lie in the teratoma's ability to generate large numbers of cells from all major germ layers in a 3D context that are relatively faithful to human development. With this system Applicant has captured rare cell types such as the highly sought after hematopoietic stem cell, in addition to Schwann cells that have shown difficulty in formation with neuronal organoid systems[28,47-50]. The Schwann cell population can even be enriched for using this miRNA circuit. This model can also potentially access multiple stages in development depending on the time allowed for growth and extraction. Earlier extraction time points may lead to a pool of more embryonic progenitor cell types and delayed extraction will access mature adult cell types. The researcher can also enrich for desired cell types based on injection site (i.e. muscle, liver, and brain). Previous studies have extracted the teratoma as early as 3 weeks to access progenitors and the tumors were allowed to grow in the muscle to enrich for myogenic cell types[46]. In addition, this model can be easily manipulated via miRNA circuits or additional strategies to grow/enrich a specific tissue of interest in vivo.

Cell Fate Biasing Through Transcription Factor Overexpression

The derivation of various types of cells as well as complex tissue present in the human body is a critical need for regenerative medicine, drug development, disease research and the study of human biology. The availability of these diverse cells is limited from primary sources, and even if available have limited capacity for culture and expansion in vitro. On the other hand, human pluripotent stem cells (hPSCs) have the potential to differentiate into any mature human cell type and an almost unlimited capacity for in vitro culture. The use of these cells to derive mature cell fates as well as engineer complex tissue is an important challenge and will fulfill a critical need.

Cellular reprogramming by the overexpression of transcription factors (TF), has widely impacted biological research, from the direct conversion of adult somatic cells[91,92] to the induction of pluripotent stem cells[93-98], and the differentiation of hPSCs[99-104]. Overexpression of single or combinations of TFs can drive these changes of the cell state (data not shown).

An open reading frame (ORF) based overexpression system has been engineered which is capable of engineering or biasing cell fates. Using a lentiviral overexpression system, an exemplary case of TF overexpression based differentiation of hPSCs to endothelial like cells by overexpression of ETV2 was demonstrated. The overexpression of this TF combined with exposure to endothelial growth medium leads to rapid and efficient differentiation of hPSCs into endothelial like cells which we have functionally validated (FIG. 12).

The demonstrated lentiviral system constitutively expresses the TF to drive differentiation. For tissue engineering applications, in order to have a temporally controllable differentiation process we have engineered a doxycycline inducible gene expression system. This system is enabled by an ORF expression cassette placed downstream of tetracycline response element repeats. This is combined with a Tet-On 3G system to drive doxycycline-induced gene expression.

The combined system—ORF expression and Tet-ON 3G—has been cloned into a piggyBac transposon based system for integration into the target cell genome (data not shown). Transposons or transposable genetic elements are mobile genetic elements which can move positions in the genome. The piggyBac transposon was derived from the cabbage looper moth, *Trichoplusia ni*, and consists of conserved inverted terminal repeat regions between which transgenes can be inserted. Typically for cellular engineering applications, the transposon is delivered to the cell in a carrier vector along with the piggyBac transposase enzyme. The enzyme recognizes the inverted terminal repeats on the transposon and uses a 'cut-and-paste' mechanism to cut the transposon from the carrier vector and insert it into the genome in random TTAA locations. While the enzyme has both insertion and excision activity, engineered forms of the enzyme are available which preferentially insert the transposon into the genome and which have been codon optimized for expression in mammalian cells. Applicant has demonstrated the inducible activity of these vectors via transfection in human embryonic kidney (HEK) 293T cells (data not shown).

While Applicant has demonstrated this using ORF based overexpression vectors, it is anticipated that such fate biasing will be feasible with CRISPR-Cas based gene activation systems. These systems harness the DNA recognition capability of the CRISPR-Cas system, but use an inactivated version of the Cas enzyme so that there is no cleavage activity, instead fusing transcriptional activation domains to the Cas protein, enabling gene expression from endogenous loci which are recognized by the associated guide RNAs[105-108]. As compared to the ORF based systems, CRISPR activation systems offer more scalability and ease of use, but on the other hand do not offer control over expression of targeted isoforms and expression of mutant versions of genes.

Additionally, optically controlled overexpression systems can be engineered such that one can also have spatial control of overexpression to pattern differentiation and fate changes in a controlled manner. These systems use photodimerisable proteins typically derived from plant sources, such as the CRY2-CIB1 system derived from *Arabidopsis thaliana*. The two halves of such a photodimerisable protein are fused to two halves of transcriptional activators such that transcriptional programs are started only in the presence of the dimerising wavelength of light. Optically controlled gene expression systems can be created from CRISPR-Cas systems, where one half of the photodimerisable protein is fused to the Cas protein while the other half is fused to a transcriptional activator, or alternately the Cas protein itself can be split in half and each of the photodimerisable proteins fused to one half. Similar systems have been demonstrated with ORF vectors where the Tet-On system is split and each half fused to photodimerising proteins. Optical activation of reporter fluorescent markers using CRISPR-Cas constructs adapted from literature[109-111] and are implementing optogenetic TF overexpression for tissue engineering applications have been demonstrated (FIG. 8). These systems have been demonstrated in culture contexts, but not for tissue engineering and offer not only of temporal but also spatial control of cell fate changes.

To use these systems to create models of and transplantable human tissue, two systems are used. The previously described teratoma platform, where hPSCs containing inducible TF overexpression constructs are used for teratoma formation and the TFs are overexpressed to bias cell fate decisions toward particular lineages. Alternately, one can also use TF overexpression in ex vivo tissue engineered constructs, such as 3D printed tissues where, again, TF overexpression will be used to drive certain cell fates and optogenetically driven overexpression can also be harnessed to pattern biologically relevant geometries.

Example No. 4—3D Bioprinting of Vascularized Ex Vivo Tissues

The methods of creating ex vivo tissue for regenerative purposes described previously, including the techniques for developmental screening and miRNA-catalyzed enrichment, may be extended to be applied in ex vivo, perfusable 3D-printed tissue constructs. A number of viable 3D-printing methods exist that may fit the requirements for this application.

In general, the 3D-printed tissue construct consists of a hydrogel matrix that encapsulates cells of a desired type, contains one or more hollow lumens allowing for perfusion, and is perfused within a chamber that allows for interstitial flow, and at a flow rate high enough to allow for dense cell growth. A schematic of a 3D-printed tissue construct is shown in FIG. 13 and induced pluripotent stem cell masses grown within a 3D-printed tissue construct were grown. Cell types in this case will consist of induced pluripotent stem cells, or embryonic stem cells, with any of the modifications described in the previous methods.

The hydrogel matrix can be composed of synthetic or biological polymers, examples of which include polyethylene glycol, hyaluronic acid, alginate, collagen, gelatin, and fibrin. The hydrogel matrix may also be composed of commercially available extracellular matrix substitutes, such as Matrigel®, a solubilized basement membrane preparation. The hydrogel matrix may also be composed of any combination of the materials, or chemically modified variants of the materials described above. Examples of chemically modified variants include gelatin methacrylate or hyaluronic acid methacrylate. In particular, methacrylated variants of polymers will polymerize in response to light, while fibrin will polymerize when exposed to the enzyme thrombin. An example of a viable matric composition would be 10 mg/mL gelatin, 4 mg/mL Matrigel®, and 7.5 mg/mL fibrin.

Hollow lumens within the matrix can be generated via encapsulation and evacuation of a scaffold material, such that the scaffold material is initially solid when encapsulated, but will liquefy in response to certain changes in the surrounding physical or chemical environment. Potential materials that exhibit this type of behavior include poly (vinyl alcohol), Pluronic™ F127 (a nonionic, surfactant polyol), and blends of alginate/Pluronic™ F127. Poly (vinyl alcohol) can be printed into 3D scaffolds via fused-filament printing techniques, is solid phase when dry, but will dissolve in aqueous environments, including that of a hydrogel. Pluronic™ F127 can be extruded into 3D scaffolds via extrusion printing techniques, is gel-phase at room temperature, and will transition to liquid phase at approximately 4 degrees Celsius. A blend of alginate/Pluronic™ F127 is solid phase following exposure to solutions of calcium ions (20 mM or above) at room temperature, and will transition to liquid phase and dissolve when exposed to a combination of the alginate lyase enzyme and 4 degrees Celsius. Lumen sizes will typically range from 100 µm to 2 mm.

The chamber housing the printed construct must be created such that it allows for interstitial flow through the matrix. Typically, this only requires that the sides of the matrix are not completely enclosed in solid walls (data not shown).

Figure 14:
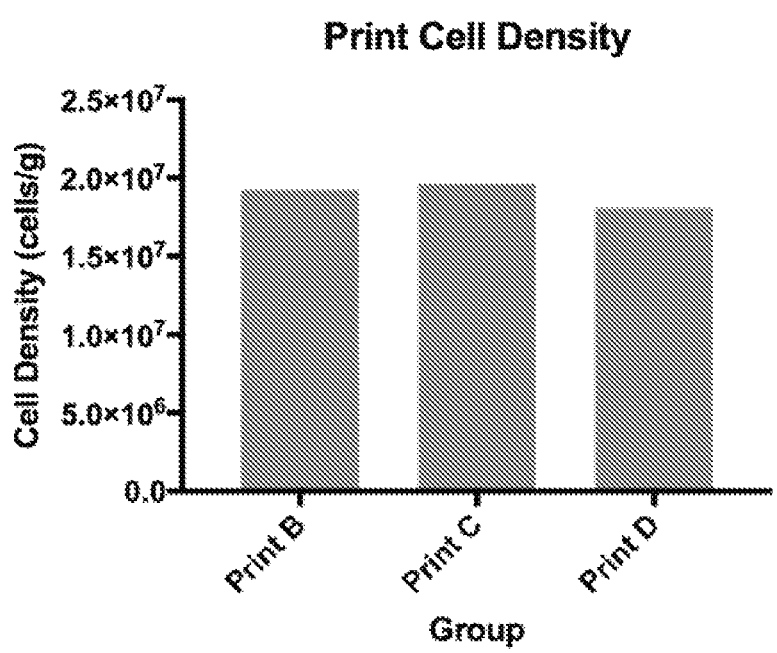
FIG. 14: Print cell density.

Flow rates in these systems will typically need to be 500 uL/min or greater in order to sustain the necessary cell growth and cell density. A highly dense matrix can be considered to have cell densities exceeding 15 million cells/mL. Multiple matrices have been created that have been capable of achieving this degree of cell density. This is shown in FIG. 14. MDA-MB-231 cancer cells were grown this way (data not shown).

Vascularization of Organoids Ex Vivo

Engineering tissues via in vivo teratoma development can be a powerful approach because of advanced multi-lineage tissue differentiation. The teratoma microenvironment can generate adult-like tissues that develop beyond what is possible via ESC self-organization in vitro, i.e. organoid technologies. This may in part be attributed to in vivo host vascularization of the developing tissue, as thick tissues require a source of vasculature to nourish the cells deep within the tissue construct.

However, utilizing the teratoma to generate human transplantable tissues may raise the concern of xenograft contamination and rejection, as the teratoma tissue currently is grown in a mouse host. Thus, methods to recapitulate teratoma development in vitro are critical. A main focus towards this effort would be to vascularize self-organized tissue ex vivo.

Figures 15A, 15B:
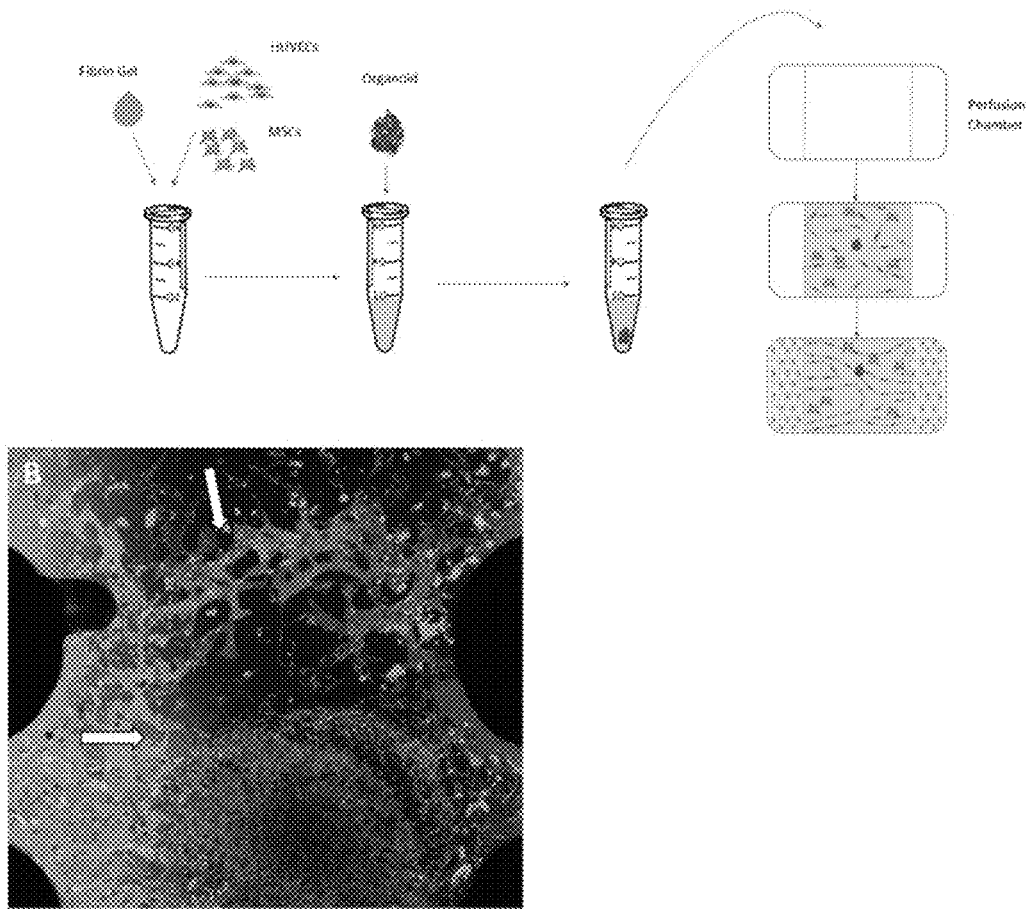
FIGS. 15A-15B: Proposed perfusable culture system for ex vivo developing tissue construct via in vitro organoid and vascular coupling.
Figures 16A, 16B, 16C, 16D, 16E, 16F, 16G, 16H, 16I, 16J, 16K, 16L, 16M:
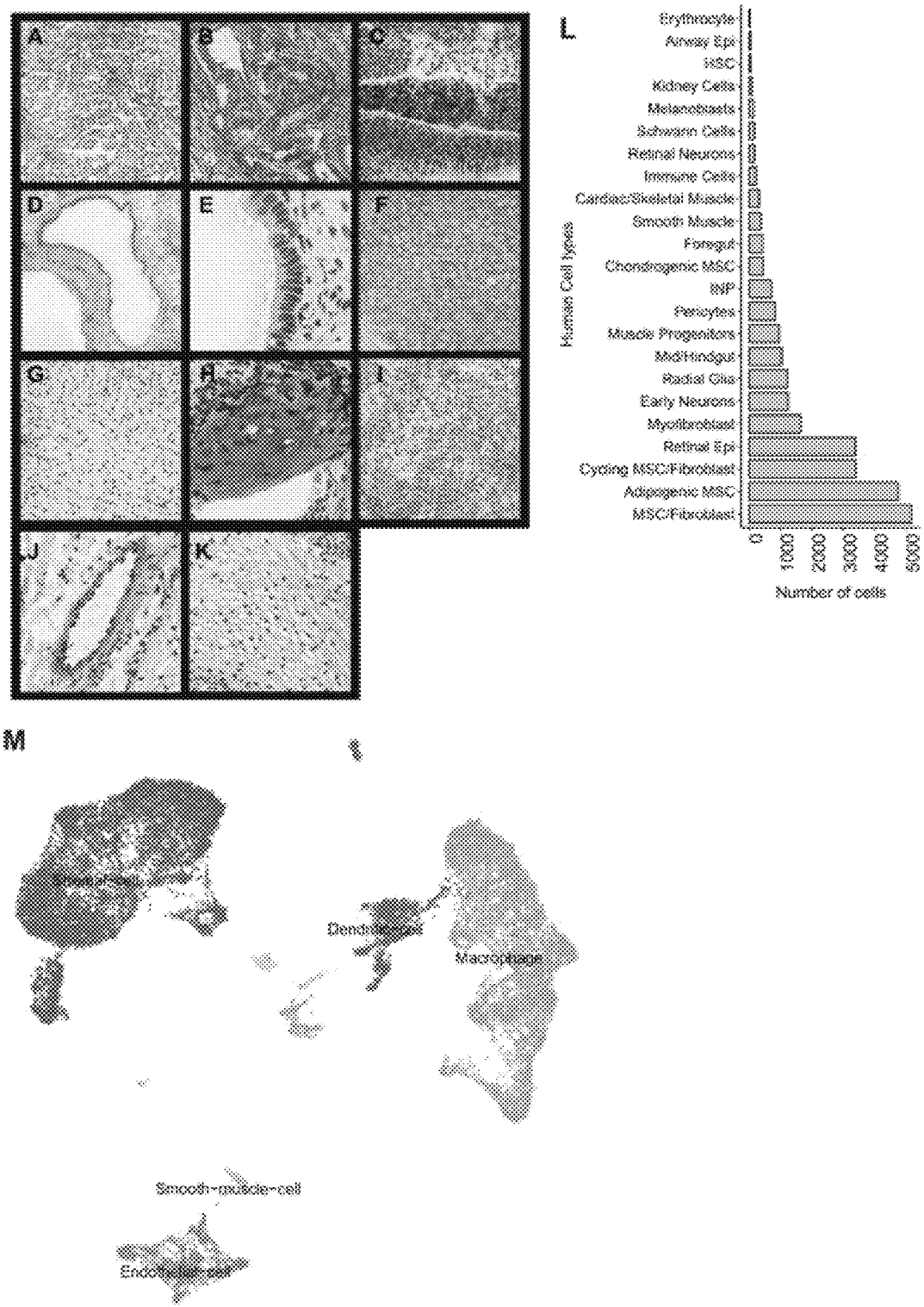
FIGS. 16A-16M: H&E stains. H& E stains of the (FIG. 16A) Choroid plexus (FIG. 16B) Fetal neuroectoderm (FIG. 16C) Retinal pigmented epithelium (FIG. 16D) Developing airway (FIG. 16E) Ciliated respiratory epithelium (FIG. 16F) Fetal cartilage.

Following a gel and cell density composition like that described in previous studies[112] a self-organized vascular network can be generated that will serve as a vascular bed to provide nutrients to tissues generated in vitro (FIG. 15). This is done by formulating a fibrin gel (3 mg/ml), with HUVECs (6 million cells/ml), and MSCs (1.5 million cells/ml), and then adding an organoid of choice to the gel-cell suspension before deposition into a perfusion chamber (FIG. 15A). An HUVEC-MSC organ bud was built as described in previous work[113] (data not shown). This perfusion chamber is a 3D-printed PDMS constructed adapted from the Lewis group.[114]

Following 10 days of static culture, patent and perfusable vessels are built in the fibrin gel and are partly coupled with the organ-bud (FIG. 15B). This is demonstrated by perfusing media spiked with FITC labelled dextran through the vascular network. A percentage of the vascular network that is coupled with the organ-bud is being perfused with the media, which offers support of this system being used to eventually nourish and culture ex vivo generated tissues long-term.

EQUIVALENTS

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control. Throughout this specification, technical literature is referenced by an author citation, the complete bibliographic details for which are provided below.

TABLE 1 miRNA Target Sites and Specificities (SEQ ID NOS 1-5, respectively)

| miRNA | Specificity | Target Site |
|---|---|---|
| miR-21 | Pluripotent Stem Cells / Tumors | TCAACATCAGTCTGATAAGCTA |
| miR-122 | Liver | CAAACACCATTGTCACACTCCA |
| miR-124 | Neural | GGCATTCACCGCGTGCCTTA |
| miR-126 | Endothelial Cells | CGCATTATTACTCACGGTACGA |
| miR-302A | Pluripotent Stem Cells | AGCAAGTACATCCACGTTTAAGT |

TABLE 2

Primer sequences (SEQ ID NOS 6-17, respectively)

| | |
|---|---|
| miR_Empty_F | TGGCTAGTTAAGCTTGATATCGAATTCCTGCAGC CCGGGGGATCCAGATCACACCGGTCGCCA |
| miR_Empty_R | GGGAGAGGGGGGGGGGCGGAATTCCGCGGGCCC GTCGACGCGGTTAACGCCGCTTTACTTGTACAG |
| miR_21_F | TGGCTAGTTAAGCTTGATATCGAATTCCTGCAGC CCGGGGGATCCTCAACATCAGTCTGATAAGCTA AGATCACACCGGTCGCCA |
| miR_21_R | GGGAGAGGGGGGGGGGCGGAATTCCGCGGGCCC GTCGACGCGGTTTAGCTTATCAGACTGATGTTGA AACGCCGCTTTACTTGTACAG |
| miR_122_F | TGGCTAGTTAAGCTTGATATCGAATTCCTGCAGC CCGGGGGATCCCAAACACCATTGTCACACTCCAA GATCACACCGGTCGCCA |
| miR_122_R | GGGAGAGGGGGGGGGGCGGAATTCCGCGGGCCC GTCGACGCGGTTTGGAGTGTGACAATGGTGTTTG AACGCCGCTTTACTTGTACAG |
| miR_124_F | TGGCTAGTTAAGCTTGATATCGAATTCCTGCAGC CCGGGGGATCCGGCATTCACCGCGTGCCTTA AG ATCACACCGGTCGCCA |
| miR_124_R | GGGAGAGGGGGGGGGGCGGAATTCCGCGGGCCC GTCGACGCGGTTTAAGGCACGCGGTGAATGCC A ACGCCGCTTTACTTGTACAG |
| miR_126_F | TGGCTAGTTAAGCTTGATATCGAATTCCTGCAGC CCGGGGGATCCCGCATTATTACTCACGGTACGA AGATCACACCGGTCGCCA |
| miR_126_R | GGGAGAGGGGGGGGGGCGGAATTCCGCGGGCCC GTCGACGCGGTTTCGTACCGTGAGTAATAATGCG AACGCCGCTTTACTTGTACAG |
| miR_302A_F | TGGCTAGTTAAGCTTGATATCGAATTCCTGCAGC CCGGGGGATCCAGCAAGTACATCCACGTTTAAGT AGATCACACCGGTCGCCA |
| miR_302A_R | GGGAGAGGGGGGGGGGCGGAATTCCGCGGGCCC GTCGACGCGGTTACTTAAACGTGGATGTACTTGC T AACGCCGCTTTACTTGTACAG |

TABLE 3 gBlock sequence (HSV-tk_2A_GFP).

ATGGCTTCGTACCCCTGCCATCAACACGCGTCTGCGTTCGACCAGGCTGC

GCGTTCTCGCGGCCATAGCAACCGACGTACGGCGTTGCGCCCTCGCCGGC

AGCAAGAAGCCACGGAAGTCCGCCTGGAGCAGAAAATGCCCACGCTACTG

CGGGTTTATATAGACGGTCCTCACGGGATGGGGAAAACCACCACCACGCA

ACTGCTGGTGGCCCTGGGTTCGCGCGACGATATCGTCTACGTACCCGAGC

CGATGACTTACTGGCAGGTGCTGGGGGCTTCCGAGACAATCGCGAACATC

TACACCACACAACACCGCCTCGACCAGGGTGAGATATCGGCCGGGGACGC

GGCGGTGGTAATGACAAGCGCCCAGATAACAATGGGCATGCCTTATGCCG

TGACCGACGCCGTTCTGGCTCCTCATATCGGGGGGAGGCTGGGAGCTCA

CATGCCCCGCCCCGGCCCTCACCCTCATCTTCGACCGCCATCCCATCGC

CGCCCTCCTGTGCTACCCGGCCGCGCGATACCTTATGGGCAGCATGACCC

CCCAGGCCGTGCTGGCGTTCGTGGCCCTCATCCCGCCGACCTTGCCCGGC

ACAAACATCGTGTTGGGGGCCCTTCCGGAGGACAGACACATCGACCGCCT

TABLE 3-continued gBlock sequence (HSV-tk_2A_GFP).

GGCCAAACGCCAGCGCCCCGGCGAGCGGCTTGACCTGGCTATGCTGGCCG
CGATTCGCCGCGTTTACGGGCTGCTTGCCAATACGGTGCGGTATCTGCAG
GGCGGCGGGTCGTGGCGGGAGGATTGGGGACAGCTTTCGGGGACGGCCGT
GCCGCCCCAGGGTGCCGAGCCCCAGAGCAACGCGGGCCCACGACCCCATA
TCGGGGACACGTTATTTACCCTGTTTCGGGCCCCCGAGTTGCTGGCCCCC
AACGGCGACCTGTACAACGTGTTTGCCTGGGCCTTGGACGTCTTGGCCAA
ACGCCTCCGTCCCATGCACGTCTTTATCCTGGATTACGACCAATCGCCCG
CCGGCTGCCGGGACGCCCTGCTGCAACTTACCTCCGGGATGGTCCAGACC
CACGTCACCACCCCCGGCTCCATACCGACGATCTGCGACCTGGCGCGCAC
GTTTGCCCGGGAGATGGGGGAGGCTAAC<u>GGATCCGGCGCAACAAACTTCT</u>
<u>CTCTGCTGAAACAAGCCGGAGATGTCGAAGAGAATCCTGGACCGA</u>*TGGTG*
*AGCAAGGGCGAGGAGCTGTTCACCGGGGTGGTGCCCATCCTGGTCGAGCT*
*GGACGGCGACGTAAACGGCCACAAGTTCAGCGTGTCCGGCGAGGGCGAGG*
*GCGATGCCACCTACGGCAAGCTGACCCTGAAGTTCATCTGCACCACCGGC*
*AAGCTGCCCGTGCCCTGGCCCACCCTCGTGACCACCCTGACCTACGGCGT*
*GCAGTGCTTCAGCCGCTACCCCGACCACATGAAGCAGCACGACTTCTTCA*
*AGTCCGCCATGCCCGAAGGCTACGTCCAGGAGCGCACCATCTTCTTCAAG*
*GACGACGGCAACTACAAGACCCGCGCCGAGGTGAAGTTCGAGGGCGACAC*
*CCTGGTGAACCGCATCGAGCTGAAGGGCATCGACTTCAAGGAGGACGGCA*
*ACATCCTGGGGCACAAGCTGGAGTACAACTACAACAGCCACAACGTCTAT*
*ATCATGGCCGACAAGCAGAAGAACGGCATCAAGGTGAACTTCAAGATCCG*
*CCACAACATCGAGGACGGCAGCGTGCAGCTCGCCGACCACTACCAGCAGA*
*ACACCCCCATCGGCGACGGCCCCGTGCTGCTGCCCGACAACCACTACCTG*
*AGCACCCAGTCCGCCCTGAGCAAAGACCCCAACGAGAAGCGCGATCACAT*
*GGTCCTGCTGGAGTTCGTGACCGCCGCCGGGATCACTCTCGGCATGGACG*
*AGCTGTACAAGTAA* (SEQ ID NO: 18)

HSV-tk is bold. 2A is <u>underlined</u>. GFP is *italicized*.

TABLE 4

Other Polynucleotide Sequences

| Polynucleotide | Sequence |
| --- | --- |
| EGF1-α (GenBank Accession No. J04617.1, nucleotides 373-1582) | CGTGAGGCTCCGGTGCCCGTCAGTGGGCAGAGCGCACATCGCC CACAGTCCCCGAGAAGTTGGGGGGAGGGGTCGGCAATTGAACC GGTGCCTAGAGAAGGTGGCGCGGGGTAAACTGGGAAAGTGATGT CGTGTACTGGCTCCGCCTTTTTCCCGAGGGTGGGGGAGAACCGT ATATAAGTGCAGTAGTCGCCGTGAACGTTCTTTTTCGCAACGGGT TTGCCGCCAGAACACAGGTAAGTGCCGTGTGTGGTTCCCGCGGG CCTGGCCTCTTTACGGGTTATGGCCCTTGCGTGCCTTGAATTACT TCCACGCCCCTGGCTGCAGTACGTGATTCTTGATCCCGAGCTTC GGGTTGGAAGTGGGTGGGAGAGTTCGAGGCCTTGCGCTTAAGGA GCCCCTTCGCCTCGTGCTTGAGTTGAGGCCTGGCCTGGGCGCTG GGGCCGCCGCGTGCGAATCTGGTGGCACCTTCGCGCCTGTCTC GCTGCTTTCGATAAGTCTCTAGCCATTTAAAATTTTTGATGACCTG CTGCGACGCTTTTTTTCTGGCAAGATAGTCTTGTAAATGCGGGCC AAGATCTGCACACTGGTATTTCGGTTTTTGGGGCCGCGGGCGGC GACGGGGCCCGTGCGTCCCAGCGCACATGTTCGGCGAGGCGGG GCCTGCGAGCGCGGCCACCGAGAATCGGACGGGGGTAGTCTCA AGCTGGCCGGCCTGCTCTGGTGCCTGGCCTCGCGCCGCCGTGT ATCGCCCCGCCCTGGGCGGCAAGGCTGGCCCGGTCGGCACCAG TTGCGTGAGCGGAAAGATGGCCGCTTCCCGGCCCTGCTGCAGG GAGCTCAAAATGGAGGACGCGGCGCTCGGGAGAGCGGGCGGGT GAGTCACCCACACAAAGGAAAAGGGCCTTTCCGTCCTCAGCCGT CGCTTCATGTGACTCCACGGAGTACCGGGCGCCGTCCAGGCACC TCGATTAGTTCTCGAGCTTTTGGAGTACGTCGTCTTTAGGTTGGG GGGAGGGGTTTTATGCGATGGAGTTTCCCCACACTGAGTGGGTG GAGACTGAAGTTAGGCCAGCTTGGCACTTGATGTAATTCTCCTTG GAATTTGCCCTTTTTGAGTTTGGATCTTGGTTCATTCTCAAGCCTC AGACAGTGGTTCAAAGTTTTTTTCTTCCATTTCAGGTGTCGTGAAA ACTACCCCTAAAAGCCAAAA (SEQ ID NO: 19) |

TABLE 5

Developmental Genes for Screen

| Human Target Gene ID | Target Gene Symbol | Human Target Transcript | Human Genomic Sequence | Lineage | KO phenotype | References (PMID) |
|---|---|---|---|---|---|---|
| 64321 | Sox17 | NM_022454.3 | NC_000008.11 | all endoderm | die at E10.5, deficient of gut endoderm. In the chimeras, few in foregut and completely excluded from the mid- and hindgut | 11973269 |
| 1045 | Cdx2 | NM_001265.5 | NC_000013.11 | intestines (also VE) | rescue the embryos to E11.5 in tetrapioid chimera, defect in yolk sac circulation | 15136723 |
| 3172 | Hnf4a | NM_178849.2 | NC_000020.11 | liver, pancreas, colon (also VE) | rescue the embryos to midgestation stages (E12.5) in tetrapioid chimera | 10691738 |
| 2626 | Gata4 | NM_001308093.1 | NC_000008.11 | heart (also VE) | rescue the embryos to E9.5 in tetrapioid chimera | 15310850 |
| 2627 | Gata6 | NM_005257.5 | NC_000018.10 | liver (also VE) | rescue the embryos to E10.5 in tetrapioid chimera | 15767668 |
| 861 | Runx1 | NM_001754.4 | NC_000021.9 | hematopoiesis | die at E11.5 | 8565077 |
| 3170 | Foxa2 | NM_021784.4 | NC_000020.11 | notochord, all germ layer | die at E11.5. Absence of head process and notochord | 8069909 |
| 3651 | Pdx1 | NM_000209.3 | NC_000013.11 | pancreas | die within a few days after birth | 7935793 |
| 7080 | Nkx2-1 | NM_001079668.2 | NC_000014.9 | lung | die at birth | 10706142 |
| 1482 | Nkx2-5 | NM_004387.3 | NC_000005.10 | heart | die at E9-10, heart looping morphogenesis defect | 7628699 |
| 6662 | Sox9 | NM_000346.3 | NC_000017.11 | ductal system, chondrocyte | die at E11.5. In chimeras, excluded from chondrogenic mesenchymal | 10319868 |
| 5629 | Prox1 | NM_001270616.1 | NC_000001.11 | lymphatic endothelial, liver, lens | die at E14.5 | 10080188, 10499794 |
| 6615 | Snai1 | NM_005985.3 | NC_000020.11 | EMT | no mesoderm, die at E8.5 | 11689706 |
| 7291 | Twist1 | NM_000474.3 | NC_000007.14 | EMT | die at E11.5, defects in head mesenchyme | 7729687 |
| 429 | Ascl1 | NM_004316.3 | NC_000012.12 | neural | delayed neuronal differentiation | 16677628 |
| 4762 | Neurog1 | NM_006161.2 | NC_000005.10 | neural | neonatal lethal, fail to generate the proximal subset of cranial sensory neurons | 9539122 |

TABLE 5-continued

Developmental Genes for Screen

| Human Target Gene ID | Target Gene Symbol | Human Target Transcript | Human Genomic Sequence | Lineage | KO phenotype | References (PMID) |
|---|---|---|---|---|---|---|
| 1316 | Klf6 | NM_145027.5 | NC_000010.11 | hematopoiesis, yolk sac, liver | die at E12.5 | 16234353 |
| 10365 | Klf2 | NM_004520.4 | NC_000019.10 | endothelia | loss of vessel tone, die at E9.5; Tie2-cre Klf fl/fl die E14.5 | 17141159 |
| 3280 | Hes1 | NM_005524.3 | NC_000003.12 | brain | die at E12-birth, lethal due to severe neural tube defects | 8543157 |
| 2290 | Foxg1 | NM_005249.4 | NC_000014.9 | brain | die at birth, excess of Cajal-Retzius neuron, repression of cortical fate | 14704420 |
| 7289 | Tulp3 | NM_003324.4 | NC_000012.12 | neural | die at E14.5, betaIII-tubulin positive cells is significantly decreased in the hindbrain | 11406614 |
| 4656 | MyoG | NM_002479.5 | NC_000001.11 | muscle | die immediately after birth with severe skeletal muscle deficiency | 8393145 |
| 2625 | Gata3 | NM_001002295.1 | NC_000010.11 | T cell development, endothelial lineage | die by 11 days post coitum (d.p.c.) | 10835639 |
| 2263 | Fgfr2 | NM_000141.4 | NC_000010.11 | limb formation, skin, kidney, bone | lethality at E10-11 because of failures in the formation of functional placenta. Fail to form limb buds. | 26273516 |

TABLE 6

Editing Efficiencies of sgRNAs

| sgRNA | Editing Rate | Number of Reads |
|---|---|---|
| ASCL1-1 | 88.82% | 32222 |
| ASCL1-2 | 100.00% | 193295 |
| CDX2-1 | 95.78% | 477555 |
| CDX2-2 | 84.09% | 380163 |
| FGFR2-1 | 4.50% | 299260 |
| FGFR2-2 | 11.89% | 351448 |
| FOXA2-1 | 47.55% | 283036 |
| FOXA2-2 | 55.73% | 373681 |
| FOXG1-1 | 64.73% | 350961 |
| FOXG1-2 | 46.34% | 308417 |
| GATA3-1 | 70.51% | 242985 |
| GATA3-2 | 55.86% | 288202 |
| GATA4-1 | 61.46% | 188486 |
| GATA6-1 | 68.34% | 252259 |
| GATA6-2 | 100.00% | 4056 |
| HES1-1 | 99.97% | 32556 |
| HES1-2 | 97.99% | 2535 |
| HNF4A-1 | 0.00% | 0 |
| HNF4A-2 | 35.98% | 369691 |
| KLF6-1 | 86.19% | 354299 |
| KLF6-2 | 71.22% | 314585 |
| MYOG-1 | 92.11% | 368909 |
| MYOG-2 | 83.86% | 462448 |
| NEUROG1-1 | 40.20% | 456686 |
| NKX2-1-1 | 58.44% | 323414 |
| NKX2-1-2 | 75.11% | 353478 |
| NKX2-5-1 | 92.35% | 43639 |
| NKX2-5-2 | 100.00% | 13884 |
| PDX1-1 | 100.00% | 21621 |
| PDX1-2 | 94.55% | 2201 |
| PROX1-1 | 53.05% | 381734 |
| PROX1-2 | 66.88% | 449641 |
| RUNX1-1 | 69.57% | 406677 |
| RUNX1-2 | 99.99% | 286718 |
| SNAI1-1 | 36.09% | 306442 |
| SNAI1-2 | 62.92% | 353088 |
| SOX17-1 | 34.28% | 354167 |
| SOX17-2 | 36.82% | 455174 |

TABLE 6-continued

Editing Efficiencies of sgRNAs

| sgRNA | Editing Rate | Number of Reads |
|---|---|---|
| SOX9-1 | 69.91% | 290480 |
| SOX9-2 | 90.23% | 334831 |
| TULP3-1 | 66.87% | 317228 |
| TULP3-2 | 98.94% | 2457 |
| TWIST1-1 | 80.20% | 155792 |
| TWIST1-2 | 70.21% | 324104 |

TABLE 7 miRNA Sequences, Target Sites, and Lineage Specificities in Use

| miRNA | Specificity | Sequence | Target Site |
|---|---|---|---|
| miR-21 | Pluripotent Stem Cells/ Tumors | UAGCUUAUCAGACUGAUGUUGA (SEQ ID NO: 20) | TCAACATCAGTCTGATAAGCTA (SEQ ID NO: 1) |
| miR-122 | Liver | UGGAGUGUGACAAUGGUGUUUGU (SEQ ID NO: 21) | CAAACACCATTGTCACACTCCA (SEQ ID NO: 2) |
| miR-124 | Neural | UAAGGCACGCGGUGAAUGCCA (SEQ ID NO: 22) | GGCATTCACCGCGTGCCTTA (SEQ ID NO: 3) |
| miR-126 | Endothelial Cells | UCGUACCGUGAGUAAUAAUGC (SEQ ID NO: 23) | CGCATTATTACTCACGGTACGA |
| miR-302A | Pluripotent Stem Cells | ACUUAAACGUGGUUGUACUUGC (SEQ ID NO: 24) | AGCAAGTACATCCACGTTTAAGT (SEQ ID NO: 5) |

TABLE 8

Additional miRNA Sequences and Lineage Specificities

| miRNA | Specificity | Sequence |
|---|---|---|
| miR-1 | Cardiac | UGGAAUGUAAAGAAGUAUGUA (SEQ ID NO: 25) |
| miR-7 | Pituitary / Pancreatic Beta Cells | UGGAAGACUAGUGAUUUUGUUG (SEQ ID NO: 26) |
| miR-9 | Neural | UCUUUGGUUAUCUAGCUGUAUGA (SEQ ID NO: 27) |
| miR-10 | Kidney, Intestine, Lung, Spleen | UACCCUGUAGAUCCGAAUUUGUG (SEQ ID NO: 28) |
| miR-96 | Hair Cells | UUUGGCACUAGCACAUUUUUGC (SEQ ID NO: 29) |
| miR-133 | Muscle | UUGGUCCCCUUCAACCAGCUGU (SEQ ID NO: 30) |
| miR-137 | Dentate Gyrus, Hippocampus, Colonic Epithelium | UAUUGCUUAAGAAUACGCGUAG (SEQ ID NO: 31) |
| miR-140 | Cartilage | AGUGGUUUUACCCUAUGGUAG (SEQ ID NO: 32) |
| miR-143 | Cardiac | UGAGAUGAAGCACUGUAGCUCA (SEQ ID NO: 33) |
| miR-145 | Vascular Smooth Muscle | GUCCAGUUUUCCCAGGAAUCCCUU (SEQ ID NO: 34) |
| miR-181 | B Cells | AACAUUCAACGCUGUCGGUGAGU (SEQ ID NO: 35) |
| miR-184 | Brain, Testis, Corneal Epithelium | UGGACGGAGAACUGAUAAGGGU (SEQ ID NO: 36) |
| miR-199 | Skeleton Formation | CCCAGUGUUCAGACUACCUGUUC (SEQ ID NO: 37) |
| miR-200 | Epithelium | UAAUACUGCCUGGUAAUGAUGAC (SEQ ID NO: 38) |

TABLE 8-continued

Additional miRNA Sequences and Lineage Specificities

| miRNA | Specificity | Sequence |
|---|---|---|
| miR-203 | Skin | GUGAAAUGUUUAGGACCACUAG (SEQ ID NO: 39) |
| miR-208a | Cardiac | GAGCUUUUGGCCCGGGUUAUAC (SEQ ID NO: 40) |
| miR-214 | Skeleton Formation | ACAGCAGGCACAGACAGGCAG (SEQ ID NO: 41) |
| miR-218 | Motor Neurons | UUGUGCUUGAUCUAACCAUGU (SEQ ID NO: 42) |
| miR-223 | Myeloid Lineage | UGUCAGUUUGUCAAAUACCCC (SEQ ID NO: 43) |
| miR-338 | Neural | UCCAGCAUCAGUGAUUUUGUUGA (SEQ ID NO: 44) |
| miR-375 | Pancreatic Islets, Brain, Spinal Cord | UUUGUUCGUUCGGCUCGCGUGA (SEQ ID NO: 45) |
| miR-451 | Blood | AAACCGUUACCAUUACUGAGUU (SEQ ID NO: 46) |

NOTE:
These can be used singly or in combination.

REFERENCES

1. Xu, J., Du, Y. & Deng, H. Direct lineage reprogramming: strategies, mechanisms, and applications. Cell Stem Cell 16, 119-34 (2015).
2. Davis, Robert L; Weintraub, Harold; Lassar, A. B. Expression of a single transfected cDNA converts fibroblasts to myoblasts. Cell 51, 987-1000 (1987).
3. Takahashi, K. & Yamanaka, S. Induction of pluripotent stem cells from mouse embryonic and adult fibroblast cultures by defined factors. Cell 126, 663-76 (2006).
4. Takahashi, K. et al. Induction of pluripotent stem cells from adult human fibroblasts by defined factors. Cell 131, 861-72 (2007).
5. Yu, J. et al. Induced Pluripotent Stem Cell Lines Derived from Human Somatic Cells. Science 318, 1917-1920 (2007).
6. Wernig, M. et al. In vitro reprogramming of fibroblasts into a pluripotent ES-cell-like state. Nature 448, 318-324 (2007).
7. Maherali, N. et al. Directly Reprogrammed Fibroblasts Show Global Epigenetic Remodeling and Widespread Tissue Contribution. Cell Stem Cell 1, 55-70 (2007).
8. Park, I.-H. et al. Reprogramming of human somatic cells to pluripotency with defined factors. Nature 451, 141-146 (2008).
9. Pang, Z. P. et al. Induction of human neuronal cells by defined transcription factors. Nature 476, 220-223 (2011).
10. Sugimura, R. et al. Haematopoietic stem and progenitor cells from human pluripotent stem cells. Nature 545, 432-438 (2017).
11. Yang, N. et al. Generation of pure GABAergic neurons by transcription factor programming. Nat. Methods 14, 621-628 (2017).
12. Sugimura, R. et al. Haematopoietic stem and progenitor cells from human pluripotent stem cells. Nature 545, 432-438 (2017).
13. Zhang, Y. et al. Rapid single-step induction of functional neurons from human pluripotent stem cells. Neuron 78, 785-98 (2013).
14. Abujarour, R. et al. Myogenic differentiation of muscular dystrophy-specific induced pluripotent stem cells for use in drug discovery. Stem Cells Transl. Med. 3, 149-60 (2014).
15. Chanda, S. et al. Generation of induced neuronal cells by the single reprogramming factor ASCL1. Stem Cell Reports 3, 282-96 (2014).
16. Mali, P. et al. CAS9 transcriptional activators for target specificity screening and paired nickases for cooperative genome engineering. Nat. Biotechnol. 31, 833-838 (2013).
17. Qi, L. S. et al. Repurposing CRISPR as an RNA-Guided Platform for Sequence-Specific Control of Gene Expression. Cell 152, 1173-1183 (2013).
18. Gilbert, L. A. et al. CRISPR-Mediated Modular RNA-Guided Regulation of Transcription in Eukaryotes. Cell 154, 442-451 (2013).
19. Konermann, S. et al. Genome-scale transcriptional activation by an engineered CRISPR-Cas9 complex. Nature 517, 583-588 (2014).
20. Polstein, L. R. & Gersbach, C. a. A light-inducible CRISPR-Cas9 system for control of endogenous gene activation. Nat. Chem. Biol. 11, 198-200 (2015).
21. Nihongaki, Y., Yamamoto, S., Kawano, F., Suzuki, H. & Sato, M. CRISPR-Cas9-based Photoactivatable Transcription System. Chem. Biol. 22, 169-174 (2015).
22. Nihongaki, Y. et al. CRISPR-Cas9-based photoactivatable transcription systems to induce neuronal differentiation. Nat. Methods 14, 963-966 (2017).

What is claimed is:

1. An in vitro or ex vivo method of producing a lineage-specific target cell population from a teratoma comprising a lineage-specific miRNA of the target cell population, the method comprising:
   contacting the teratoma with a lineage-specific miRNA binding polynucleotide comprising a lineage-specific miRNA binding site specific to the lineage-specific miRNA of the target cell population operably linked to a polynucleotide encoding a prodrug modification polypeptide; and
   contacting the teratoma with a prodrug;
   thereby producing the lineage-specific target cell population.

2. The method of claim 1, wherein the prodrug modification polypeptide is selected from the group consisting of: a viral tyrosine kinase, a bacterial cytosine deaminase, carboxypeptidase G2, purine nucleoside phosphorylase, nitroreductase, deoxycytidine kinase, cytochrome P450, a horseradish peroxidase, a guanine ribosyltransferase, a β-glucuronidase, a β-galactosidase, a thymidine phosphorylase, and methionine-α, γ-lyase.

3. The method of claim 1, wherein the prodrug is cytotoxic when modified by the prodrug modification polypeptide; and wherein the prodrug is selected from the group consisting of: ganciclovir, penciclovir, acyclovir, valacyclovir, (E)-5-(2-bromovinyl)-2'-deoxyuridine (BVDU), zidovudine, 2'-exo-methanocarbathymidine, 5-fluorocytosine, 5-methylpurine deoxyriboside (MEP), fludarabine, cyclophosphamide, ifosfamide, acetaminophen,4-ipomeanol, 4-[(2-chloroethyl)(2-mesyloxyethyl)amino]benzoyl-L-glutamic acid (CMDA), hydroxy-aniline mustards, amino-ainiline mustards, anthracycline glutamates, methotrexate a-peptides, irinotecan, anthracycline acetals, CB1954, SN23862, 4-nitrobenzyl carbamates, quinones, indole-3-acetic acid, 6-thioxanthine, HM1826, anthracycline acetals, 5'-deoxy-5-fluorouridine, and selenomethionine.

4. The method of claim 1, wherein the prodrug is ganciclovir or an equivalent thereof.

5. The method of claim 4, wherein the prodrug modification polypeptide is herpes simplex virus thymidine kinase (HSV-tk) or an equivalent thereof.

6. The method of claim 1, wherein the lineage-specific miRNA corresponds to a cell lineage selected from the group consisting of: pluripotent stem cells, tumors, liver cells, neural cells and endothelial cells; and wherein the lineage-specific miRNA binding site is capable of binding a polynucleotide selected from the group consisting of: miR-21, miR-122, miR-124, miR-126, miR302A, miR-1, miR-7, miR-9, miR-10, miR-96, miR-133, miR-137, miR-140, miR-143, miR-145, miR-181, miR-184, miR-199, miR-200, miR-203, miR-208a, miR-214, miR-218, miR-223, miR-338, miR-375, and miR-451.

7. The method of claim 1, wherein the lineage-specific miRNA binding polynucleotide comprises two or more miRNA binding sites that binds to two or more lineage-specific miRNAs in the teratoma.

8. The method of claim 1, further comprising exposing the teratoma to a growth medium that is compatible with biasing differentiation of the teratoma.

9. The method of claim 8, wherein the growth medium is an endothelial growth medium.

10. The method of claim 1, further comprising overexpressing in the teratoma at least one transcription factor capable of biasing differentiation of the teratoma.

11. The method of claim 10, wherein the transcription factor comprises ETV2, MYOD1 or NEUROD1.

12. The method of claim 1, wherein the lineage-specific target cell population is an organ, an organoid, a tissue, or individual transplantable cells.

13. A method of producing a lineage-specific target cell population from a teratoma comprising:
   administering a prodrug to a teratoma comprising a lineage-specific miRNA-binding polynucleotide,
   wherein the lineage specific miRNA binding polynucleotide comprises a lineage-specific miRNA-binding site operably linked to a polynucleotide encoding a prodrug modification polypeptide, and
   wherein the teratoma comprises at least one cell type that expresses a lineage-specific miRNA that binds to the lineage-specific miRNA binding site;
   overexpressing in the teratoma at least one transcription factor capable of biasing differentiation of the teratoma; and
   exposing the teratoma to a growth medium, wherein the growth medium is compatible with biasing differentiation of the teratoma; and
   thereby producing the lineage-specific target cell population;
   optionally wherein the teratoma is derived from human pluripotent stem cells (hPSCs), or an ex vivo tissue engineered construct.

14. The method of claim 13, wherein the transcription factor comprises ETV2, MYOD1 or NEUROD1.

15. The method of claim 13, wherein the growth medium is an endothelial growth medium.

16. A lineage-specific target cell population prepared by the method of claim 13, wherein optionally the population is substantially homogeneous or heterogeneous.

* * * * *